US010695454B2

(12) United States Patent
Conroy et al.

(10) Patent No.: US 10,695,454 B2
(45) Date of Patent: Jun. 30, 2020

(54) METHOD AND SYSTEM OF SENSOR FEEDBACK FOR A SCENT DIFFUSION DEVICE

(71) Applicants: Thomas A. Conroy, Newtown, CT (US); Todd H. Becker, Ridgefield, CT (US); Thomas G. Siegel, Ridgefield, CT (US)

(72) Inventors: Thomas A. Conroy, Newtown, CT (US); Todd H. Becker, Ridgefield, CT (US); Thomas G. Siegel, Ridgefield, CT (US)

(73) Assignee: SCENTBRIDGE HOLDINGS, LLC, Ridgefield, CT (US)

( * ) Notice: Subject to any disclaimer, the term of this patent is extended or adjusted under 35 U.S.C. 154(b) by 0 days.

(21) Appl. No.: 14/689,664

(22) Filed: Apr. 17, 2015

(65) Prior Publication Data
US 2015/0297778 A1    Oct. 22, 2015

Related U.S. Application Data

(60) Provisional application No. 61/981,533, filed on Apr. 18, 2014, provisional application No. 62/045,989, filed on Sep. 4, 2014.

(51) Int. Cl.
*B05B 17/04*    (2006.01)
*A61L 9/14*    (2006.01)
(Continued)

(52) U.S. Cl.
CPC ................................ *A61L 9/14* (2013.01); *A61L 2/00* (2013.01); *A61L 9/00* (2013.01); *A61L 9/015* (2013.01);
(Continued)

(58) Field of Classification Search
CPC ....................................... B05B 1/30; B05B 12/02; B05B 12/12; B05B 12/14
(Continued)

(56) References Cited

U.S. PATENT DOCUMENTS

| 4,483,466 A | 11/1984 | Gutierrez |
| 4,544,086 A | 10/1985 | Hill et al. |

(Continued)

FOREIGN PATENT DOCUMENTS

| CN | 200962792 Y | 10/2007 |
| CN | 204860697 U | 12/2015 |

(Continued)

OTHER PUBLICATIONS

"Febreze Home™", http://www.febrezehome.com/product/connect/ (accessed Jan. 22, 2016), 4 pages.

(Continued)

*Primary Examiner* — Davis D Hwu
(74) *Attorney, Agent, or Firm* — Lando & Anastasi, LLP

(57) ABSTRACT

The disclosure herein concerns a method including receiving at a computer at least one target value of a scent parameter for an environment that is remote from the computer, receiving at the computer a sensed parameter of the environment, and controlling, via the computer, diffusion of a liquid from a source of the liquid in fluid communication with at least one scent diffusion device to achieve the target value of the scent parameter, wherein controlling includes setting or adjusting an operation parameter of the at least one scent diffusion device in response to the sensed parameter.

42 Claims, 24 Drawing Sheets

(51) Int. Cl.

| | |
|---|---|
| *B05B 7/24* | (2006.01) |
| *G06Q 10/06* | (2012.01) |
| *G06Q 10/08* | (2012.01) |
| *B05B 12/08* | (2006.01) |
| *G08B 21/18* | (2006.01) |
| *B05B 12/12* | (2006.01) |
| *G05B 15/02* | (2006.01) |
| *G08B 13/22* | (2006.01) |
| *A61L 2/00* | (2006.01) |
| *A61L 9/00* | (2006.01) |
| *B01F 3/04* | (2006.01) |
| *A61L 9/015* | (2006.01) |
| *A61L 9/12* | (2006.01) |
| *B05B 7/26* | (2006.01) |
| *G08B 23/00* | (2006.01) |
| *G01F 23/30* | (2006.01) |
| *G01F 23/72* | (2006.01) |

(52) U.S. Cl.
CPC ............ *A61L 9/12* (2013.01); *B01F 3/04021* (2013.01); *B05B 7/2416* (2013.01); *B05B 7/2424* (2013.01); *B05B 7/2489* (2013.01); *B05B 7/262* (2013.01); *B05B 12/08* (2013.01); *B05B 12/081* (2013.01); *B05B 12/12* (2013.01); *G05B 15/02* (2013.01); *G06Q 10/06* (2013.01); *G06Q 10/08* (2013.01); *G08B 13/22* (2013.01); *G08B 21/182* (2013.01); *G08B 23/00* (2013.01); *A61L 2209/11* (2013.01); *A61L 2209/111* (2013.01); *A61L 2209/133* (2013.01); *A61L 2209/135* (2013.01); *A61L 2209/16* (2013.01); *A61L 2209/20* (2013.01); *B01F 2215/009* (2013.01); *G01F 23/30* (2013.01); *G01F 23/72* (2013.01)

(58) Field of Classification Search
USPC ............................................ 239/67–70, 6, 11
See application file for complete search history.

(56) References Cited

U.S. PATENT DOCUMENTS

| | | |
|---|---|---|
| 4,690,312 A | 9/1987 | Crapser et al. |
| 4,764,312 A | 8/1988 | Scharres et al. |
| 4,816,951 A | 3/1989 | Zago et al. |
| 4,830,791 A | 5/1989 | Muderlak et al. |
| 4,836,452 A | 6/1989 | Fox et al. |
| 4,877,989 A | 10/1989 | Drews et al. |
| 4,967,395 A | 10/1990 | Watanabe et al. |
| 4,989,755 A | 2/1991 | Shiau |
| 5,014,881 A | 5/1991 | Andris |
| 5,014,884 A | 5/1991 | Wunsch |
| 5,038,972 A | 8/1991 | Muderlak et al. |
| 5,055,822 A | 10/1991 | Campbell et al. |
| 5,069,876 A | 12/1991 | Oshinsky |
| 5,134,961 A | 8/1992 | Giles et al. |
| 5,174,967 A | 12/1992 | Fukuhara |
| 5,198,157 A | 3/1993 | Bechet |
| 5,249,718 A | 10/1993 | Muderlak |
| 5,269,445 A | 12/1993 | Tobler |
| 5,337,926 A | 8/1994 | Drobish et al. |
| 5,342,584 A | 8/1994 | Fritz et al. |
| 5,353,744 A | 10/1994 | Custer |
| 5,383,580 A | 1/1995 | Winder |
| RE34,847 E | 2/1995 | Muderlak et al. |
| 5,392,768 A | 2/1995 | Johansson et al. |
| 5,394,866 A | 3/1995 | Ritson et al. |
| 5,409,839 A | 4/1995 | Balestrieri et al. |
| 5,445,324 A | 8/1995 | Berry et al. |
| 5,449,117 A | 9/1995 | Muderlak et al. |
| 5,450,336 A | 9/1995 | Rubsamen et al. |
| 5,489,047 A | 2/1996 | Winder |
| 5,497,764 A | 3/1996 | Ritson et al. |
| 5,503,303 A | 4/1996 | LaWare et al. |
| 5,520,166 A | 5/1996 | Ritson et al. |
| 5,522,378 A | 6/1996 | Ritson et al. |
| 5,527,493 A | 6/1996 | McElfresh et al. |
| 5,531,344 A | 7/1996 | Winner |
| 5,542,605 A | 8/1996 | Campau |
| 5,591,409 A | 1/1997 | Watkins |
| 5,609,047 A | 3/1997 | Hellman et al. |
| 5,610,674 A | 3/1997 | Martin |
| 5,622,162 A | 4/1997 | Johansson et al. |
| D380,821 S | 7/1997 | Chen |
| 5,647,388 A | 7/1997 | Butler, Jr. et al. |
| 5,651,942 A | 7/1997 | Christensen |
| 5,657,910 A | 8/1997 | Keyser |
| 5,673,825 A | 10/1997 | Chen |
| 5,675,070 A | 10/1997 | Gelperin |
| 5,676,283 A | 10/1997 | Wang |
| 5,695,091 A | 12/1997 | Winings et al. |
| 5,702,036 A | 12/1997 | Ferrara, Jr. |
| 5,735,918 A | 4/1998 | Barradas |
| 5,743,251 A | 4/1998 | Howell et al. |
| 5,743,252 A | 4/1998 | Rubsamen et al. |
| 5,755,218 A | 5/1998 | Johansson et al. |
| 5,772,074 A | 6/1998 | Dial et al. |
| 5,810,265 A | 9/1998 | Cornelius et al. |
| 5,823,390 A | 10/1998 | Muderlak et al. |
| 5,826,570 A | 10/1998 | Goodman et al. |
| 5,853,129 A | 12/1998 | Spitz |
| 5,884,808 A | 3/1999 | Muderlak et al. |
| 5,898,475 A | 4/1999 | Martin |
| 5,908,140 A | 6/1999 | Muderlak et al. |
| 5,922,247 A | 7/1999 | Shoham et al. |
| 5,924,597 A | 7/1999 | Lynn |
| 5,938,076 A | 8/1999 | Ganzeboom |
| 6,000,658 A | 12/1999 | McCall, Jr. |
| 6,006,957 A | 12/1999 | Kunesh |
| 6,026,987 A | 2/2000 | Burnett et al. |
| 6,029,659 A | 2/2000 | O'Connor |
| 6,029,911 A | 2/2000 | Watanabe et al. |
| 6,036,108 A | 3/2000 | Chen |
| 6,039,212 A | 3/2000 | Singh |
| 6,053,041 A | 4/2000 | Sinha |
| 6,065,683 A | 5/2000 | Akin et al. |
| 6,092,912 A | 7/2000 | Nelson |
| 6,098,896 A | 8/2000 | Haruch |
| 6,110,356 A | 8/2000 | Hedrick et al. |
| 6,142,457 A | 11/2000 | Holtan et al. |
| 6,182,904 B1 | 2/2001 | Ulczynski et al. |
| 6,216,925 B1 | 4/2001 | Garon |
| 6,237,812 B1 | 5/2001 | Fukada |
| 6,254,065 B1 | 7/2001 | Ehrensperger et al. |
| 6,267,297 B1 * | 7/2001 | Contadini .................. A61L 9/12 222/646 |
| 6,293,442 B1 | 9/2001 | Mollayan |
| 6,297,297 B1 | 10/2001 | Brookman et al. |
| 6,371,388 B2 | 4/2002 | Utter et al. |
| 6,394,310 B1 | 5/2002 | Muderlak et al. |
| 6,405,944 B1 | 6/2002 | Benalikhoudja |
| D460,544 S | 7/2002 | Garcia |
| 6,419,122 B1 | 7/2002 | Chown |
| 6,478,199 B1 | 11/2002 | Shanklin et al. |
| 6,510,561 B1 | 1/2003 | Hammond et al. |
| 6,516,796 B1 | 2/2003 | Cox et al. |
| 6,719,217 B1 | 4/2004 | Tawara et al. |
| 6,739,479 B2 | 5/2004 | Contadini et al. |
| 6,751,886 B2 | 6/2004 | Chang et al. |
| 6,790,408 B2 | 9/2004 | Whitby et al. |
| 6,802,460 B2 * | 10/2004 | Hess .......................... A61L 2/18 239/102.1 |
| 6,827,289 B2 | 12/2004 | Filicicchia et al. |
| 6,830,368 B2 | 12/2004 | Fukano |
| 6,852,278 B2 | 2/2005 | Richards |
| 6,901,609 B2 | 6/2005 | Hill |
| 6,913,733 B2 | 7/2005 | Hardy et al. |
| 6,925,752 B1 | 8/2005 | Cherry et al. |
| 6,944,889 B2 | 9/2005 | Hill |
| 6,969,008 B2 | 11/2005 | Helf et al. |
| 6,969,012 B2 | 11/2005 | Kangas et al. |

(56) References Cited

U.S. PATENT DOCUMENTS

| | | |
|---|---|---|
| 7,011,795 B2 | 3/2006 | Thompson et al. |
| 7,021,494 B2 | 4/2006 | Mazooji et al. |
| 7,040,551 B2 | 5/2006 | Rummel |
| 7,080,793 B2 | 7/2006 | Borisov et al. |
| 7,111,975 B2 | 9/2006 | Fenton et al. |
| 7,137,269 B1 | 11/2006 | Maranville |
| 7,188,485 B2 | 3/2007 | Szpekman |
| 7,207,712 B2 | 4/2007 | Kozyuk |
| 7,223,166 B1 | 5/2007 | Wiseman, Sr. et al. |
| 7,284,899 B2 | 10/2007 | Nakano |
| 7,314,306 B2 | 1/2008 | Kozyuk |
| 7,350,721 B2 | 4/2008 | Ghazarian |
| 7,363,737 B2 | 4/2008 | Benalikhoudja |
| 7,389,943 B2 | 6/2008 | Jaworski |
| 7,398,013 B2 | 7/2008 | He et al. |
| 7,407,118 B2 | 8/2008 | Sevy |
| 7,572,107 B2 | 8/2009 | Heller et al. |
| 7,610,118 B2 | 10/2009 | Schramm et al. |
| 7,651,077 B1 | 1/2010 | Rosener et al. |
| 7,656,300 B2 | 2/2010 | Ronnau |
| 7,664,574 B2 | 2/2010 | Imhof et al. |
| 7,698,246 B2 | 4/2010 | Friedlander et al. |
| 7,708,453 B2 | 5/2010 | Kozyuk |
| 7,712,683 B2 | 5/2010 | Robert et al. |
| 7,725,565 B2 | 5/2010 | Li et al. |
| 7,762,715 B2 | 7/2010 | Gordon et al. |
| 7,913,933 B2 | 3/2011 | Van Roemburg |
| 7,916,951 B2 | 3/2011 | Landwehr et al. |
| 7,926,792 B2 | 4/2011 | Pankhurst et al. |
| 7,930,068 B2 | 4/2011 | Robert et al. |
| 7,992,803 B2 | 8/2011 | Mahoney et al. |
| 8,042,989 B2 | 10/2011 | Gordon et al. |
| 8,047,813 B2 | 11/2011 | Sevy |
| 8,048,379 B2 | 11/2011 | Sassoon |
| 8,181,644 B2 | 5/2012 | Mullinger et al. |
| 8,249,731 B2 | 8/2012 | Tran et al. |
| 8,293,170 B1 | 10/2012 | Schuld |
| 8,320,751 B2 | 11/2012 | Porchia et al. |
| 8,371,740 B2 | 2/2013 | Pestl et al. |
| 8,382,008 B1 | 2/2013 | Ricciardi et al. |
| 8,385,730 B2 | 2/2013 | Bushman et al. |
| 8,386,283 B2 | 2/2013 | Hand |
| 8,413,688 B2 | 4/2013 | Bassoli |
| 8,419,377 B2 | 4/2013 | Hsu |
| 8,459,499 B2 | 6/2013 | Sipinski |
| 8,603,398 B2 | 12/2013 | Broncano Atencia et al. |
| 8,655,827 B2 | 2/2014 | Pearson et al. |
| 8,775,406 B2 | 7/2014 | Gross |
| 8,855,827 B2 | 10/2014 | Weening et al. |
| 8,857,735 B2 | 10/2014 | Rosener et al. |
| 8,881,040 B2 | 11/2014 | Li |
| 8,881,999 B2 | 11/2014 | Blaylock et al. |
| 8,886,785 B2 | 11/2014 | Apte et al. |
| 8,939,386 B2 | 1/2015 | Robert et al. |
| 8,955,765 B2 | 2/2015 | Porchia et al. |
| 9,013,961 B1 | 4/2015 | Nicholson et al. |
| 9,162,004 B1 | 10/2015 | Ansley |
| 9,173,389 B2 | 11/2015 | Boyd et al. |
| 9,185,897 B2 | 11/2015 | Boyd et al. |
| 9,248,461 B2 | 2/2016 | Ansley et al. |
| D752,732 S | 3/2016 | Ansley et al. |
| 9,278,150 B2 | 3/2016 | Gruenbacher et al. |
| 9,307,763 B2 | 4/2016 | Ray et al. |
| 9,439,995 B2 | 9/2016 | Conroy et al. |
| 9,452,234 B2 | 9/2016 | Conroy et al. |
| 9,489,495 B2 | 11/2016 | Li et al. |
| 9,491,942 B2 | 11/2016 | Ray et al. |
| 9,529,974 B2 | 12/2016 | Li et al. |
| 2003/0177038 A1 | 9/2003 | Rao |
| 2004/0028551 A1 | 2/2004 | Kvietok et al. |
| 2004/0050963 A1 | 3/2004 | Ray et al. |
| 2005/0129568 A1 | 6/2005 | Kubby et al. |
| 2005/0175426 A1 | 8/2005 | Kroll et al. |
| 2006/0035380 A1 | 2/2006 | Saint-Leger |
| 2006/0060990 A1 | 3/2006 | Szpekman et al. |
| 2006/0175426 A1 | 8/2006 | Schramm et al. |
| 2007/0109763 A1 | 5/2007 | Wolf et al. |
| 2007/0143088 A1 | 6/2007 | Garland |
| 2007/0210182 A1 | 9/2007 | Wulteputte et al. |
| 2007/0258849 A1 | 11/2007 | Kent et al. |
| 2008/0046944 A1 | 2/2008 | Lee et al. |
| 2008/0069785 A1 | 3/2008 | Jones |
| 2008/0091461 A1 | 4/2008 | Evans et al. |
| 2008/0103054 A1 | 5/2008 | Williams et al. |
| 2008/0140348 A1 | 6/2008 | Frank |
| 2008/0172352 A1 | 7/2008 | Friedlander et al. |
| 2008/0193387 A1 | 8/2008 | De Wolff |
| 2008/0244429 A1 | 10/2008 | Stading |
| 2009/0076899 A1 | 3/2009 | Gbodimowo |
| 2009/0159719 A1 | 6/2009 | Millet et al. |
| 2009/0162253 A1 | 6/2009 | Porchia et al. |
| 2009/0319295 A1 | 12/2009 | Kass-Hout et al. |
| 2010/0001417 A1 | 1/2010 | D'Amico et al. |
| 2010/0030013 A1* | 2/2010 | Brunelle ............... A61M 21/00 600/27 |
| 2010/0044453 A1* | 2/2010 | Porchia ................. A01M 1/205 239/6 |
| 2010/0066540 A1 | 3/2010 | Theobald et al. |
| 2010/0070086 A1 | 3/2010 | Harrod et al. |
| 2010/0221143 A1 | 9/2010 | Broncano Atencia et al. |
| 2011/0020785 A1 | 1/2011 | Lowery, Jr. et al. |
| 2011/0034120 A1 | 2/2011 | Jaiyeola |
| 2011/0089252 A1 | 4/2011 | Rosener et al. |
| 2011/0089260 A1 | 4/2011 | Roemburg et al. |
| 2011/0200488 A1 | 8/2011 | Cennini et al. |
| 2011/0226864 A1 | 9/2011 | Kim et al. |
| 2011/0253797 A1 | 10/2011 | Weening et al. |
| 2011/0295434 A1 | 12/2011 | Luc et al. |
| 2012/0018037 A1 | 1/2012 | Nakagawa et al. |
| 2012/0018530 A1 | 1/2012 | Blaylock et al. |
| 2012/0031922 A1 | 2/2012 | Johnson et al. |
| 2012/0046790 A1 | 2/2012 | Anderson et al. |
| 2012/0091162 A1 | 4/2012 | Overhultz et al. |
| 2012/0097753 A1 | 4/2012 | Kelly et al. |
| 2012/0126024 A1 | 5/2012 | Boyd et al. |
| 2012/0211574 A1 | 8/2012 | Weening et al. |
| 2012/0261484 A2 | 10/2012 | Blaylock et al. |
| 2012/0324098 A1 | 12/2012 | De Jager et al. |
| 2013/0081541 A1* | 4/2013 | Hasenoehrl ............ A61L 9/035 96/222 |
| 2013/0082817 A1 | 4/2013 | Gruenbacher et al. |
| 2013/0231782 A1 | 9/2013 | Lee et al. |
| 2014/0022061 A1 | 1/2014 | Apte et al. |
| 2014/0022793 A1 | 1/2014 | Apte et al. |
| 2014/0022917 A1 | 1/2014 | Apte et al. |
| 2014/0022968 A1 | 1/2014 | Apte et al. |
| 2014/0025805 A1 | 1/2014 | Apte et al. |
| 2014/0052278 A1 | 2/2014 | McGuire et al. |
| 2014/0074283 A1 | 3/2014 | Blackburn et al. |
| 2014/0316911 A1 | 10/2014 | Gross |
| 2014/0322082 A1 | 10/2014 | Hasenoehrl et al. |
| 2015/0019029 A1 | 1/2015 | Chandler et al. |
| 2015/0019030 A1 | 1/2015 | Chandler et al. |
| 2015/0019041 A1 | 1/2015 | Chandler et al. |
| 2015/0028126 A1 | 1/2015 | Rosener et al. |
| 2015/0088273 A1 | 3/2015 | Gruenbacher et al. |
| 2015/0136158 A1 | 5/2015 | Stevens et al. |
| 2015/0297776 A1 | 10/2015 | Conroy et al. |
| 2015/0297777 A1 | 10/2015 | Conroy |
| 2015/0297778 A1 | 10/2015 | Conroy et al. |
| 2015/0297779 A1 | 10/2015 | Conroy |
| 2015/0367013 A1 | 12/2015 | Gruenbacher et al. |
| 2015/0367014 A1 | 12/2015 | Gruenbacher et al. |
| 2015/0367016 A1 | 12/2015 | Gruenbacher et al. |
| 2015/0367356 A1 | 12/2015 | Gruenbacher et al. |
| 2016/0000956 A1 | 1/2016 | Jenkins et al. |
| 2016/0030621 A1 | 2/2016 | Weening et al. |
| 2016/0081181 A1 | 3/2016 | Gruenbacher et al. |
| 2016/0187654 A1 | 6/2016 | Border et al. |
| 2016/0231720 A1 | 8/2016 | Choi et al. |
| 2016/0263265 A1 | 9/2016 | Fantuzzi et al. |

(56) References Cited

U.S. PATENT DOCUMENTS

2016/0339135 A1 11/2016 Becker et al.
2016/0339136 A1 11/2016 Becker et al.

FOREIGN PATENT DOCUMENTS

| CN | 204888441 U | 12/2015 |
|---|---|---|
| CN | 105494286 A | 4/2016 |
| CN | 205139689 U | 4/2016 |
| EP | 1184083 B1 | 7/2003 |
| EP | 2420137 A1 | 2/2012 |
| GB | 2233230 B | 7/1992 |
| WO | 2010080138 A1 | 7/2010 |
| WO | 2015161246 A1 | 10/2015 |
| WO | 2015161250 A1 | 10/2015 |

OTHER PUBLICATIONS

"Prolitec", htttps://prolitec.com/expertise/airq-technology (accessed Jan. 20, 2016), 3 pages.
"Scent Flow 1800", http://www.whitescent.co.il/en/products/systems/scent-flow-1800/ (accessed Jan. 20, 2016), 2 pages.
"ScentWave 1001", http://www.scentair.com/scentwave/1001/index.html (accessed Jan. 20, 2016), 3 pages.
"ScentWave 1004", http://www.scentair.com/scentwave/1004/index.html (accessed Jan. 20, 2016), 4 pages.
PCT/US2015/026460, "International Application Serial No. PCT/US2015/026460, International Search Report and Written Opinion dated Aug. 3, 2015", Conroy, Thomas A. et al, 9 pages.
PCT/US2015/026467, "International Application Serial No. PCT/US2015/026467, International Search Report and Written Opinion dated Jul. 27, 2015", Thomas A. Conroy, 10 Pages.
Pending U.S. Appl. No. 15/011,429, filed Jan. 29, 2016.
Abandoned U.S. Appl. No. 14/689,705, filed Apr. 17, 2015.
Extended European Search Report from corresponding European Application No. 15780002.0 dated Nov. 14, 2017.

* cited by examiner

RECEIVING AT A COMPUTER, LIQUID LEVEL DATA FROM A PLURALITY OF REMOTE ATOMIZING DIFFUSION DEVICES WHEREIN EACH DIFFUSION DEVICE COMPRISES A COMMUNICATIONS FACILITY THAT ENABLES TRANSMITTING SIGNALS TO AND RECEIVING SIGNALS FROM A REMOTE COMPUTER AND AT LEAST ONE LIQUID LEVEL SENSOR 902

BASED ON THE LIQUID LEVEL DATA, CREATING, VIA THE REMOTE COMPUTER, AN ELECTRONIC DATA STRUCTURE CHARACTERIZING THE TRANSFORMATION OF THE REMOTE DIFFUSION DEVICES, WHEREIN THE ELECTRONIC DATA STRUCTURE INCLUDES DATA SPECIFYING AT LEAST ONE OF THE PRODUCTION OF SCENT FRAGRANCE, THE PROCUREMENT OF SCENT FRAGRANCE, THE MANAGEMENT OF SCENT INVENTORY, AND THE DELIVERY OF SCENT INVENTORY 904

CAUSING THE REMOTE ATOMIZING DIFFUSION DEVICES TO IMPLEMENT THE TRANSFORMATION 908

FIG. 9

CREATING, VIA A REMOTE COMPUTER, AN ELECTRONIC DATA STRUCTURE CHARACTERIZING THE TRANSFORMATION OF AT LEAST ONE REMOTE DIFFUSION DEVICE, WHEREIN THE ELECTRONIC DATA STRUCTURE INCLUDES DATA REGARDING A SENSED PARAMETER OF AN ENVIRONMENT AND AT LEAST ONE TARGET VALUE OF A SCENT PARAMETER FOR THE ENVIRONMENT 1902

INITIATING CONTROL, VIA THE REMOTE COMPUTER, OF DIFFUSION OF A LIQUID FROM A SOURCE OF THE LIQUID IN FLUID COMMUNICATION WITH THE AT LEAST ONE SCENT DIFFUSION DEVICE IN ACCORDANCE WITH THE ELECTRONIC DATA STRUCTURE TO ACHIEVE THE TARGET VALUE OF THE SCENT PARAMETER IN RESPONSE TO THE SENSED PARAMETER 1904

FIG. 19

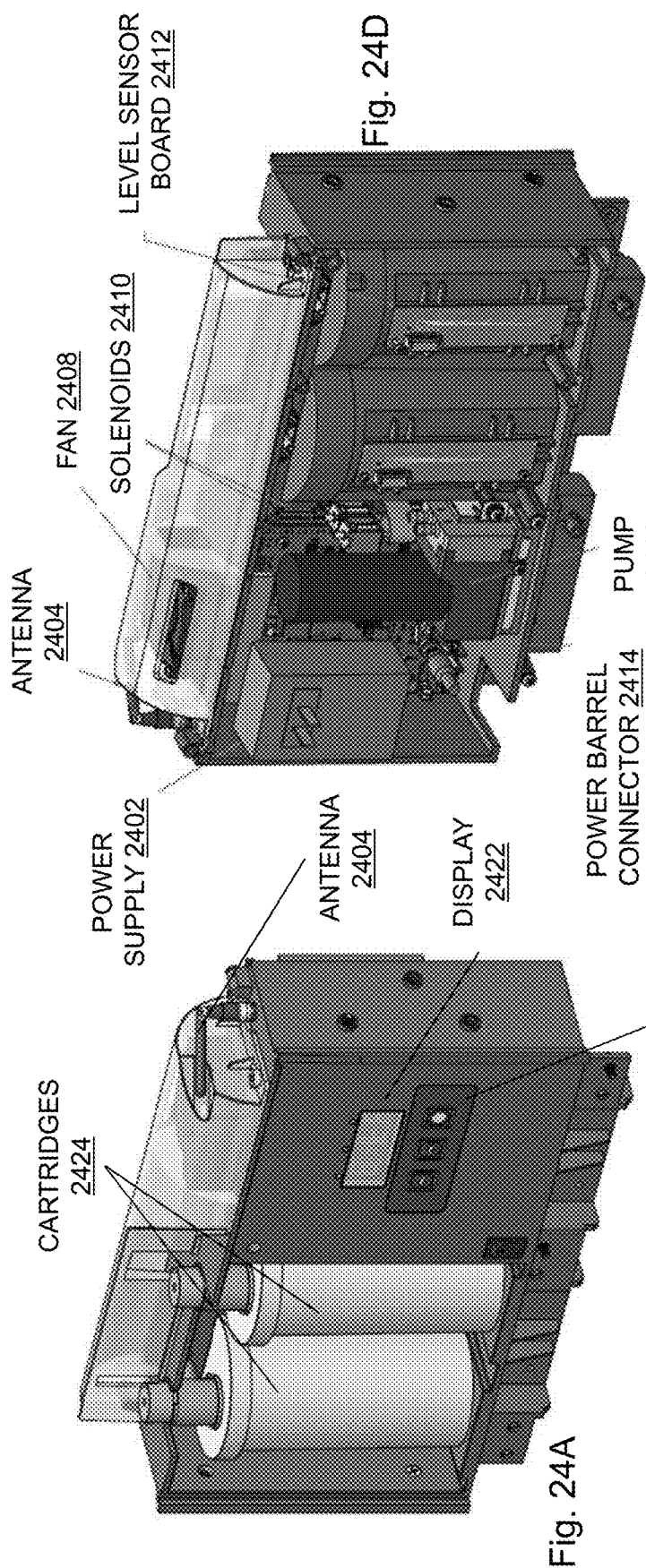
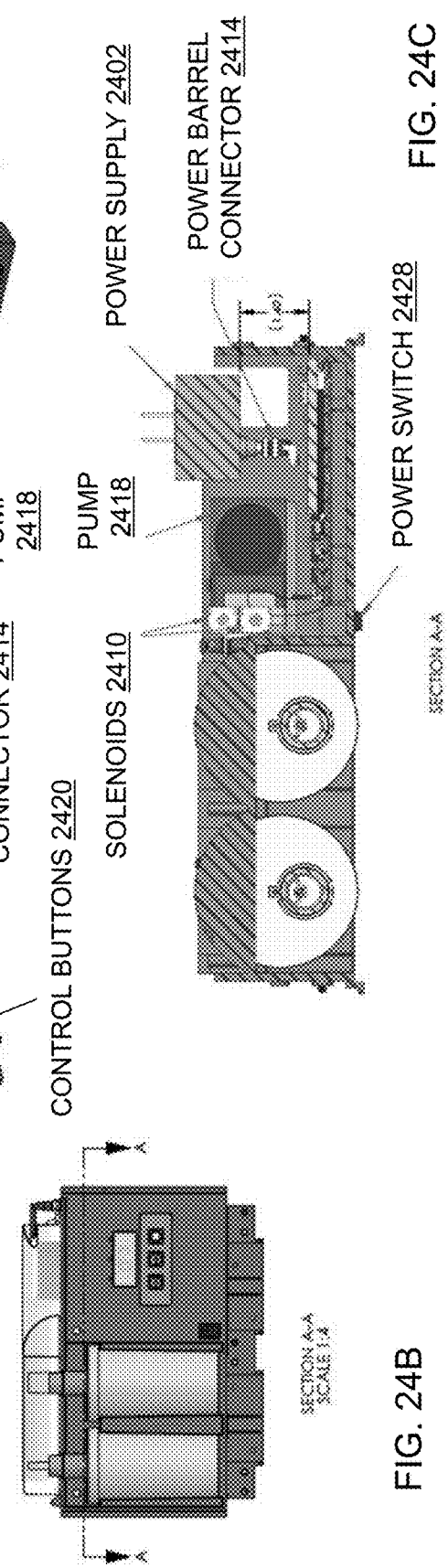

METHOD AND SYSTEM OF SENSOR FEEDBACK FOR A SCENT DIFFUSION DEVICE

CROSS-REFERENCE TO RELATED APPLICATIONS

This application claims the benefit of the following provisional applications, each of which is hereby incorporated by reference in its entirety:

U.S. Provisional Application No. 61/981,533, filed Apr. 18, 2014; and U.S. Provisional Application No. 62/045,989, filed Sep. 4, 2014.

BACKGROUND

Field

This disclosure relates generally to networked scent-diffusing devices and applications thereof.

Description of the Related Art

Of the five traditional senses, scent is strongly linked to memory. We recall what we see with poor accuracy after one month, while we remember what we smell with good accuracy after one year. This phenomenon is attributed to the intimate connection between the olfactory bulb and the brain's limbic system, often referred to as the "emotional brain."

Recognizing that the sense of smell is the most emotive of our five senses, it is a valuable element of brand communications and experiential marketing. Said differently, scent is very effective in delivering complete, multi-sensorial environments, since it is the most effective sense for creating lasting impressions.

Leading companies in industry sectors like hospitality, retail, gaming, real estate, health care, and senior living recognize the power of "scent marketing" and are seeking service solutions for their commercial establishments that are effective, safe, and easy to use. However, precise, consistent and measurable wide area dispersion of fragrances has been a significant challenge for early service providers in this emerging market. Their scent solutions provide widely varying experiences as the quality of scent impressions deteriorates over time and in changing environments.

Some current scent dispersion technologies provide stand-alone solutions that are managed locally by on-site employees or local subcontractors. Since the fragrance dispersed by these commercial scent devices is set manually and often changed over time, it is extremely difficult to ensure a consistent level of fragrance within brand standards across all locations. Common scent dispersion problems include undiagnosed malfunctioning of dispensers, incorrect dispenser settings, and device tampering, as well as scent "blindness" which occurs when employees who work within a scented location, become insensitive to a fragrance, leading them to make unwarranted changes to manual settings.

Given the great variability of conditions across local sites, it is very difficult to accurately predict the replacement dates for scent "refill cartridges" (elements often used to contain scent oils or other sources of fragrances in dispensing systems). As a result, there are many venues with no fragrance dispersion when cartridges run empty, while other venues experience wasted scent oil, increased expense, and disposal issues when cartridges are replaced prematurely.

Consequently, current scent solutions deployed in multi-site commercial businesses make it difficult for corporate brand executives, local site managers, and maintenance personnel to establish and maintain a consistent "acceptable" or "approved" scent concentration across their venues. Their inability to adequately control the olfactory portion of brand identity is a constant source of frustration, as site surveys indicate that a significant fraction of venues on any given day are not delivering the brand's targeted sensory experience.

There remains a need for a scent management system to provide wide area dispersion of a fragrance in accordance with a desired profile of fragrance in a manner that is consistent, precise, and controllable via a remote or a local network.

SUMMARY

Among other things, the present disclosure addresses these local "compliance" and brand management issues by enabling effective, centralized management of remotely deployed scent systems, including, without limitation, using microprocessor-controlled and networked diffusion devices that deliver data streams to a centralized network operations center (or NOC), which may be staffed by experienced operators using enterprise class software. Through this managed service, and with the help of precise local tools and enabling components, commercial businesses can ensure precise, wide-area fragrance delivery that is consistent with brand standards over time and across locations. A wide range of enabling components and technologies are disclosed herein for such a scent management system.

In one embodiment, there may be an electrical contact that may need to be made between the package and the device when the package is installed. An electrical feature on the package may contact an electrical feature on the device. If contact is made, the package contents may be dispensed. If contact is not made, the package contents may not be dispensed and an alert may be sent over the network.

In an aspect, a scent cartridge for a networked scent diffusion device may include a reservoir that holds a liquid and an atomizer head assembly, and an anti-tampering identifier associated with at least one of the reservoir and the atomizer head assembly, wherein the scent diffusion from the device is based on a state of the anti-tampering identifier. If the scent diffusion device does not recognize the anti-tampering identifier, an alert may be sent over a network, and scent may not be dispensed. If the cartridge is removed from the device, resulting in the device no longer recognizing the anti-tampering identifier, an alert is sent over a network. The state of the anti-tampering identifier is changed based on the proximity of the networked diffusion device to a specified network zone. In some embodiments, the atomizer head assembly includes an orifice plate containing a flow restriction orifice for passing compressed gas to be mixed with liquid before passing through an atomizing orifice. The anti-tampering identifier may be mechanical such as a dip switch, or the like. The anti-tampering identifier may be electronic, such as an RFID, bar/QSR code, and the like. The anti-tampering identifier may be a departure from a network zone of the networked scent diffusion device. The anti-tampering identifier may be an error or an unexpected reading of a liquid level sensor of the networked scent diffusion device. The anti-tampering identifier may be a disconnection of an electrical contact disposed on at least one of the reservoir and the atomizer head assembly from the networked scent diffusion device. The anti-tampering identifier may be an RFID tag associated with at least one of the reservoir and the atomizer head assembly. The atomizer head assembly may include an orifice plate containing a flow restriction orifice for passing compressed gas to be mixed with liquid before passing through an atomizing orifice. The anti-tampering identifier may be a mechanical feature of at least one of the reservoir and the atomizer head assembly. The anti-tampering identifier may relate to an electric field of at least one of the reservoir and the atomizer head assembly.

In an aspect, a scent cartridge for a networked scent diffusion device, may include a reservoir that holds a liquid and an atomizer head assembly, wherein the atomizer head assembly includes an orifice plate containing a flow restriction orifice for passing compressed gas to be mixed with liquid before passing through an atomizing orifice and an RFID tag associated with at least one of the reservoir and the atomizer head assembly, wherein when an RFID reader operably connected to the scent diffusion device recognizes the RFID tag, scent is dispensed from the cartridge.

In an aspect, a package for use with a scent diffusion device may include a reservoir that holds a liquid and an atomizer head assembly, wherein the reservoir is joined to the atomizer head assembly at a top edge of the reservoir and a tube for the transportation of the liquid in the reservoir, wherein the tube is joined to the atomizer head assembly on a first end while a second end of the tube extends below the surface of the liquid. A gas inlet passage of the atomizer head assembly may have one end in fluid communication with a compressed air source and a second end of the gas inlet passage in fluid communication with an orifice plate comprising a flow restriction orifice. A mixing chamber of the atomizer head assembly may be separated from the gas inlet passage by the orifice plate, the mixing chamber having a first wall opposite the orifice plate comprising an atomizing orifice and a second wall comprising an opening in fluid communication with the tube. An expansion chamber may be in fluid communication with the atomizing orifice and a baffle chamber, the baffle chamber having an outlet to a surrounding environment. A gas flowing into the gas inlet passage through the flow restriction orifice generates a relatively low pressure region in the mixing chamber that causes liquid from the reservoir to be drawn into the mixing chamber through the tube where it joins the flow path of the gas out of the restrictor orifice creating a mixture of gas and liquid which then becomes atomized when it passes through the atomizing orifice. The liquid reservoir may have a substantially cup shaped geometry. The top edge of the reservoir may be joined to the atomizer head assembly by one of an ultrasonic weld and/or a twist lock with o-ring seal.

In an aspect, an atomizing diffusion device may include a floating magnet disposed within a track inside at least one package with liquid for the diffusion device, wherein as a liquid level inside the package changes, the floating magnet moves substantially vertically along the track. The device may further include at least one Hall effect sensor or Hall effect switch disposed outside the liquid at a position to enable sensing the position of the floating magnet in the track. The device may also include a processor, operatively coupled to the Hall effect sensor or Hall effect switch, for generating a signal indicative of the sensed position of the floating magnet and a control instruction for a switch based on the signal and a switch, operatively coupled to the processor, that receives the control instruction from the processor, wherein the control instruction causes the diffusion device to switch from utilizing one package in the diffusion device to utilizing a different package in the diffusion device. The switch may be a solenoid switch. The device of claim may further include a scheduling facility that receives the signal and predicts when the package will be depleted of liquid or determines a package replenishment schedule. The device may further include a remote computer in communication with the processor for receiving the signal and generating an alert if the signal indicates a need for replacement of a package or when an unexpected signal is obtained. The processor may be adapted to send a signal indicating the switch to the different package in the diffusion device.

Referring now to FIG. 23, an embodiment of a cartridge with a Hall effect sensor for liquid level sensing is depicted. The upper portion of the drawing depicts the diffusion components including orifice assembly 2302, cartridge cap assembly 2304, and tubing 2308 to draw up fragrance oil. An ultrasonic weld 2310 attaches the cartridge cap 2304 to the cartridge cup 2314, wherein an O-ring 2312 is disposed between the two. In the cup 2314 there is a magnetic float 2320 that runs along a cartridge float guide 2318 as it rises and falls in accordance with a liquid level.

In an embodiment, an atomizing diffusion device may include at least two packages with liquid in fluid communication with a scent diffusion device, wherein the liquid level inside the package is exposed through at least one of a transparent wall and a transparent window of the package. At least one imaging sensor may be disposed outside the package in the diffusion device to image the liquid level in the package. A processor may be operatively coupled to the imaging sensor to generate a signal indicative of the liquid level and a control instruction for a switch based on the signal. The switch may be operatively coupled to the processor to receive the control instruction from the processor, wherein the control instruction causes the diffusion device to switch from utilizing one package in the diffusion device to utilizing a different package in the diffusion device. The processor may be adapted to send a signal indicating the switch to the different package in the diffusion device.

In an aspect, a method of managing scent in an environment may include disposing one or more scent diffusion devices within an environment, wherein the scent diffusion devices comprise a communications facility that enables transmitting signals to and receiving signals from a remote computer, receiving at least one scent parameter for scenting an environment at the remote computer, and controlling, via the remote computer, at least one of the scent diffusion devices to achieve the scent parameter. Controlling may include adjusting an operational parameter of the scent diffusion device in response to a sensed fragrance level in the environment.

In another aspect, a method of managing scent in an environment may include disposing one or more scent diffusion devices within an environment, wherein the scent diffusion devices include a communications facility that enables transmitting signals to and receiving signals from a remote computer. The method may further include disposing at least one sensor within the environment that transmits sensor data to the remote computer and receiving at least one scent parameter for scenting the environment at the remote computer. The method further includes controlling, via the remote computer, diffusion of a liquid from a source of the liquid that is in fluid communication with at least one of the scent diffusion devices to achieve the scent parameter.

In an aspect, a method relating to atomizing diffusion devices within an environment may include receiving at a computer, liquid level data from a plurality of remote atomizing diffusion devices wherein each diffusion device comprises a communications facility that enables transmitting signals to and receiving signals from a remote computer and at least one liquid level sensor, and based on the liquid level data, creating, via the remote computer, an electronic data structure characterizing the transformation of the remote diffusion devices, wherein the electronic data structure includes data specifying at least one of the production of scent fragrance, the procurement of scent fragrance, the management of scent inventory, the delivery of scent inventory, and causing the remote atomizing diffusion devices to implement the transformation. In embodiments, it is not diffusion of a liquid but diffusion of a gas. Controlling may include setting or adjusting an operation parameter of the scent diffusion device in response to the sensor data. The sensor data may relate to at least one of room volume, room geometry, room area, airflow, presence of odor-producing materials, presence of odor-sinking factors, lighting, air flow, altitude, traffic flow, occupancy detection (e.g. IR, camera, $CO_2$ sensor), proximity sensing, detected odor, fragrance level, scent concentration factor, temperature, humidity, time of day, season, weather event, information about an HVAC system, information about a building, detection of a VIP/specific individual entering the space, such as via a smartphone ping, and the like. The scent diffusion device includes at least one package containing a fragrance oil or at least two packages containing a fragrance oil. In embodiment, one of the scent diffusion devices is a master node and the other of the scent diffusion devices are slave nodes and receive control instructions from the computer through the master node. In this embodiment, each scent diffusion device can adjust its own control settings based on the activities of the other scent diffusion devices. The method may include configuring the scent diffusion devices so that a device duty cycle for one of scent diffusion devices does or does not occur simultaneously within proximity to another one of the scent diffusion devices. The scent parameter may relate to a brand management goal. The method may further include determining the total number of scent diffusion devices to dispose in the environment based on a room volume. The method may further include determining one or more locations to dispose the scent diffusion devices in the environment based on a room volume. The operation parameter may include at least one of a flow rate of the liquid, a duration of flow of the liquid, a variation in the flow rate of the liquid, an on/off status of the diffusion device, a package from which to diffuse the liquid, a switch to a different package from which to diffuse the liquid, and the like. The sensor data may relate to a distance from the scent diffusion device to a scent target location. The information about the HVAC system may include at least one of indoor temperature, outside air temperature, thermostat schedule, energy consumption, historical operation parameters, vacant room detection capability, occupied room detection capability, vent placement, duct size, fan speed, and maintenance status. The information about the building may include at least one of a number of people entering and exiting the building, planned use of a space, planned occupancy of a space, elevator use, escalator use, power use, lighting use, and plumbing use. The sensor data that relates to the fragrance level may be determined by at least one of measuring a proxy/tag dispersed with the fragrance, measuring an electrostatic charge, measuring a component of the fragrance, measuring an odorless marker diffused with the fragrance, measuring particles, and measuring a concentration of volatile organic compounds. Causing may include at least one of scheduling and coordination of resources to accomplish the transformation. The method may further include measuring a liquid level inside the plurality of remote atomizing diffusion devices using the liquid level sensor.

In an aspect, a method of managing scent in an environment may include disposing one or more scent diffusion devices within an environment, wherein the diffusion devices comprise a communications facility that enables transmitting signals to and receiving signals from a non-fragrance dispensing, wide-area network gateway device. The method may further include networking the network gateway device to the scent diffusion devices, wherein the network gateway device receives communication and control functions from a remote computer for distribution to the scent diffusion devices. At least one sensor disposed within the environment may transmit sensor data to the remote computer. At least one target value of a scent parameter for an environment may be received at the remote computer. The method may further include controlling, via the remote computer, diffusion of a liquid, from a source of the liquid in fluid communication with at least one of the scent diffusion devices, to achieve the target value of the scent parameter, wherein controlling includes setting or adjusting an operation parameter of one or more of the scent diffusion devices based on the sensor data. In embodiments, it is not diffusion of a liquid but diffusion of a gas. At least one of the scent diffusion devices receives control instructions from the remote computer and relays control instructions to at least one other scent diffusion device. The scent diffusion devices may relay control instructions in series, in a ring, in a mesh, in a star networking topology, and the like.

In an aspect, a method of managing scent in an environment may include disposing one or more scent diffusion devices within an environment, wherein the diffusion devices comprise a communications facility that enables transmitting signals to and receiving signals from a local area network control device and networking the local area network control device to each of the scent diffusion devices, wherein the local area network control device receives communications from and distributes control instructions to the scent diffusion devices. The method may further include disposing at least one sensor within the environment that transmits sensor data to the local area network control device, receiving at least one scent parameter for scenting an environment at the local area network control device, and controlling, via the local area network control device, the diffusion of a liquid, from a source of the liquid in fluid communication with at least one of the scent diffusion devices, to achieve the scent parameter, wherein controlling includes setting or adjusting an operation parameter of one or more of the scent diffusion devices in response to the sensor data. In embodiments, it is not diffusion of a liquid but diffusion of a gas. The local area network control device may include one or more of a computer or laptop with wireless local area network communication capability, a smart phone, a pad device or tablet computer with wireless local area network communication capability, a purpose built scent controller device with wireless local area network communication capability, a handheld device, a wall-mounted device, and the like.

In an aspect, a method of scent casting in an environment may include disposing a scent diffusion device within an environment, wherein the scent diffusion device comprises a communications facility that enables transmitting signals to and receiving signals from a remote computer, determining a distance from the scent diffusion device to a scent target location, receiving, at the remote computer, at least one scent parameter for the scent target location, and controlling, via the remote computer, the scent diffusion device to achieve the scent parameter, wherein controlling includes setting an operation parameter of the scent diffusion device based on the determined distance and the scent parameter. The method may further include disposing at least one sensor within the environment that transmits sensor data to the remote computer, and adjusting an operation parameter of the scent diffusion device in response to the sensor data. The sensor data may relate to at least one of room volume, room geometry, room area, airflow, presence of odor-producing materials, presence of odor-sinking factors, lighting, air flow, altitude, traffic flow, occupancy detection (IR, camera, CO2 sensor), proximity sensing, detected odor, fragrance level, temperature, humidity, time of day, season, weather event, and detection of a VIP/specific individual entering the space (via smartphone ping or the like). The method may further include adjusting an operation parameter of the scent diffusion device in response to an HVAC tonnage.

In an aspect, a method may include sampling the air in an environment to determine a fragrance level according to an automated sampling program, providing the fragrance level as feedback to a network of scent diffusion devices, and adjusting an operation parameter of the scent diffusion devices in response to the feedback, wherein adjusting enables the continued generation of a consistent scent profile in the environment. Determining may involve measuring a proxy/tag dispersed with the fragrance or an electrostatic charge. Adjusting may be by selection/adjustment of one or more of a plurality of available scent modifiers onboard one or more networked scent diffusion devices. A user may adjust an overall level of fragrance desired in the space and a scent diffusion device controller may determine the adjustment required for the one or more devices. Adjusting may involve a master diffusion unit of the network of scent diffusion devices adjusting its own output level and the output level of its slaves upward or downward, proportionately based on the adjusted operation parameter. The sampling may indicate the presence of a malodor and the operation parameter may be adjusted to provide a scent neutralization. Sampling may indicate the presence of a malodor and the operation parameter is adjusted to terminate diffusion of the scent.

In an aspect, a method of managing scent in an environment may include disposing one or more scent diffusion devices within an environment, wherein the diffusion devices include a communications facility that enables transmitting signals to and receiving signals from a remote computer, taking information about an HVAC system in the environment to the remote computer, taking at least one scent parameter for scenting an environment at the remote computer, and controlling, via the remote computer, at least one of the scent diffusion devices to achieve the scent parameter, wherein controlling includes setting or adjusting an operation parameter of the scent diffusion device based on the information about the HVAC system. The information may be a tonnage of the HVAC system. Taking information about an HVAC system may be done via manual entry, as a feed or data dump from an building automation system, as a feed or data dump from the HVAC system, as a feed or data dump from a local processor, from sensors such as a flow sensor, and the like. Other information about the HVAC system that may be used in managing scent in an environment include indoor temperature, outside air temperature, thermostat schedule, energy consumption, historical operation parameters, vacant room detection capability, occupied room detection capability, vent placement, duct size, fan speed, flow, and maintenance status.

In an aspect, a method for managing scent in an environment may include disposing a plurality of scent diffusion devices within the environment, wherein the scent diffusion devices comprise a communications facility that enables transmitting signals to and receiving signals from a remote computer, monitoring the environment for an indicator that a service is being delivered, and when the indicator is received, controlling, via the remote computer, at least one of the plurality of scent diffusion devices to emit a scent that is intended to be a companion to the service.

In an aspect, a method of managing scent in an environment may include disposing at least one scent diffusion device within an environment, wherein the at least one scent diffusion device comprises a communications facility that enables transmitting signals to and receiving signals from a remote computer, disposing at least one sensor within the environment that transmits sensor data to the remote computer, monitoring an environment via the at least one sensor for an indicator that a service is being delivered, and when the indicator is received, as determined by the sensor data, controlling, via the remote computer, diffusion of a liquid from a source of the liquid in fluid communication with the at least one scent diffusion device to emit a scent that is intended to be a companion to the service, wherein controlling includes setting or adjusting an operation parameter of the at least one scent diffusion device. In embodiments, it is not diffusion of a liquid but diffusion of a gas.

In an aspect, a method of implementing a computer-implemented automated scent environment design and modeling system may include defining objects that represent a component of an environment being modeled, wherein at least one parameter of at least one of the objects impacts the diffusion of scent within the environment, assembling an environment model utilizing the objects, inputting data to the environment model related to one or more sensors in the environment, using at least one data structure representing at least one parameter of a scent diffusion device, and displaying information about diffusion of scent in the environment based on the environment model, the defined objects, and at least one parameter of the at least one scent diffusion device. Determining a placement of one or more scent diffusion devices in the environment may be based on the one or more scent impression goals, the environment model and the data. The objects may be represented in a three-dimensional relationship. The method may further include allowing a user to define one or more scent impression goals for the environment. The method may further include recommending a placement of one or more scent diffusion devices in the environment based on the one or more scent impression goals and the environment model. The method may further include inputting data to the environment model related to one or more sensors in the environment. The information may be displayed in a graphical user interface that shows the physical dimensions of the environment and the objects in the environment. The display may be a 3D display. The display may be a 3D overhead view of the environment. The object may be at least one of a window, a skylight, a wall, a floor, a door, a ceiling, a fireplace, furniture, plants, an HVAC system and its elements, fans, hoods, vents, ducts, conduits, a fragrance-free zone, a fragrance zone, a consumer pathway, and the like. The data may relate to at least one of room volume, room geometry, airflow, HVAC systems, presence of odor-producing materials, presence of odor-sinking factors, lighting, temperature, humidity, altitude, traffic flow, occupancy, time of day, and the like. The objects may be customized based upon the inputted scent impression goal. For example, furniture or plants may be removed if they are found to interfere with a scent plume. Assembling the environment model may include using a drag-and-drop interface to place the objects in the three-dimensional relationship. The scent impression goal may include planning for fragrance zones and fragrance-free zones. The environment model may colorimetrically depict scent plumes/zones and airflow/diffusion areas. The environment model may depict consumer pathways (optionally with timing) to ensure multiple exposures with a fragrance-free zone in between. The method may further include suggesting a profile of fragrances that would be effective in the environment given data relating to a scent neutralizing profile of the environment. An effective fragrance may be identified based on one or more of a particle size and a scent concentration factor.

In an aspect, a user interface produced by computing equipment executing program code stored in a non-transitory storage medium may be an interface for a scent design and modeling system. The user interface may include a drag-and-drop interface to place objects that represent a component of an environment being modeled in a relationship to one another to form an environment model, wherein at least one parameter of at least one of the objects impacts the diffusion of scent within the environment, and a processor that models the scent-impacting parameters of the objects in the environment model and determines at least one of a placement in the environment for and a scent-diffusing parameter of one or more scent diffusion devices. The environment model further includes one or more scent impression goals. The processor further models the scent impression goals for the environment model to determine at least one of a placement in the environment for and a scent-diffusing parameter of one or more scent diffusion devices. The environment model further includes data related to one or more sensors in the environment. The environment model may be displayed in a graphical user interface that shows the physical dimensions of the environment and the objects in the environment. The display may be a 3D display. The display may be a 3D overhead view of the environment. The drag and drop interface enables dragging and dropping scent zones based on an HVAC/building blueprint to optimize scent vectors/scent device settings. The object may be at least one of a window, a skylight, a wall, a floor, a door, a ceiling, a fireplace, furniture, plants, an HVAC system and its elements, fans, hoods, vents, ducts, conduits, a fragrance-free zone, a fragrance zone, a consumer pathway, and the like. The data may relate to at least one of room volume, room geometry, airflow, HVAC systems, presence of odor-producing materials, presence of odor-sinking factors, lighting, temperature, humidity, altitude, traffic flow, occupancy, time of day, and the like. The objects can be customized based upon the inputted scent impression goal. The relationship may be a three-dimensional relationship. The object may be a source of a malodor In an aspect, a method may include calculating a metric for a brand impression, wherein the brand impression metric is based on exposure to a scent delivered by one or more managed, networked scent diffusion devices. The metric may be based on at least one of number of exposures, duration of exposures, and location of exposures. Determining may include performing matched panel testing, A/B testing, or controlled testing of a population exposed to the scent. Determining may include obtaining feedback from a population exposed to the scent. The feedback may be through a survey delivered from the networked scent diffusion device.

In an aspect, a method may include determining sales lift by comparing the purchase behavior of a group of participants exposed to a scent in a retail environment with a group of participants in a comparable retail environment who were not exposed to the scent, wherein the scent exposure is due to one or more networked scent diffuser devices in the retail environment under the control of a remote computer.

In an embodiment, a networked scent diffuser device may serve as a commercial gateway for a consumer environment utilizing one or more integrated sensors to gather information from the consumer environment. The networked scent diffusion device may include a communications facility that receives control signals from a network operations center, the control signals for controlling a scent diffusion from the scent diffusion device in accordance with a scent impression goal and one or more integrated sensors to gather information from a consumer environment in which the scent diffusion device is deployed. The sensor may be a traffic/occupancy sensor.

The networked scent diffusion device may include a first communications facility that receives control signals from a network operations center, the control signals for controlling a scent diffusion from the scent diffusion device in accordance with a scent impression goal, and a second communications facility to communicate data with a mobile device in the consumer environment. The communication may relate to a scent being diffused by the device. The commercial gateway allows a consumer in the consumer environment to control the scent diffuser device. The device may be controlled by a user in the consumer environment through one of the first or second communications facility. The communication may be an offer.

In an aspect, a method may include receiving at a computer at least one target value of a scent parameter for an environment 1602, receiving at the computer a sensed parameter of the environment 1604, and controlling, via the computer, diffusion of a liquid from a source of the liquid in fluid communication with at least one scent diffusion device to achieve the target value of the scent parameter 1608, wherein controlling includes setting or adjusting an operation parameter of the at least one scent diffusion device in response to the sensed parameter. One of the at least one scent diffusion devices may be a master node and the other scent diffusion devices are slave nodes and receive control instructions from the remote computer through the master node. At least one of the scent diffusion devices may receive control instructions from the remote computer and relays control instructions to at least one other scent diffusion device. The scent parameter may relate to a brand management goal. The operation parameter may include at least one of a flow rate of the liquid, a duration of flow of the liquid, a variation in the flow rate of the liquid, an on/off status of the diffusion device, a package from which to diffuse the liquid, and a switch to a different package from which to diffuse the liquid.

In an aspect, a method of managing scent in an environment may include taking an electronic data structure characterizing the transformation of at least one diffusion device disposed within an environment, wherein the electronic data structure includes data regarding a sensed parameter of the environment 1702, accessing at the remote computer, a target value of a scent parameter 1704, and providing a service plan for the at least one diffusion device based on the electronic data structure and the target value of the scent parameter 1708. The sensed parameter may relate to at least one of room volume, room geometry, room area, airflow, presence of odor-producing materials, presence of odor-sinking factors, lighting, air flow, altitude, traffic flow, occupancy detection (IR, camera, $CO_2$ sensor), proximity sensing, detected odor, fragrance level, temperature, humidity, time of day, season, weather event, information about an HVAC system, information about a building, and detection of a VIP/specific individual entering the space (via smartphone ping). Servicing may include configuring the at least one scent diffusion device so that a device duty cycle does or does not occur simultaneously within proximity to another scent diffusion device. The scent parameter may relate to a brand management goal. The operation parameter may include at least one of a flow rate of the liquid, a duration of flow of the liquid, a variation in the flow rate of the liquid, an on/off status of the diffusion device, a package from which to diffuse the liquid, and a switch to a different package from which to diffuse the liquid.

In an aspect, a method of managing scent in an environment may include disposing at least one sensor within the environment that transmits sensor data to the remote computer 1802, and disposing at least one scent diffusion device within an environment, wherein the at least one scent diffusion device comprises a communications facility that enables receiving a signal from a remote computer, wherein the signal is a setting or an adjusting of an operation parameter of the at least one scent diffusion device in response to the sensor data to achieve a target value of a scent parameter 1804. The method may further include determining the total number of scent diffusion devices to dispose in the environment based on a room volume or determining one or more locations to dispose the scent diffusion devices in the environment based on a room volume. The method may further include configuring the at least one scent diffusion device so that a device duty cycle does or does not occur simultaneously within proximity to another scent diffusion device. The sensed parameter may relate to a distance from the scent diffusion device to a scent target location.

In an aspect, a method of managing scent in an environment may include creating, via a remote computer, an electronic data structure characterizing the transformation of at least one remote diffusion device 1902, wherein the electronic data structure includes data regarding a sensed parameter of an environment and at least one target value of a scent parameter for the environment, and initiating control, via the remote computer, of diffusion of a liquid from a source of the liquid in fluid communication with the at least one scent diffusion device in accordance with the electronic data structure to achieve the target value of the scent parameter in response to the sensed parameter 1904. The sensed parameter data may relate to at least one of room volume, room geometry, room area, airflow, presence of odor-producing materials, presence of odor-sinking factors, lighting, air flow, altitude, traffic flow, occupancy detection (IR, camera, CO2 sensor), proximity sensing, detected odor, fragrance level, temperature, humidity, time of day, season, weather event, information about an HVAC system, information about a building, and detection of a VIP/specific individual entering the space (via smartphone ping). The scent diffusion device may include at least two packages containing fragrance oil. The scent parameter may relate to a brand management goal. The sensed parameter that relates to fragrance level may be determined by at least one of measuring a proxy/tag dispersed with the fragrance, measuring an electrostatic charge, measuring a component of the fragrance, measuring an odorless marker diffused with the fragrance, measuring particles, and measuring a concentration of volatile organic compounds.

These and other systems, methods, objects, features, and advantages of the present disclosure will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The disclosure and the following detailed description of certain embodiments thereof may be understood by reference to the following figures:

FIG. 9 depicts a method relating to atomizing diffusion devices.

FIG. 19 depicts a method relating to atomizing diffusion devices.

FIGS. 24 A-D depict embodiments of a diffusion device.

DETAILED DESCRIPTION

Figure 1:
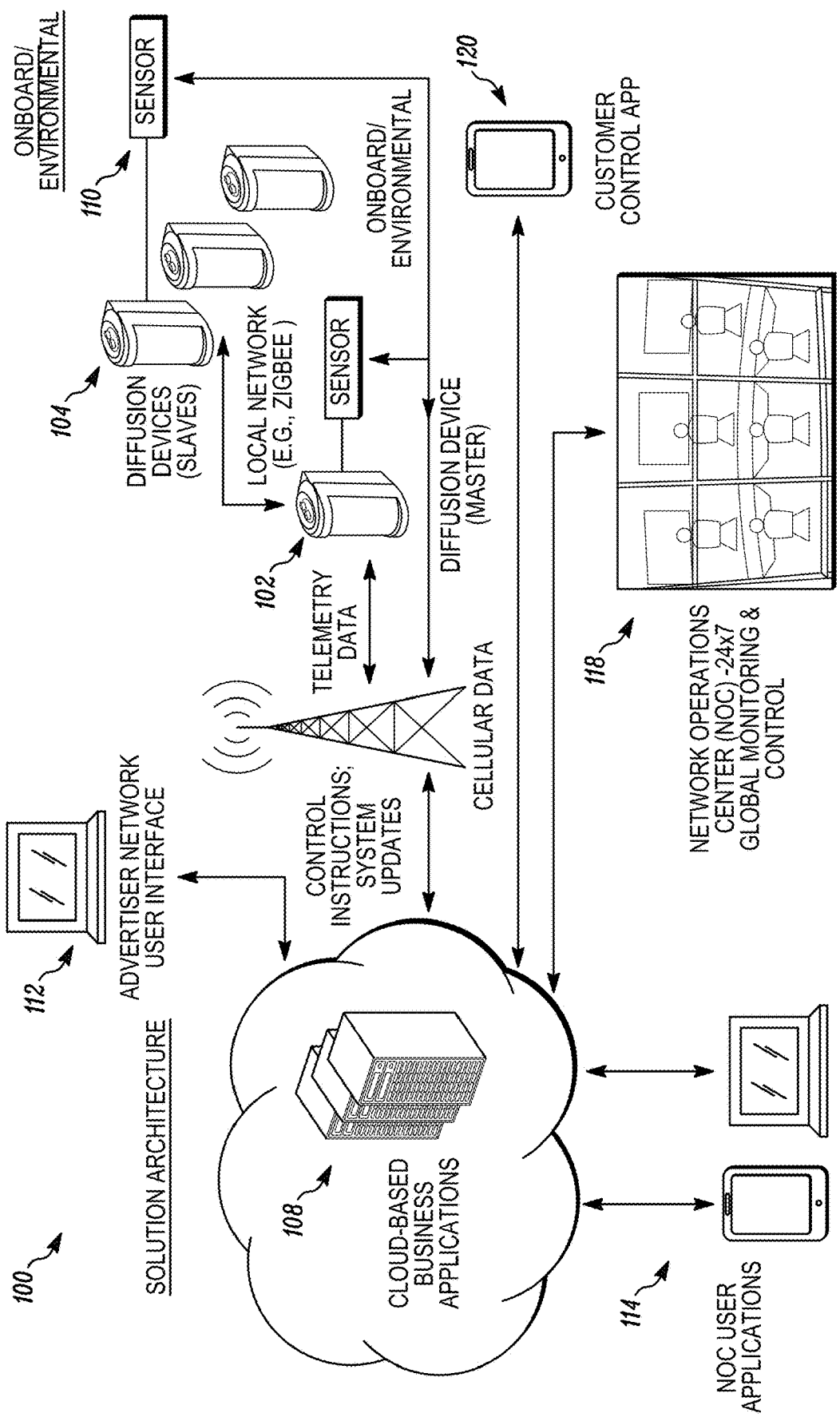
FIG. 1 depicts an exemplary architecture for a scent management system.

In an aspect, the scent management system provides businesses with a managed service for precise, wide-area fragrance delivery directed at using scent to deliver memorable brand impressions and exceptional customer experiences. By building intelligence into equipment deployed on customers' premises, and by managing the equipment using a global network and a centralized set of software applications, the scent management system provides unprecedented quality and control of a remotely managed scent service for customers and ensures that scent management services are efficacious, reliable and consistent. Such a scent management system is capable of ensuring a defined level of quality based on intelligence built into the system, from the diffuser device to the centrally managed network operations center (NOC), which monitors device performance across all customers and across all devices for each customer. The scent management system is capable of delivering identical scent impressions across all locations, if so desired, through measured fragrance output and in-space metering for precise concentration. The scent management system provides a managed scent service that delivers a consistent brand impression through the precise, dynamic control of a network of scent diffusion devices in either a remote or a local fashion. Features of the scent management system, such as two-way communication with networked scent diffusion devices to receive data from the devices and to control the devices remotely, coupled with features of the devices, including sensors and/or programming to switch between installed packages of fragrance, enables the scent management system to be deployed as part of multiple service offerings, including self-service and full-service models of operation. In a self-service model, users may select settings for the devices and receive indications regarding replenishment, such as through a customer application. In a full-service model, settings may be selected and modified by the NOC not just for one location but across as many locations as required to conform to brand management goals, replenishment alerts may go to the NOC which is then responsible for managing the replenishment, and the like. Communication with the NOC allows users the confidence that the devices in a space are operating as desired without having to be hands-on with the devices or with a control application for the device. Of course, the flexibility of the scent management system enables users (such as non-NOC staff) to utilize control applications to monitor and control the scent diffusion devices as desired. The system enables intelligent, deterministic delegation of roles, authorities, and permissions across the network of diffusers to preserve brand integrity. Users can control roles, authorities, and permissions across a hierarchical organization (e.g. parent company/corporate, franchise, location) to enable diffusion device control on a local level, such as on a location basis, or at a corporate level, and the like.

The scent management system may be useful not just for scent branding and delivering consistent scent impressions, but also for odor mitigation, odor neutralization, product advertising, aromatherapy/stress reduction, and the like. Other functional benefits will be described herein.

The scent management system may include one or more diffusion devices. Each diffusion device may contain a processor, such as a microcontroller, capable of reporting information (telemetry data) about diffuser status via the Internet to one or more Cloud-based business applications. The microcontroller may be capable of controlling the units autonomously, based on control instructions sent by the business applications. The business applications store historical data about the diffusion devices, which enables reporting on this data and mining of the data in order to improve scent management services. A NOC may be utilized to monitor the health of the end-user diffusion devices, and may react to alerts by adjusting the settings of the diffusion devices, or by creating a work order (e.g. to roll a truck, e-mail an on-site contact, etc.) in order to address a service issue or replenishment issue. Alternatively, devices may be self-serve, non-NOC managed. In embodiments, the networked diffusion devices form part of an Internet of Things.

In an embodiment, the scent management system may include: a diffusion device with built-in intelligence enabled by a built-in microcontroller module, plus communication abilities enabled by wireless local and wide area network communication modules; and diffusion device network configurations that support the intelligent management of fragrance dispersion, either locally within a fragranced environment, or remotely by one or more centralized or distributed network operations center(s) (NOCs) staffed by scent system administrators. The scent management system includes business processes enabled by the diffusion devices, deployed within defined scent dispersion network configurations. Throughout this specification, the terms "scent device", "scent dispersion device", "diffuser device", "diffuser", "scent diffusion device", or "scent diffuser device" may be used interchangeably with each other and with the term "diffusion device", except where context indicates otherwise. It should be understood that the use of scented liquids in the diffusion device is exemplary of one of the kinds of liquids that may be used in the scent management system. Indeed, scent neutralization liquids, disinfectant, cleansing or other liquids may also be used in the diffusion devices. Throughout this specification, the terms "cartridge", "package", and "reservoir" are used interchangeably with each other, except where context indicates otherwise. Various aspects of the scent management system are described herein. Further, it should be understood that the devices may work to dispense any liquid, such as in a gas or vapor colloidal mixture. FIG. 1 depicts an exemplary architecture 100 for a scent management system. In this embodiment, a master diffusion device 102 is in communication with one or more slave diffusion devices 104 and a server 108, such as a cloud server running cloud-based business applications. In this embodiment, the device 102 communicates with the server 108 to receive control instructions, systems updates, and the like from and to transmit telemetry data and the like to a NOC 118. Communication may be through a cellular connection. The devices 102, 104 may be in communication with environmental, or have onboard, sensors 110. NOC user devices 114 may communicate through the server 108 with the devices 102, 104. A customer control device 120 may be used to control the devices 102, 104 through the server 108. An advertiser network user interface 112 may be in communication with the server 108.

In an embodiment, the scent diffusion device may include a cartridge-based removable repository for fragrance oil or other liquid to be diffused, and a diffuser that atomizes the fragrance oil into particles to deliver targeted and controllable concentration levels of the fragrance oil or liquid. The particles may be variously sized, such as micro-droplets, or large or small aerosol particles. In embodiments, the diffuser results in minimal fallout of particles. The diffuser includes at least one of a micro-droplet generator, an atomizer, a nebulizer, a vaporizer, an evaporative wick, a saturated solid, and the like.

In an embodiment, the scent diffusion device may include a solid scent medium cartridge that heat energy, such as from a coil, light bulb, candle, heated blower, convective heat source, or the like, to heat the scent medium in the cartridge, while a fan blows through the medium to distribute fragrance. Controlling the fragrance diffusion remotely may involve controlling at least one of the fan or the heat source.

In embodiments, such as where a scent diffusion device may include a wick or other fixed or solid medium, diffusion rate/efficiency or wicking rate/efficiency may be adjusted over time or periodically, such as by adjusting an aspect or parameter of the operation of a fan. For example, the amount of liquid available for diffusion may decrease over time as the device operates. In some embodiments, the amount of liquid in the device may decrease at a predictable rate, such as at an exponential rate that can be predicted based on a model, such as a physical or chemical model. As the amount of available liquid decreases in the device, it may become more difficult to induce diffusion of the remaining liquid from the device. This may be due in part to changes in an aspect or parameter of a fixed medium that is used to aid diffusion over time. For example, a wick may dry up, a solid fragrance cake may dehydrate, or the like. By controlling a parameter of a device that is used to promote diffusion, such as the speed of a fan, adjustments may be made to address changes in diffusion characteristics. For example, the fan speed in the diffusion device throughout its operation may be adjusted such that it runs slower when a new cartridge of liquid or other fixed medium is placed in the device, and as a result, the wick or other fixed medium may dry out more slowly. Then, as the device operates and the characteristics of the wick or other solid medium change, the fan may be sped up to obtain a relatively consistent level of diffusion of the liquid from the cartridge or other fixed medium. In some embodiments, the operation of the fan may approximate an elliptoid curve, an exponential curve, or other function suitable to obtain a continuous level of diffusion of the liquid. In embodiments, such as where the liquid is a fragrance oil, controlling the fan to obtain a continuous level of diffusion of the fragrance oil may result in a substantially stable intensity of fragrance over time.

In an embodiment, a piezoelectric device may be used in the scent diffusion device to cause a vibration in the package, such as via ultrasonic surface wave effects, or through the use of microscopically perforated vibrating mesh (VMT). Such vibration may cause an oscillating motion and pressure in the liquid within the package and effect atomization of the liquid. The piezoelectric device may be remotely managed to control fragrance levels.

Other devices may be used in the system for scent diffusion, such as those including atomizers with hydraulic spray nozzles, liquid-liquid impinging atomizers, air-liquid impinging atomizers, airblast atomizers, prefilming atomizers, high voltage electrospray, and the like.

The diffusion device may further include a pump, to enable the venturi effect or otherwise draw the liquid from within the package to enable diffusion, with a controllable duty cycle. The diffusion device may include a fan that aids in distributing the particles. The fan may be low noise, such as by use of a low-noise fan or noise cancelling technology. The diffusion device enables uniform dispersion of vaporized fragrance oil throughout an environment using dispersion technologies that require minimal heat. Such technologies allow fragrance integrity to be sustained over time.

In some embodiments, the pump may be a conventional air pump or a speed control air pump. With a conventional air pump, the amount of scent output may be controlled using a duty cycle, such as, for example, a duty cycle of "on" for 2 minutes and "off" for 4 minutes to provide a 33% duty cycle. Given the ability to remotely control pump operation in networked scent diffusion devices, the voltage driving the pump may be increased or decreased remotely, such as in a range of roughly +/−20% from a 10V standard, or from 8 V to 12 V. Controlling the voltage driving the pump enables remote control of the diffusion rate of the device, independent of the voltage range and independent of duty cycle. At a given duty cycle, output can be attenuated or augmented by simply altering the voltage for the pump. For example, for multiple diffusers deployed in an environment, assuming that all of the diffusers are set with the same duty cycle, the voltage driving diffusers deployed in smaller spaces of the environment may be lowered to attenuate output while the voltage driving diffusers deployed in larger spaces of the environment may be raised to augment output. In this example, a duty cycle including an "on" portion of 1 minute at a low speed setting might put out X micrograms per hour, while the same duty cycle portion of "on" for 1 minute at a high speed setting may put out 3X micrograms per hour. Voltage control of the pump enables volumetric control of the device running on a continuous or nearly continuous basis.

Figure 22:
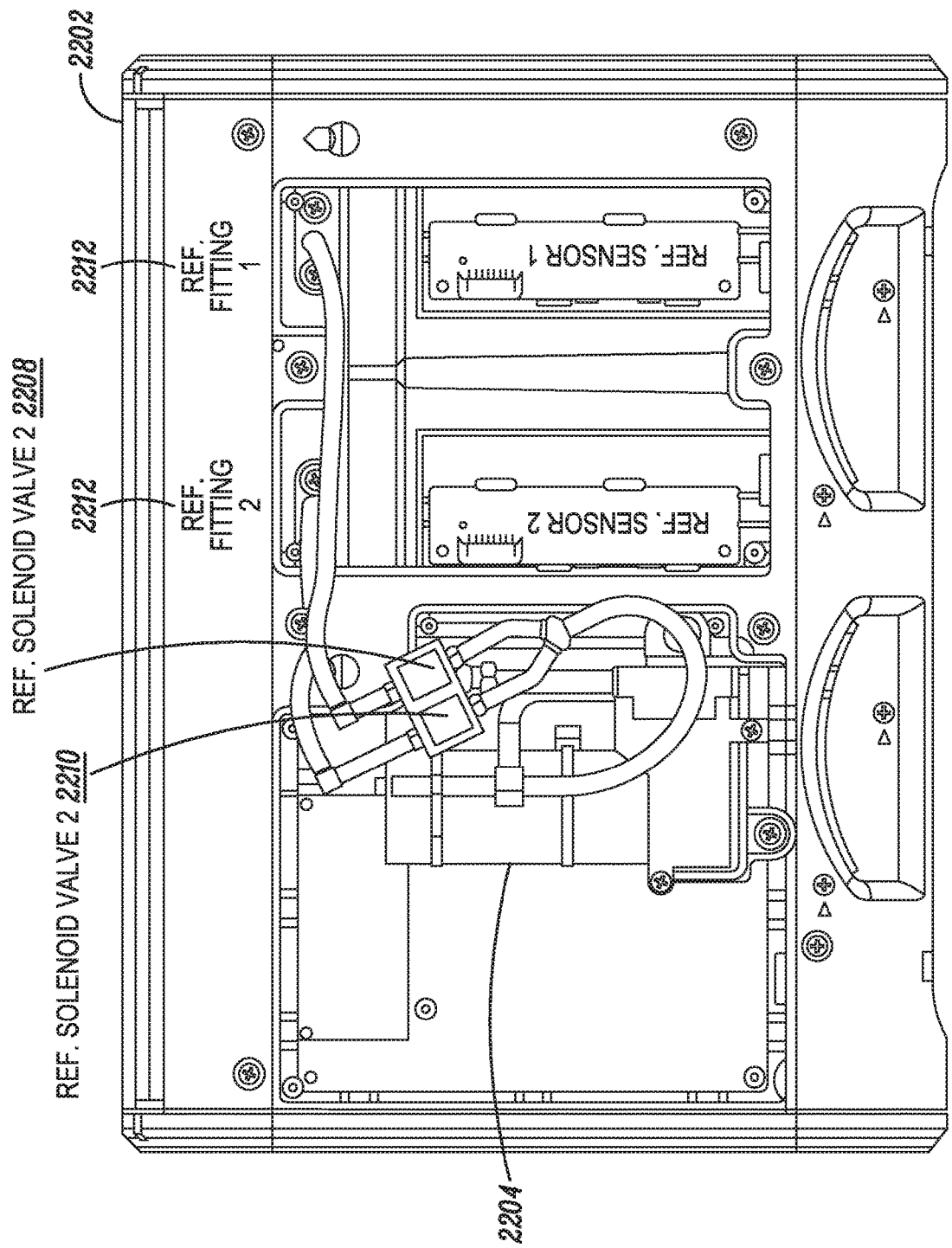
FIG. 22 depicts a diffusion device showing a pump assembly and solenoid valves.
Figure 23:
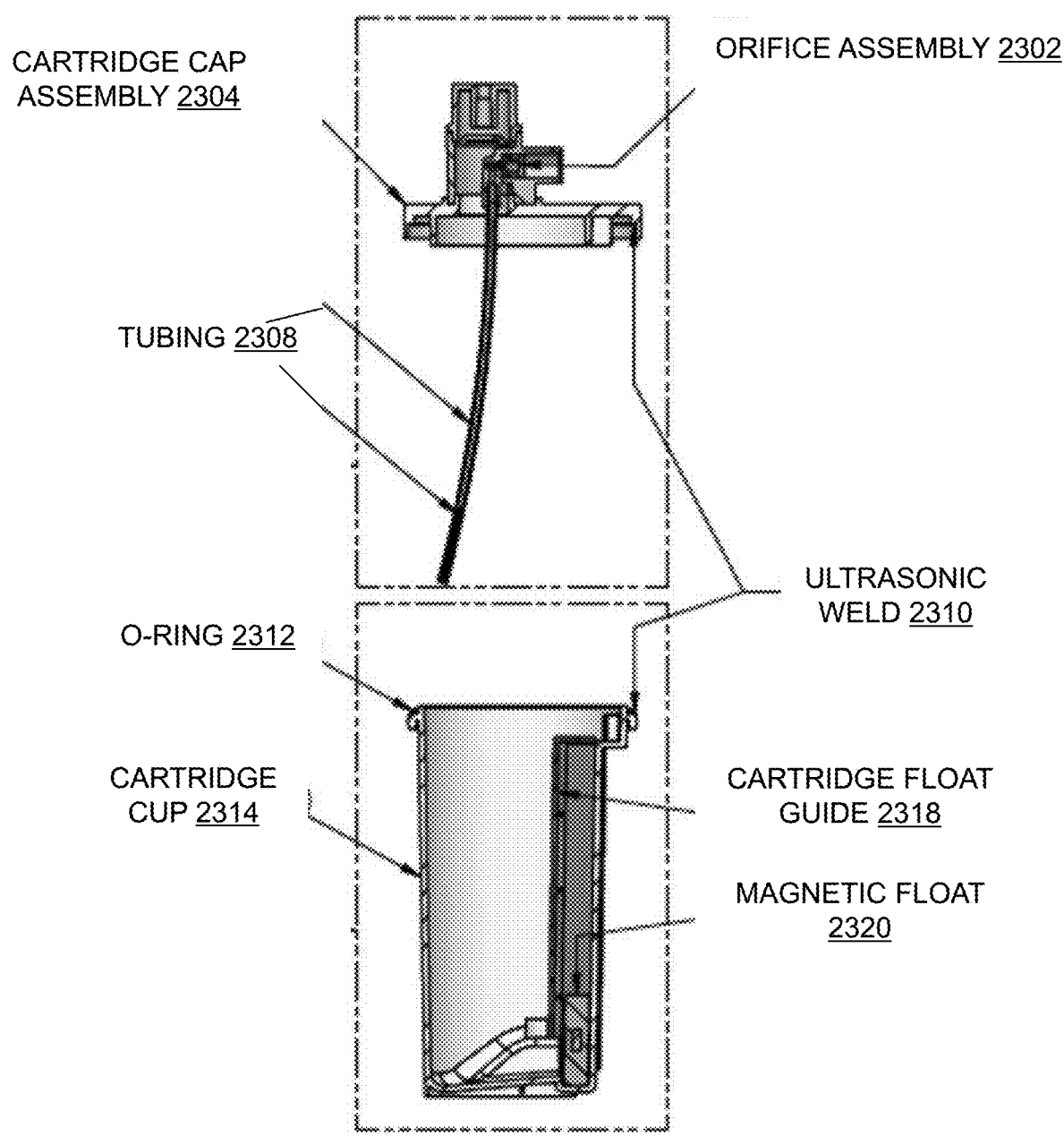
FIG. 23 depicts an embodiment of a cartridge.

Referring now to FIG. 22, an embodiment of a diffusion device is depicted. In this view, the housing 2202 contains a pump assembly 2204 that pumps liquid up out of the reservoir(s) through tubes attached to the pump and assembled into fittings 2212. One or more valves, such as solenoid valves 2208, 2210, are placed in line in the tubes to turn pumping on and off.

The diffusion device may include a programmable microcontroller module with a memory (fixed or removable) for controlling device functionality, such as control of volume, duty cycle, schedule settings, and the like. The diffusion device may include a wireless local area network module capable of communicating with other devices within a physical location via radio frequency communications including IEEE standards (such as, WiFi, Zigbee, Bluetooth, etc.) Communications protocols that may be used by the diffusion device include one or more of Zigbee, MiFi, MiWi, DMX, ANT, Z-Wave, Insteon, JenNet-IP, X10, mesh network, visible light, ultrasound, infrared light, IP version 6 (IPv6), such as IPv6 over Low Power Wireless Personal Area Networks (6LoWPAN), and the Neighborhood Exchange Protocol. The diffusion devices may form a machine-to-machine network. The diffusion device may include a removable wireless wide area network (WWAN) module capable of electronic communications with one or more remote Network Operations Center(s) via, for example, a telecommunication cellular network. References to a "Network Operations Center" or "NOC" throughout this disclosure should be understood to encompass a single, centralized center, or a set of multiple distributed centers. In embodiments, the diffusion device may include communications technology for wired installations. Telemetry data, such as fragrance-level replenishment alert, may be delivered over the communications network. Device firmware may be upgradable via the network.

In an embodiment, on the motherboard of the device, connectors may be adapted to configure the communications module readily or to render the communications module modular, such that it may be swapped in and out readily. For example, the device may be manufactured such that at a distributor, retailer, customer, or other downstream site, a communications module may be installed or swapped. For example, the device may be shipped from the manufacturer to the distributor with a cellular communications module installed, but upon receipt, a need for WiFi- and Bluetooth-enabled devices may emerge. The distributor may be able to open the devices and swap out the cellular communications module for the WiFi-enabled and/or Bluetooth-enabled module. In some examples, the devices may be able to accommodate a plurality of communications protocols such that in this example, the distributor need only to add in the WiFi and Bluetooth modules to the existing cellular module. In other embodiments, the communications module may be embodied with firmware, such that capabilities may be modified by a firmware update, such as delivered over a cellular network via a cellular networking communications protocol, over the Internet or other IP-based network, or the like. In embodiments the communications module may be embodied in or may use a field programmable gate array (FPGA), such that it may be re-programmed in the field to meet changing requirements.

The diffusion device may feature "plug and play" ease of installation, with AC or DC power, auto-configuration and NOC "check-in." Overall, the diffusion device may be light in weight, so the device can hang from a track fixture or wall, such as 5 lbs. per device.

The diffusion device may include a manual programming interface (e.g. user interface, screen, button, dial, slider, touch pad, keyboard, or the like) that allows an individual to manually establish and confirm device settings. In embodiments, the diffusion device includes a signal that alerts a user of a device state. The state may relate to a sensed liquid level. The signal may be at least one of a light 1028, a color indicator, a message on a text screen, a sound, and the like.

In an embodiment, a scent diffusion device may include a processor that monitors the scent diffusion device and generates a status, and a user interface that provides an alert based on the status, wherein the alert triggers an event. The status may be a clog and the event may be the scheduling of maintenance. The status may be a need for replenishment and the event may be at least one of the scheduling of replenishment and ordering of additional scent. The status may be a tampering and the event may be turning off the device. The status may be at least one of a clog, a need for replenishment, a tampering, an overheating, a loss of power, an operation error, and a damage. The alert may be at least one of a light 1028, a color indicator, a message, a pop-up, a sound, an e-mail, a text message, and an SMS/MMS.

In an embodiment, one form of the device may operate as a point-of-use scent disperser, installed within targeted fragrance areas. In an embodiment, another form of the diffusion device may be integrated into the heating/ventilation/air conditioning system of a venue, with fragrance dispersion occurring through the HVAC ductwork or other ventilation system.

In an embodiment, the diffusion device may be embodied in the form factor of a flameless LED candle.

In an embodiment, the diffusion device may include a tamper-proof closure. The tamper-proof closure may be at least one of a physical key, a software-based key, a biometric key, a retinal scanner, and the like. Physical features of the package may also make it difficult to be tampered with, such as by including at least one of a sonic-welding, a spin welding, a bayonet lock, and the like. On-board sensors may also work as an anti-tampering mechanism if contact with the sensors are lost while power is still sensed or utilized by the device.

The package for the diffusion device may include physical features for anti-tampering that prevent the package from operating properly in a device not configured to accept the package. For example, the package may include an RFID tag 1208 for identification and the RFID tag must be read correctly or the diffusion device will not function. Reading the RFID tag may be done on-board the device by an integrated RFID reader or may be done with a separate RFID reader, such as upon installation of the package or during a routine inspection. In another example, the package may include another identification tag, such as a bar code 1204 or QR code 1202, which may be imaged by on-board imaging or a separate imager. The images may be transmitted to the NOC for analysis and approval or storage. In one embodiment, there may be an electrical contact that may need to be made between the package and the device when the package is installed. An electrical feature (not shown) on the package may contact an electrical feature (not shown) on the device, or mating mechanical features (not shown) may be disposed on the package and device. If contact is made, the package contents may be dispensed. If contact is not made, the package contents may not be dispensed and an alert may be sent over the network.

An alert may be sent over a network if the package is removed, such as if the package is removed early (e.g. a liquid level sensor indicates sufficient liquid remaining), removed in spite of general instructions (e.g. removed without a work order, removed by a non-technician), and the like.

In an aspect, a scent cartridge for a networked scent diffusion device may include a reservoir that holds a liquid and an atomizer head assembly, wherein the atomizer head assembly includes an orifice plate containing a flow restriction orifice for passing compressed gas to be mixed with liquid before passing through an atomizing orifice, and an anti-tampering identifier associated with at least one of the reservoir and the atomizer head assembly, wherein the scent diffusion from the device is based on the condition of the anti-tampering identifier. When the scent diffusion device does not recognize the anti-tampering identifier, an alert may be sent over a network, and scent may not be dispensed. If the cartridge is removed from the device based on the device no longer recognizing the anti-tampering identifier, an alert is sent over a network.

In an aspect, a scent cartridge for a networked scent diffusion device, may include a reservoir that holds a liquid and an atomizer head assembly, wherein the atomizer head assembly includes an orifice plate containing a flow restriction orifice for passing compressed gas to be mixed with liquid before passing through an atomizing orifice and an RFID tag associated with at least one of the reservoir and the atomizer head assembly, wherein when an RFID reader operably connected to the scent diffusion device recognizes the RFID tag, scent is dispensed from the cartridge.

In an embodiment, a scent cartridge for a networked scent diffusion device may include a reservoir that holds a liquid and an atomizer head assembly, and an anti-tampering identifier associated with at least one of the reservoir and the atomizer head assembly, wherein the scent diffusion from the device is based on the condition of the anti-tampering identifier. When the scent diffusion device does not recognize the anti-tampering identifier, an alert may be sent over a network and scent may not be dispensed. If the cartridge is removed from the device based on the device no longer recognizing the anti-tampering identifier, an alert may be sent over a network.

In an embodiment, a scent cartridge for a networked scent diffusion device may include a reservoir that holds a liquid and an atomizer head assembly, and an RFID tag associated with at least one of the reservoir and the atomizer head assembly, wherein when an RFID reader operably connected to the scent diffusion device recognizes the RFID tag, scent is dispensed from the cartridge. When the scent diffusion device does not recognize the anti-tampering identifier, an alert may be sent over a network and the scent may not be dispensed. If the cartridge is removed from the device based on the device no longer recognizing the anti-tampering identifier, an alert may be sent over a network. The atomizer head assembly may include an orifice plate containing a flow restriction orifice for passing compressed gas to be mixed with liquid before passing through an atomizing orifice.

In an embodiment, a scent cartridge for a networked scent diffusion device may include a reservoir that holds a liquid and an atomizer head assembly and an electrical contact disposed on at least one of the reservoir and the atomizer head assembly, wherein when the electrical contact of the scent cartridge makes contact with a corresponding electrical contact of the scent diffusion device, scent is dispensed from the cartridge. When the scent diffusion device does not recognize the anti-tampering identifier, an alert may be sent over a network and the scent may not be dispensed. If the cartridge is removed from the device based on the device no longer recognizing the anti-tampering identifier, an alert may be sent over a network. The atomizer head assembly may include an orifice plate containing a flow restriction orifice for passing compressed gas to be mixed with liquid before passing through an atomizing orifice In an embodiment, a method for securing networked scent diffusion devices may include associating an anti-tampering identifier with a reservoir and an atomizer head assembly of a networked scent diffusion device 2102, determining if the anti-tampering identifier is present on the reservoir or atomizer head assembly 2104, blocking diffusion if the anti-tampering identifier is absent, and communicating the absence of the anti-tampering identifier to other networked scent diffusion devices 2108. In another embodiment, In an embodiment, the method for securing networked scent diffusion devices may include associating an anti-tampering identifier with a reservoir of a networked scent diffusion device, determining if the anti-tampering identifier is present on the reservoir, blocking diffusion if the anti-tampering identifier is absent, and communicating the absence of the anti-tampering identifier to other networked scent diffusion devices.

In an embodiment, a diffusion device for atomizing liquids may include at least two reservoirs that hold a liquid, a liquid level sensor disposed in the device, an anti-tampering identifier associated with at least one of the reservoirs and a switch, and a processor, operatively coupled to the liquid level sensor, for generating a first signal indicative of the liquid level, a second signal indicative of the presence of the anti-tampering identifier, and a control instruction for the switch based on the first and second signals to cause the device to switch from utilizing one reservoir in the atomizing diffusion device to utilizing a different reservoir in the atomizing diffusion device.

In an embodiment, a method for operating networked scent diffusion devices in an environment to achieve a scent impression goal may include receiving an indication at a networked scent diffusion device that diffusion from one or more other networked scent diffusion devices is blocked due to a tampering indication 2002, accessing an environment model for the environment, wherein the model includes one or more networked scent diffusion devices 2004, and programming a scent diffusion profile for the environment to be executed by one or more of the remaining non-blocked networked scent diffusion devices to achieve the scent impression goal 2008. In certain embodiments, the model includes two or more networked scent diffusion devices.

In an embodiment, an atomizing diffusion device may include at least two packages with liquid disposed in the diffusion device, an anti-tampering identifier associated with at least one of the packages, and a processor, operatively coupled to the scent diffusion device, that determines a tampering indication based on the anti-tampering identifier and causes a switch between the packages based on the tampering indication.

In an embodiment, the diffusion device may include a chemical sensor in fluid communication with the package for detecting the presence of a specific component in a liquid, such as one disposed within the package. The specific component may be a tracer or tag molecule placed in the package, so that when the tag or tracer is detected, the package is authenticated. Conversely, if the tag or tracer is absent, the package may be identified as potentially fraudulent. In embodiments the chemical sensor may be disposed outside the package, but may be in fluid communication with the contents of the package in order to sample the liquid of the package to determine the presence or absence of the specific tag or tracer component. If the chemical sensor detects the specific component, and thus authenticates the package, the device may proceed to operate to diffuse the liquid as described herein. If the specific component is not detected, various actions may be taken. For example, a visual or audible signal may be generated, such as a flashing light (e.g., an LED) or a beeping sound, or any other visual, auditory, tactile, or other sensor cue that would alert a user or observer of a potential problem, such as cues of various types known to those of ordinary skill in the art. Such a signal may indicate the absence of the specific component, which may be due to tampering, an incorrect package, a depleted package, an error, or the like. In other embodiments, the signal take the form of a message, alert, or communication that is transmitted over a network, such as to a central location, an individual, a manager, a computer, a mobile device, and the like. In certain embodiments, the chemical sensor may sample the air for the specific component, and when the component is not present in the air, the sensor may send an instruction over the network to the diffusion device to cease operation.

Figure 4:
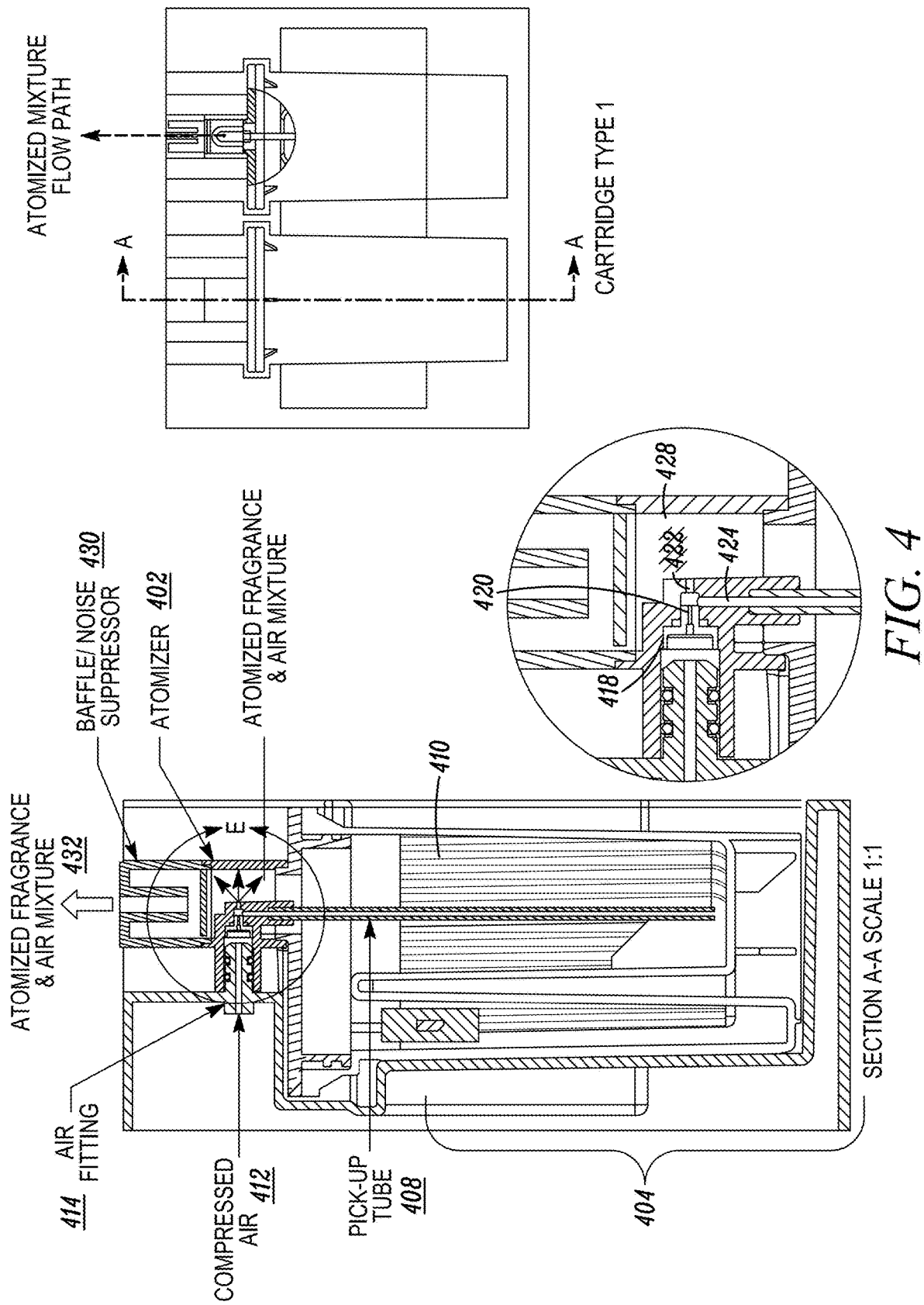
FIG. 4 depicts an embodiment of a package for a diffusion device.

In embodiments, the package may be embodied in a cartridge, a reservoir, a bag, a balloon, a membrane, and the like. Referring to FIG. 4, a cartridge for a scent management system includes a liquid reservoir 404 and an atomizer head assembly 402, wherein the liquid reservoir is positioned below the atomizer head. The liquid reservoir has a substantially cup shaped geometry, and its top edge is joined to the atomizer head assembly, such as by an ultrasonic weld, a twist lock with o-ring seal, or the like. A conduit or tube 408 for the transportation of the liquid in the reservoir is joined to the atomizer head on its first end, and the second end of the tube extends into the liquid 410 within the reservoir, preferably extending sufficiently below the surface of the liquid to maximize the total volume of liquid drawn from within the reservoir as the liquid within the cartridge is depleted. There may be some condensation, but mostly the excess liquid stays in state and drops back into the reservoir.

The atomizer head may have a gas (e.g. air) inlet passage 412 having one end in fluid communication with a compressed air source. The second end of the gas inlet passage may be in fluid communication with an orifice plate 418 containing a flow restriction orifice 420. In certain embodiments, a venturi may be used in place of an orifice plate. The orifice plate separates the gas inlet passage from a mixing chamber 422. The mixing chamber may have a wall opposite the orifice plate, the opposing wall having an atomizing orifice 422. Another wall of the mixing chamber may have an opening 424 in fluid communication with the tube. The atomizing orifice may be in fluid communication with an expansion chamber 428. The expansion chamber may be in fluid communication with a baffle chamber 430. The baffle chamber may have an outlet 432 to the surrounding environment to be treated with the atomized liquid.

The operation of the atomizer head may be as follows: Compressed gas flows into the gas inlet passage, through the orifice plate's flow restriction orifice, and into the mixing chamber. This creates a relatively high-pressure region on the gas inlet passage side of the restrictor orifice, and the gas flow velocity out from the restrictor orifice increases and generates a relatively low pressure region on the mixing chamber end of the restrictor orifice. The relative low pressure draws liquid from the reservoir into the mixing chamber through the tube, and the liquid joins the flow path of the gas out of the restrictor orifice creating a mixture of gas and liquid. The gas liquid mixture then passes through the atomizing orifice into the expansion chamber, creating an atomized mixture of liquid and gas. The atomized mixture of liquid and gas flows into the baffle chamber, and the atomized liquid and gas flows through the outlet into the surrounding environment to be treated.

As the atomized mixture of liquid and gas flow though the expansion chamber and baffle chamber, it impinges on the surfaces of the chambers and walls separating the chambers. This results in the removal of a substantial portion of the larger particles of atomized liquid from the atomized liquid and gas mixture. The larger particles condense back into liquid and drain back into the reservoir through a weep hole in the partition between the expansion chamber and the reservoir. Also, any liquid not completely atomized after the gas and liquid pass through the atomizing orifice drains back into the reservoir through the weep hole. The baffle chamber also acts as a sound level suppressor, muffling the sound of the gas and atomized liquid flow through the atomizer head assembly. The cartridge is inserted into a diffusion device, with the compressed gas inlet passage coupling with an air fitting 414 to provide the supply of compressed gas to the cartridge.

The package may be used in the diffusion devices described herein but also in other scent diffusion devices, such as devices that plug into a wall outlet.

In an aspect, a package for use with a scent diffusion device may include a reservoir that holds a liquid and an atomizer head assembly, wherein the reservoir is joined to the atomizer head assembly at a top edge of the reservoir and a tube for the transportation of the liquid in the reservoir, wherein the tube is joined to the atomizer head assembly on a first end while a second end of the tube extends below the surface of the liquid. A gas inlet passage of the atomizer head assembly may have one end in fluid communication with a compressed air source and a second end of the gas inlet passage in fluid communication with an orifice plate comprising a flow restriction orifice. A mixing chamber of the atomizer head assembly may be separated from the gas inlet passage by the orifice plate, the mixing chamber having a first wall opposite the orifice plate comprising an atomizing orifice and a second wall comprising an opening in fluid communication with the tube. An expansion chamber may be in fluid communication with the atomizing orifice and a baffle chamber, the baffle chamber having an outlet to a surrounding environment. A gas flowing into the gas inlet passage through the flow restriction orifice generates a relatively low pressure region in the mixing chamber that causes liquid from the reservoir to be drawn into the mixing chamber through the tube where it joins the flow path of the gas out of the restrictor orifice creating a mixture of gas and liquid which then becomes atomized when it passes through the atomizing orifice. The liquid reservoir may have a substantially cup shaped geometry. The top edge of the reservoir may be joined to the atomizer head assembly by one of an ultrasonic weld and a twist lock with o-ring seal.

In embodiments, certain diffusion devices may be capable of dispersing multiple fragrances or other liquids. In embodiments, the networked scent diffusion device may include the capability to accept multiple packages (also known as cartridges or reservoirs) for operation in multiple configurations. The diffusion device may be able to accept a plurality of packages, such as greater than one package. In one example, the diffusion device has two packages. When one package is depleted or near depletion, the diffusion device may switch to diffusion from the second package. In another example, the diffusion device can accept four packages, where two packages house a first scent and the other two packages house a second scent, so that both the first scent and the second scent each have backup packages and the diffusion device can automatically switch to a new package when one becomes empty or is near depletion. In embodiments, the combined volume of liquid in the packages installed in the device may be greater than a percentage of the expected use in a replenishment service cycle. For example, the combined volume of liquid may be more than 50% of the expected use in a service cycle. Switching between packages may be done upon sensing when a package is depleted or near depletion or may be done on some other basis, such as after an elapsed time, if it is day or night, upon detection of a condition, upon detection of a user, and the like. A switching system is described elsewhere herein.

In another example, the diffusion device may operate with multiple fragrance packages, and each package may house a different note of a fragrance chord, wherein the diffusion device may be programmed to blend the notes to form the fragrance chord. In embodiments, the fragrance chord may be a particular combination of "base," "mid-" and/or "high" notes. The fragrance chord may be specified by a brand/media campaign specification.

In order to maintain consistent fragrance in an environment where fragrance oil in a reservoir may experience some evaporation or depletion, certain methods may be employed. Fragrance oil is a mixture of numerous liquids, each with different partial pressures. When using atomization, components with higher vapor pressures will flash off earlier, and the heavier components will recycle back into the oil reservoir. The net effect is that as the fragrance oil depletes the fragrance chord, or resultant fragrance, will actually change. One method to potentially influence this effect is to shift the duty cycle of the diffuser device (e.g. increase the t in the duty cycle) as the oil level depletes. Knowing the liquid level, either through sensors, direct measurement or estimation, enables applying the correction factor, t, to preserve the fragrance chord. Another method may involve leveraging a second cartridge. In this scenario, if the main cartridge is partially depleted, adding a small amount of the fragrance oil contained in the second cartridge will add top notes back to the fragrance chord.

In an embodiment, as scent oil is depleted over time in a package of a diffuser device with a scent oil recycling feature, the average size of the molecules in the remaining scent oil increases. One statistical explanation is that larger molecules of scent oil are more likely to fall back into the package through the recycling feature during atomization. This change in average molecule size may affect the performance of the diffuser and may result in a lower rate of scent diffusion for a fixed duty cycle setting. A process for adjusting the duty cycle of the diffuser device to compensate for this change in average molecule size and reduced rate of diffusion may include increasing the duty cycle, pump pressure or other diffuser setting which affects rate of diffusion. In one embodiment, a liquid level sensor of the diffusion device may determine the liquid level remaining in the package and a processor of the diffusion device may use the sensed liquid level to modify a diffuser setting as described herein in order to maintain a desired rate of scent diffusion, a target value of a scent, or a brand management goal. A method may include receiving a sensed liquid level in a package of a scent diffusion device, wherein non-atomized scent oil is recycled back into the package during device operation and adjusting the duty cycle of the diffusion device to maintain a desired rate of scent diffusion. Adjusting may include at least one of increasing the duty cycle, increasing the pump pressure, and changing a diffuser setting.

In another example, the diffusion device may be capable of accepting multiple packages, and switching between the packages is done in accordance with a time, such as to deliver a day and a night fragrance. In yet another example, the diffusion device is capable of accepting a plurality of packages, wherein one package includes a scent neutralizer and one or more other packages includes a fragrance, such as the diffusion device can switch to the scent neutralizer as needed or in between dispersion of different fragrances. In yet another example, the diffusion device may house multiple packages and the desired package may be selected remotely. For example, when a guest arrives in a lobby of the hotel, they may choose a particular fragrance to diffuse in their hotel room. The fragrance diffusion may be triggered remotely. Continuing with the example, the guest may have chosen the fragrance ahead of time upon booking or sometime prior to arrival, such that the fragrance is triggered when the room becomes available for the guest, when the guest is checked in, when the guest enters the room and is sensed by an occupancy sensor or Bluetooth/WiFi sensor, or the like. In yet another example, the diffusion device may house multiple packages and the liquids in the packages may be blended prior to diffusion.

In still another example, one of the packages could be a diluent to reconstitute a concentrated fragrance oil, and the blending could be done at the level of the diffuser. Blending may be programmed to produce a scent concentration factor specified by a brand/media campaign specification. In this example, a plurality of concentrated fragrances may be available in the diffusion device (such as in a carousel), and one or more of the plurality of fragrances can be selected for diffusion.

In a further example, the diffusion device may accept a single use package of fragrance, either in addition to the existing dual package configuration or instead of it. For example, a guest in a hotel may be offered various single use packages of fragrance for selection in a lobby that they can install themselves into the diffusion device. In still a further example, the scent in the package may be provided by a crystal, a powder, or another non-liquid element that is reconstituted or diluted prior to diffusion.

In embodiments, the fragrance used by the diffusion devices may match scents to be used in passive scent devices, such as candles, tarts, or gels. The fragrance may be delivered as an oil or as a solid, such as a solid crystal.

Switching between packages may be done using an automated switching system. An automated switching system for a networked scent diffusion device housing a plurality of fragrance packages enables a switch between packages upon meeting a condition. For example, the condition can be the determination that a level of a fragrance in a package is low. In another example, the switch may be done after an elapsed time in a programmed switchover to mitigate scent desensitization. In embodiments, the device may utilize a FIFO replenishment process.

In embodiments, the switching system employs a valve. In embodiments, the switching system employs a liquid level sensor, such as an electrical (e.g. conductive, capacitive transmitters to measure the cumulative capacitance which is a function of the amount of liquid and is based on the liquid's dielectric constant, resistive), magnetic (e.g. Hall effect sensor or Hall effect switch), mechanical (e.g. liquid level float that triggers a switch, physical switch, strain gauge), optical (e.g. imaging sensor, liquid level float plus imaging sensor) liquid level sensor, hydrostatic sensors (e.g. displacers, bubblers, differential pressure transmitter) to measure the pressure of the liquid, load cells to measure the mass in the package, electromagnetic transceivers that transmit an EM signal at the surface of the liquid which reflects back to its receiver with a time delay that is used to calculate the liquid level (EM could be ultrasonic, laser, radar, etc. depending on the wavelength of the EM signal that is sent and received), or any other liquid level sensor. In one embodiment, the liquid level sensor may include a floating magnet disposed within a track inside the package, wherein as the liquid level changes, the floating magnet moves inside the track. At least one Hall effect sensor or Hall effect switch is disposed outside the package, wherein the Hall effect sensor or Hall effect switch is disposed in such a way as to sense the position of the magnet. In an embodiment, when a particular position of the magnet is sensed, which may correspond with a predetermined liquid level, a switch may be activated that causes a move from a first state of the switch to a second state of the switch. The switch may be used to switch the diffusion device's utilization of one package to utilization of another package. For example, the switch may be a solenoid switch between packages. In another embodiment, data from the liquid level sensor may be used to monitor liquid levels inside the one or more packages in the diffusion device and predict when the package(s) will be depleted of liquid. This prediction may be used in scheduling replenishment services so that the diffusion device is never out of liquid. The NOC, a local controller, a gateway device, or any of the devices may perform a days of supply calculation using an algorithm as part of a predictive model to determine when packages in a device will be depleted. The algorithm may utilize measured current liquid level and divide that by the average usage rate per day to determine a number of days of supply remaining. The average usage rate per day may be defined for any time period desired. The result of the calculation may be used to schedule an event, such as a just-in-time replacement of a package, the dispatch of a replenishment technician, or the transmission of an alert/email to on-site personnel. The days of supply calculation may also be done using an estimated liquid level in place of the measured liquid level, wherein the estimate may be determined based on a duty cycle used by the device, optionally in combination with other historical or modeled data regarding device operation. The days of supply calculation may also utilize information such as a duration of operation, a compressed gas usage, and the like in place of the measured liquid level in order to estimate an amount of liquid remaining. In an embodiment, the liquid level sensor for a networked scent diffusion device provides real-time fragrance levels and causes an alert or signal to be generated when the reading from the liquid level sensor indicates a need for replacement of a package, when an unexpected reading is obtained, and the like. In response to receiving the unexpected reading, a control instruction may be sent to the device to turn it off or otherwise cease diffusion operations. If the reading is higher than expected, which may be suggestive of a clog, a control instruction may be sent to the device to switch to a new package. Alerts or signals in this example and throughout this specification may be one or more of visual, audio, electronic (e.g. SMS/MMS, text, email, pop-up, etc.), and the like. Throughout this specification, alerts may be sent asynchronously when the device reports an event, or if a device stops reporting to the NOC for a predetermined period. Throughout this specification, an alert may be triggered whenever a device goes from a non-alert state to an alerted state. If two of the same alerts are reported in a row, the second alert will not cause the device to retrigger a new alert—instead it will consider the alarm still set. Audio alerts may be transmitted through a speaker of the diffusion device. Visual alerts may be transmitted through LED lights of the devices, or the like. In another example, based on the data on the duty cycle and the SCF, a predictive algorithm may be used to estimate the actual liquid level. A single sensor near an empty level of the reservoir may be used to verify liquid level.

In an aspect, an atomizing diffusion device may include a floating magnet disposed within a track inside at least one package with liquid for the diffusion device, wherein as a liquid level inside the package changes, the floating magnet moves substantially vertically along the track. The device may further include at least one Hall effect sensor or Hall effect switch disposed outside the liquid at a position to enable sensing the position of the floating magnet in the track. The device may also include a processor, operatively coupled to the Hall effect sensor or Hall effect switch, for generating a signal indicative of the sensed position of the floating magnet and a control instruction for a switch based on the signal and a switch, operatively coupled to the processor, that receives the control instruction from the processor, wherein the control instruction causes the diffusion device to switch from utilizing one package in the diffusion device to utilizing a different package in the diffusion device. The switch may be a solenoid switch. The device of claim may further include a scheduling facility that receives the signal and predicts when the package will be depleted of liquid or determines a package replenishment schedule. The device may further include a remote computer in communication with the processor for receiving the signal and generating an alert if the signal indicates a need for replacement of a package or when an unexpected signal is obtained. The processor may be adapted to send a signal indicating the switch to the different package in the diffusion device In embodiments, the switching system employs a sensor that measures the pressure in the package to determine the presence of a vacuum or a threshold pressure/partial pressure. Certain pressure readings may be associated with a liquid level in the package. When a certain predetermined pressure reading is obtained, it may cause an alert or signal to be generated indicating a need for replacement of a package, an unexpected reading, and the like.

In embodiments, the switching system employs a camera or other imaging facility to monitor the liquid level inside the package. For example, the package may have a transparent portion that may allow a camera to image the liquid level. When the camera determines that the liquid level has dropped to a certain point, an alert or signal to be generated indicating a need for replacement of a package, an unexpected reading, and the like.

Figures 10A, 10B:
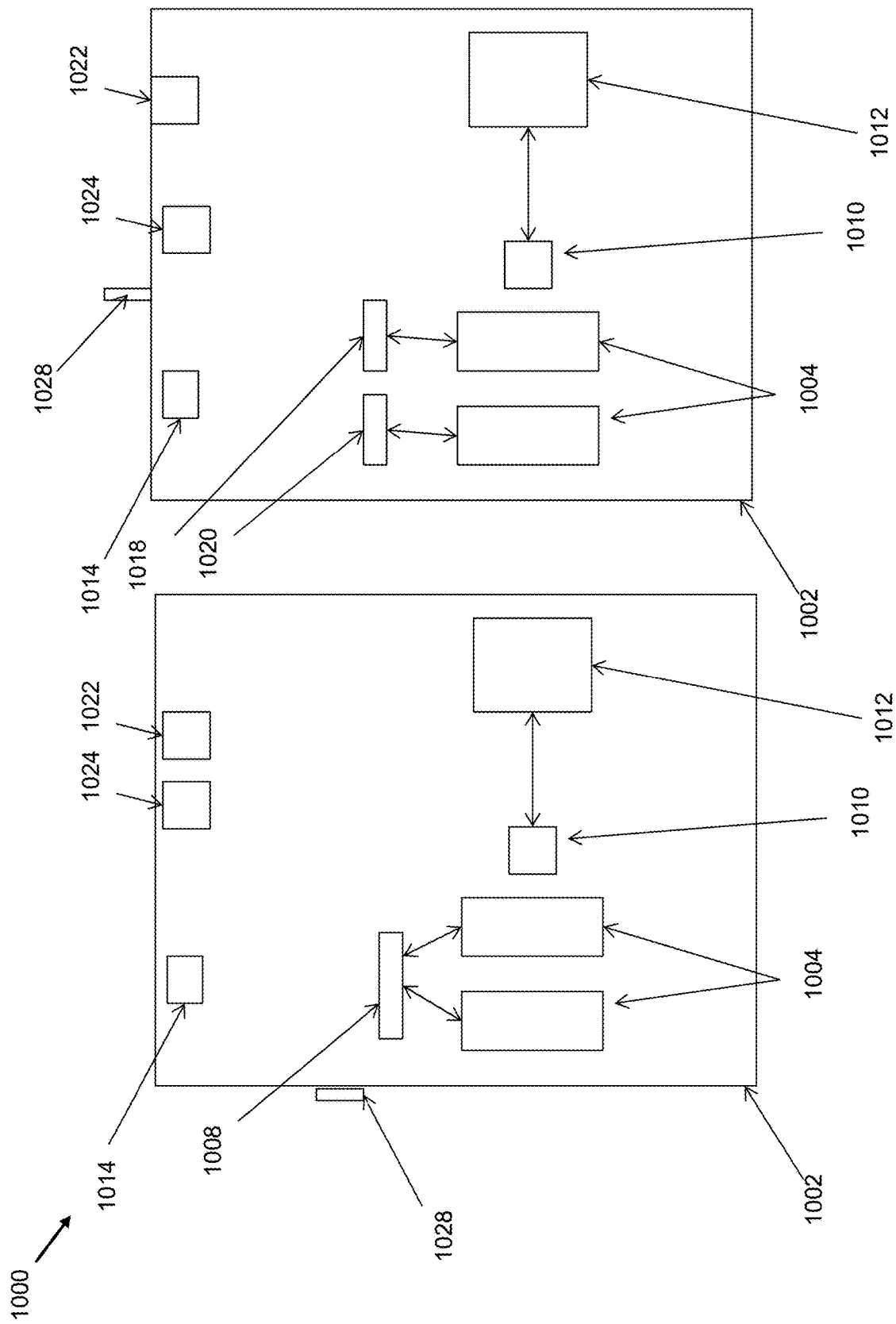
FIGS. 10A and 10B depict a block diagram of a diffusion system.
Figure 11:
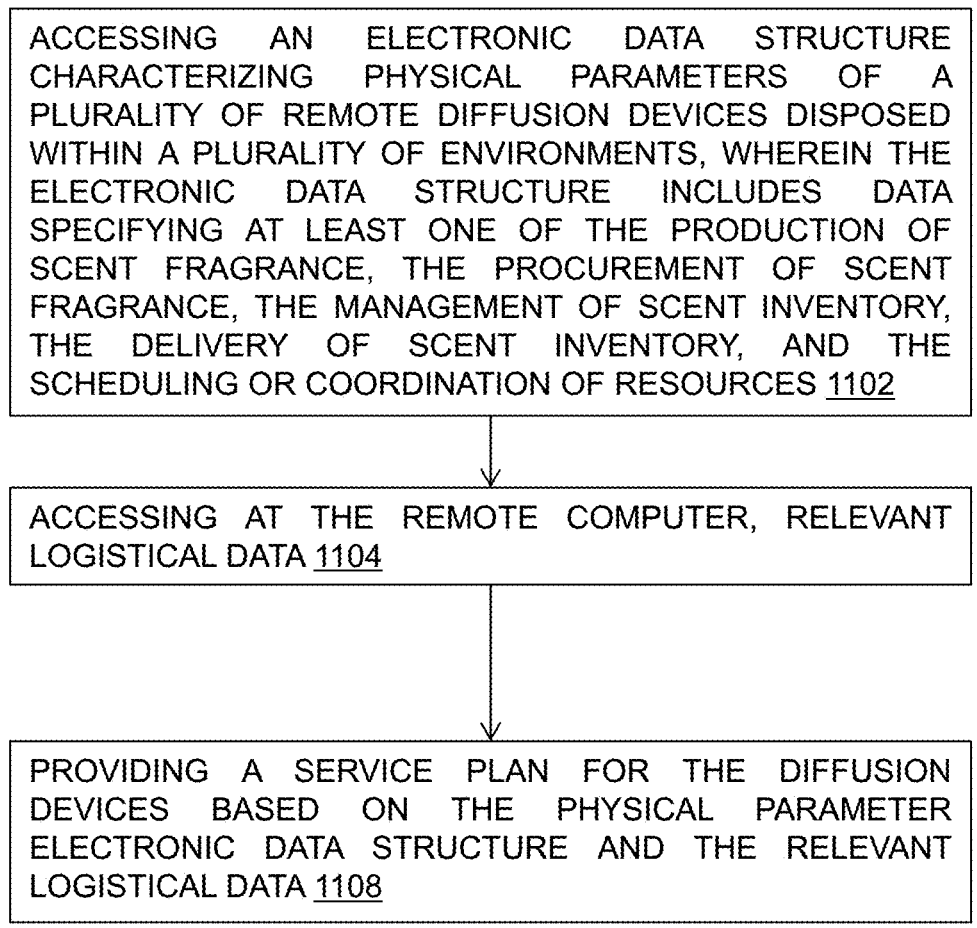
FIG. 11 depicts a method relating to atomizing diffusion devices.
Figure 12:
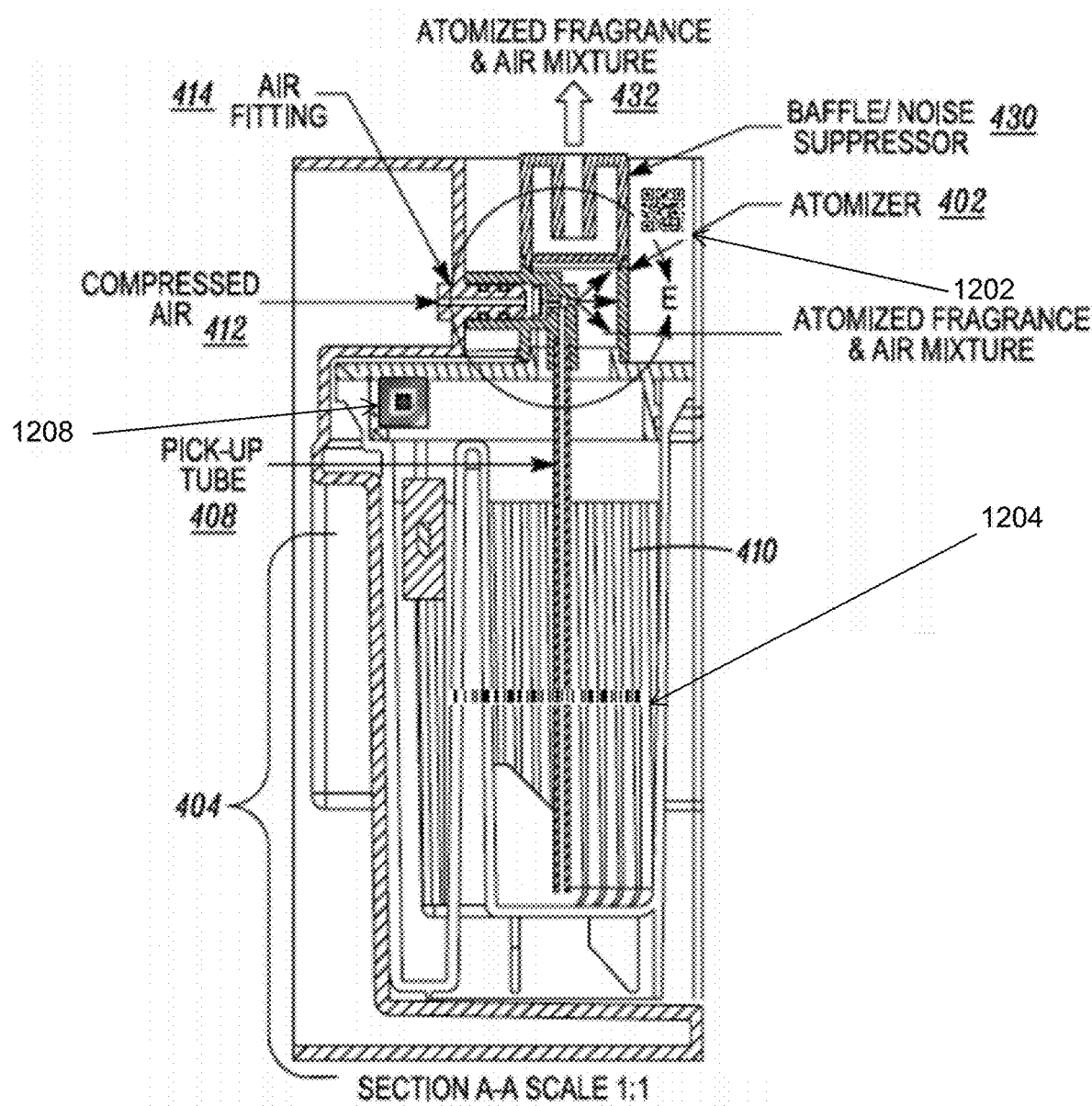
FIG. 12 depicts security features of a package.

In embodiments, and referring to FIG. 10, an atomizing diffusion system 1000 may include a housing 1002 containing at least two packages 1004 with liquid in fluid communication with at least one diffuser 1008 and a sensor 1010. In embodiments, the sensor 1010 is a liquid level sensor 1010 that determines the liquid level in at least one of the packages. In embodiments, the sensor 1010 may be an imaging sensor, a Hall effect sensor, a traffic/occupancy sensor, or the like. The system further includes a processor 1012 operatively coupled to the liquid level sensor for generating a signal indicative of the liquid level and a control instruction for a switch 1014 based on the signal, wherein the switch is operatively coupled to the processor and receives the control instruction from the processor. The control instruction causes the diffusion system to switch from utilizing one package in the diffusion system to utilizing a different package in the diffusion system. In some embodiments of the system, the system switches between a first diffuser 1020 and a second diffuser 1018. In some embodiments of the system, the system switches packages associated with a single diffuser 1008, 1018, 1020. The liquid level sensor may be an imaging sensor, wherein the liquid level inside the package is exposed through at least one of a transparent wall and a transparent window of the package. The switch may be a solenoid switch. The device may further include a communication facility 1022 that enables the processor to transmit the signal to a remote computer, wherein the remote computer uses the signal to generate an alert if the signal indicates a need for replacement of a package or when an unexpected signal is obtained, or predict when the package will be depleted of liquid, or to determine a package replenishment schedule. The liquid level sensor may include a floating magnet disposed within a track inside at least one of the packages, wherein as a liquid level inside the package changes, the floating magnet moves substantially vertically along the track, and at least one of a Hall effect sensor and a Hall effect switch disposed outside the package at a position to enable sensing the position of the floating magnet in the track. The atomizing diffusion device may be a scent diffusion device.

In some embodiments, the atomizing diffusion system includes at least two packages with liquid in fluid communication with at least one diffuser, a liquid level sensor that determines the liquid level in at least one of the packages, and a processor, operatively coupled to the liquid level sensor, for generating a signal indicative of the liquid level and a control instruction for altering a state of the diffusion system. In some cases, the altered state is a switch between packages. In other cases, the altered state is a shutdown of the device.

Referring now to FIG. 24A, an embodiment of the diffusion device includes cartridges 2424, an antenna 2404, a display 2422, and control buttons 2420. FIG. 24B shows a front view of the embodiment of FIG. 24A. FIG. 24C shows the view along Section A-A of FIG. 24B. FIG. 24C depicts a power switch 2428, solenoids 2410, pump 2418, power supply 2402, and power barrel connector 2414. FIG. 24D depicts a power supply 2402, antenna 2404, fan 2408, solenoids 2410, pump 2418, power barrel connector 2414, and level sensor board 2412. The level sensor boards 2412 have a plurality of Hall effect sensors that as the magnet passes by it floating in the cartridge, the liquid level inside the cartridge is measured. The sensors themselves are on the opposite side of the view of the board 2412 in FIG. 24D.

What is seen in FIG. 24D is the board 2412 and the circuit lines running to each of the sensors on the other side.

Figure 13:
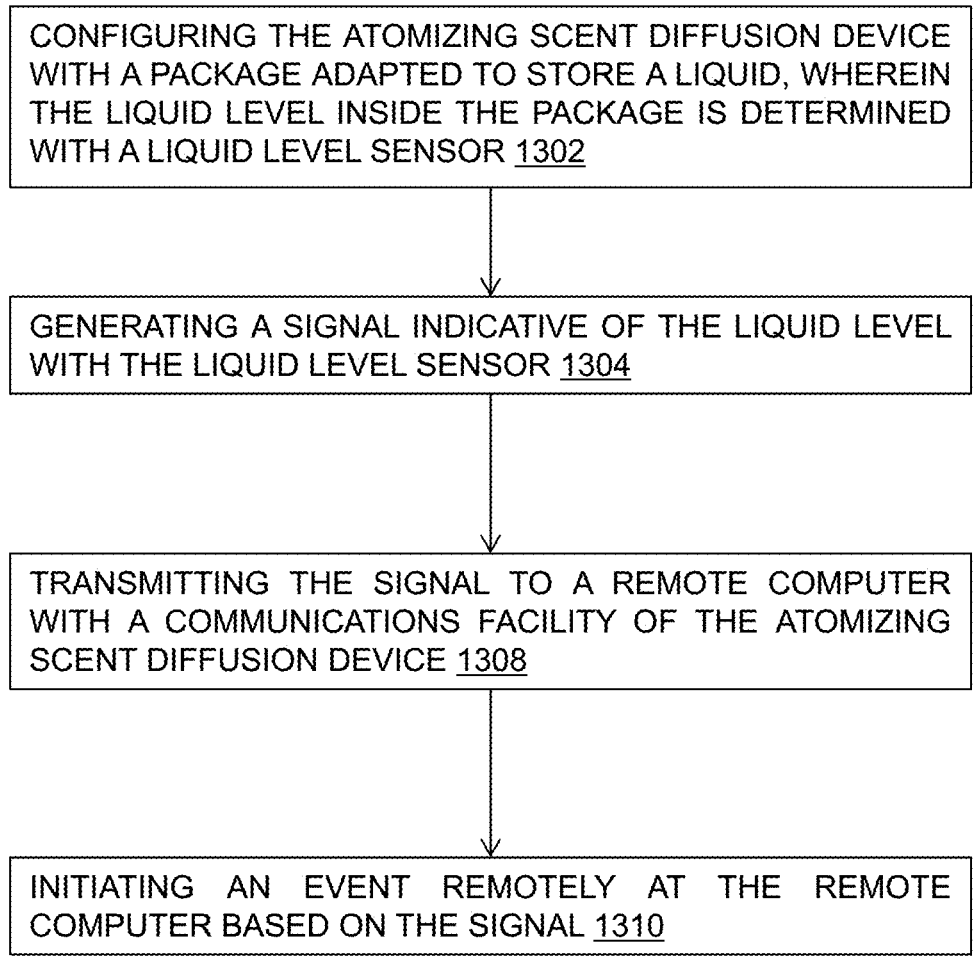
FIG. 13 depicts a method relating to atomizing diffusion devices.
Figure 14:
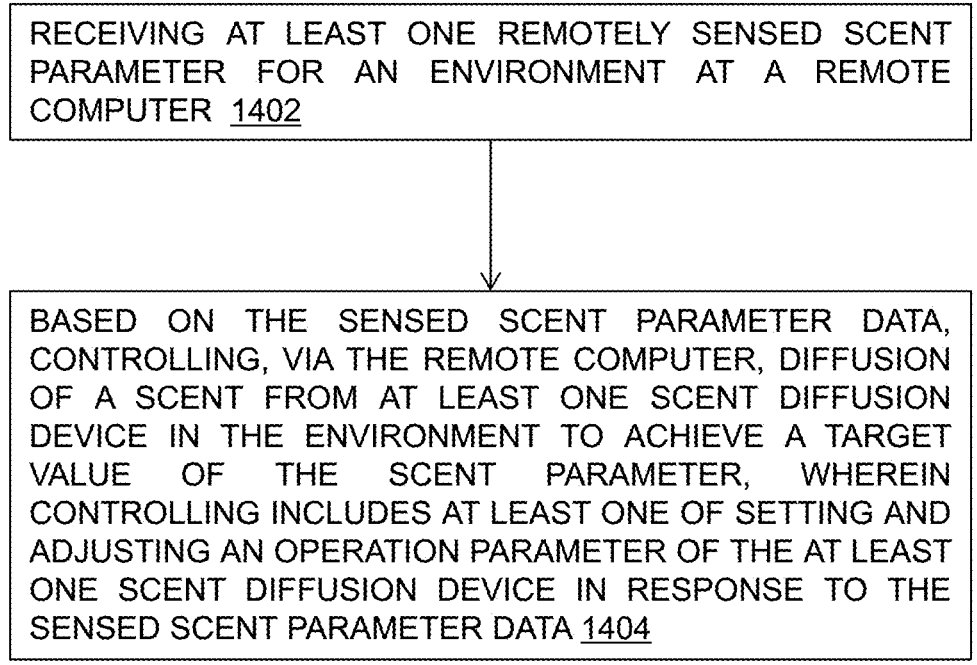
FIG. 14 depicts a method relating to atomizing diffusion devices.
Figure 15:
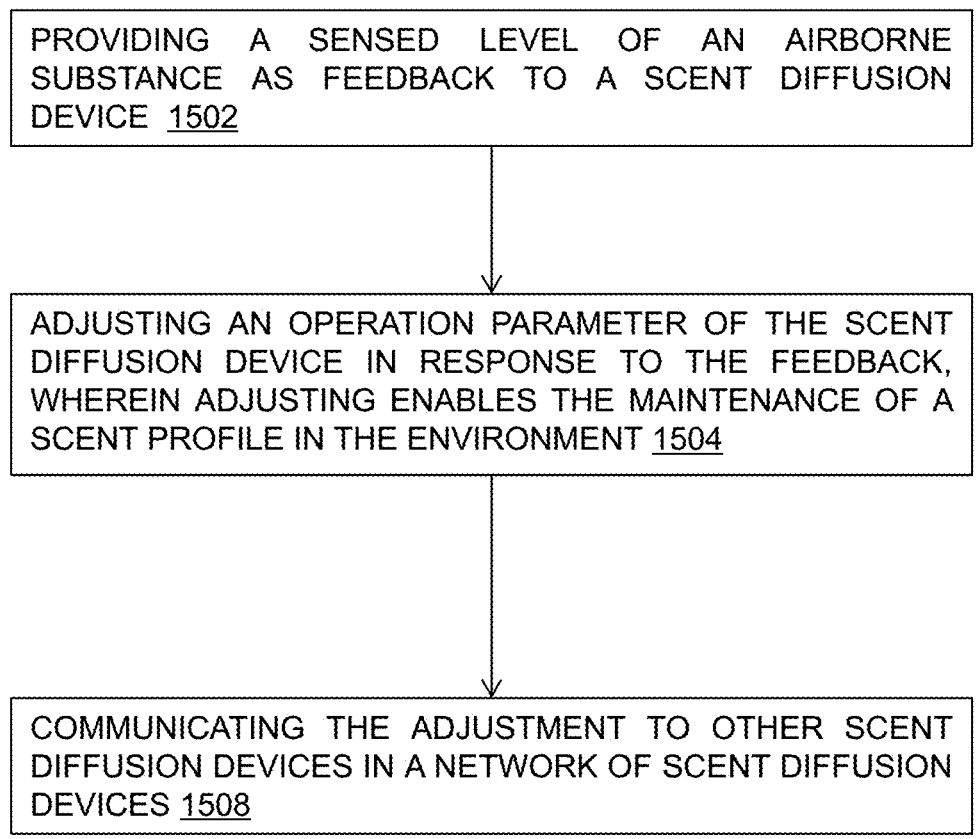
FIG. 15 depicts a method relating to atomizing diffusion devices.
Figure 16:
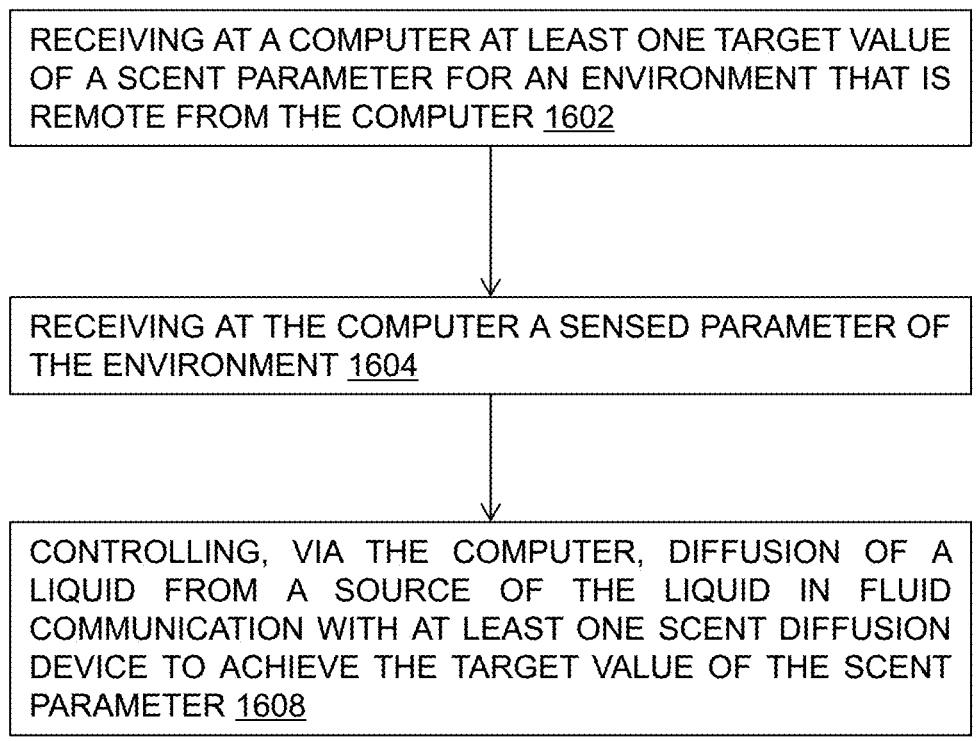
FIG. 16 depicts a method relating to atomizing diffusion devices.
Figure 17:
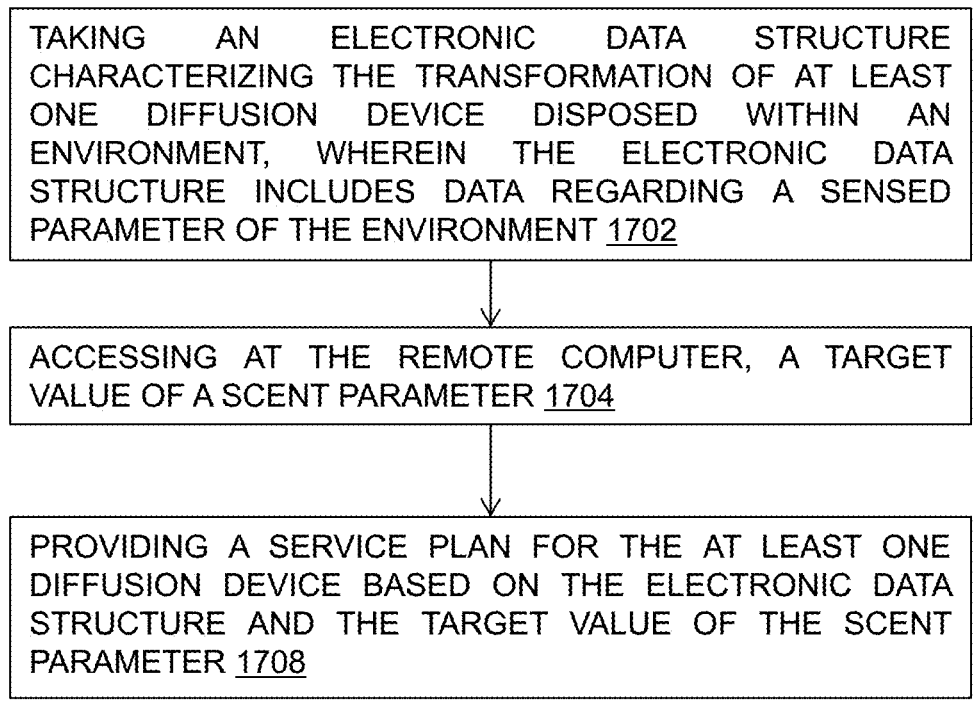
FIG. 17 depicts a method relating to atomizing diffusion devices.
Figure 18:
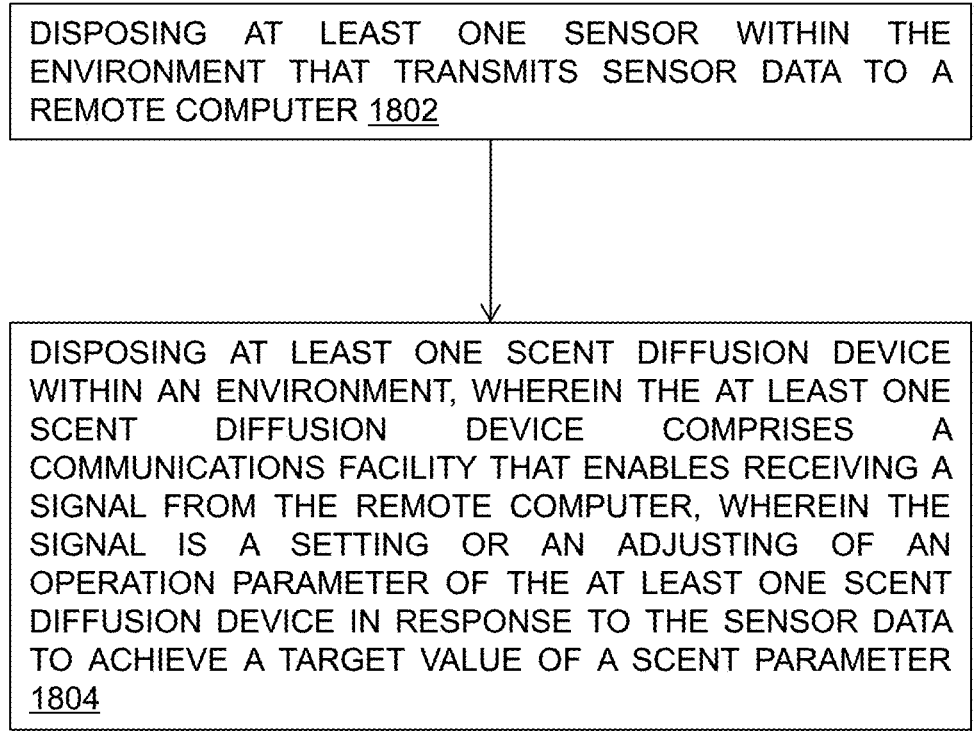
FIG. 18 depicts a method relating to atomizing diffusion devices.
Figure 20:
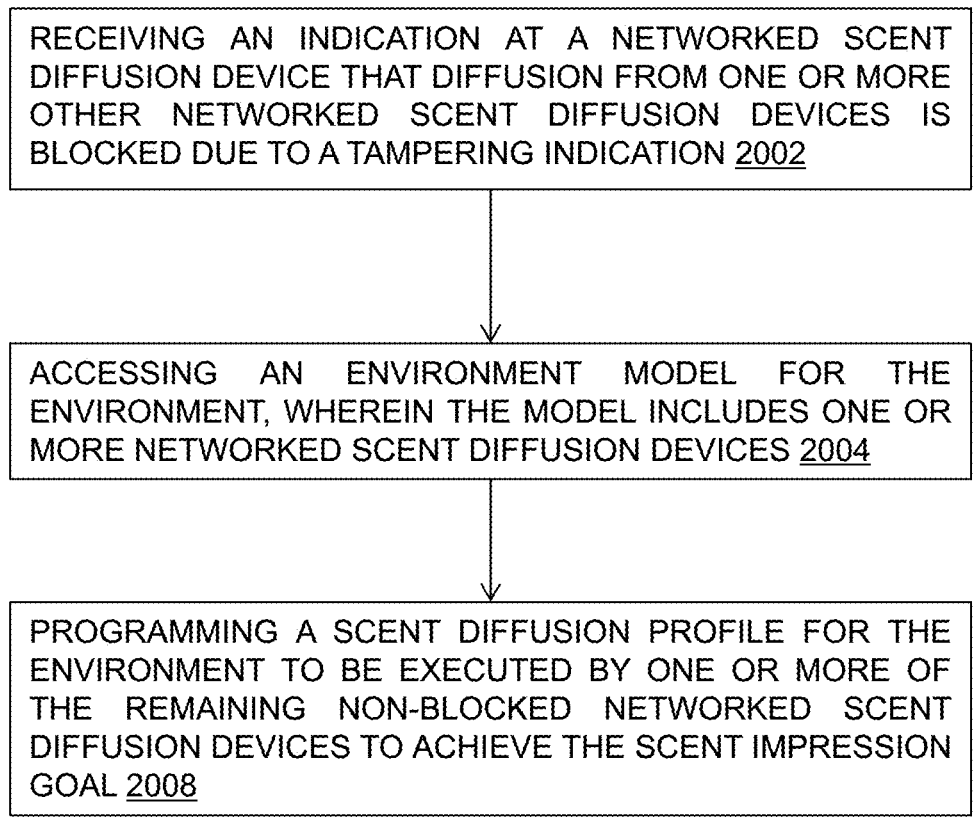
FIG. 20 depicts a method relating to tampering of atomizing diffusion devices.
Figure 21:
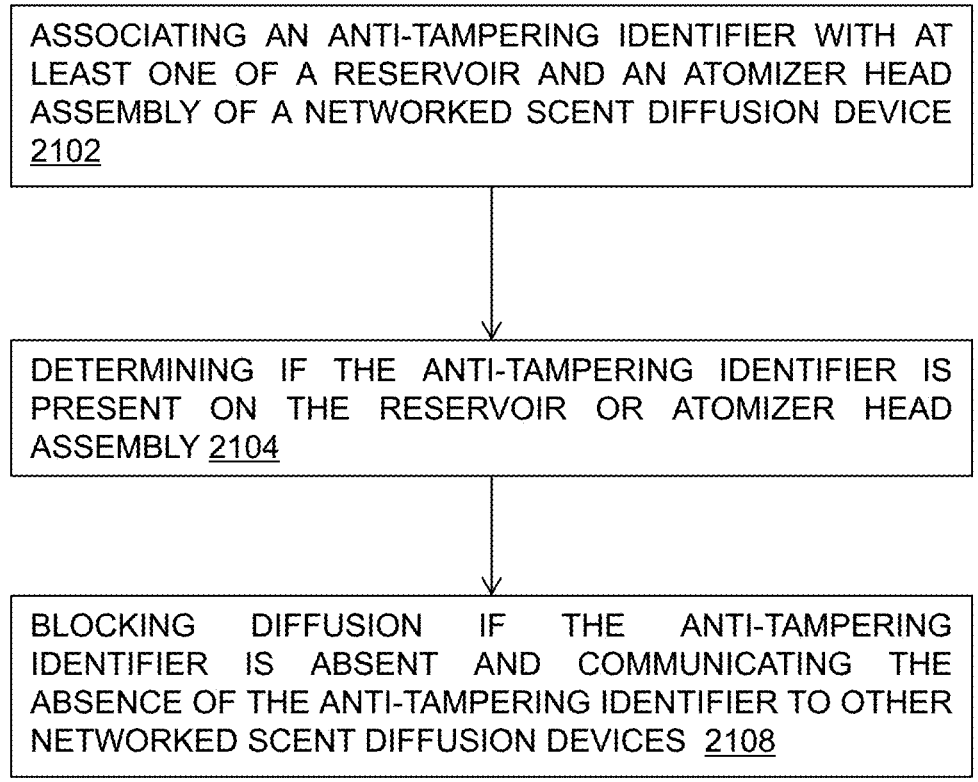
FIG. 21 depicts a method relating to tampering of atomizing diffusion devices.

In an embodiment, and referring to FIG. 13, a method of operating an atomizing scent diffusion device may include configuring the atomizing scent diffusion device with a package adapted to store a liquid, wherein the liquid level inside the package is determined with a liquid level sensor 1302, generating a signal indicative of the liquid level by the sensor 1304, transmitting the signal to a remote computer with a communications facility of the atomizing scent diffusion device 1308, and initiating an event remotely at the remote computer based on the signal 1310. The event may be scheduling a replenishment, dispatch of a replenishment technician, transmission of an alert/email to on-site personnel, predicting a time until depletion, and the like. Predicting may include performing a days of supply calculation. The calculation may involve taking the measured current liquid level and dividing it by the average usage rate per day to determine a number of days of supply remaining. The average usage rate per day may be defined for a time period. The method may further include scheduling a replenishment based on the time. The method may further include generating a control instruction for a switch based on the signal, and receiving the control instruction from the processor, wherein the control instruction causes the diffusion device to switch from utilizing one package in the diffusion device to utilizing a different package also configured in the diffusion device.

In an embodiment, a method of operating an atomizing diffusion device may include configuring the atomizing diffusion device with a package adapted to store a liquid, wherein the liquid level inside the package is estimated using a criteria, coupling a processor to the device to generate a signal indicative of the estimated liquid level, and initiating an event based on the signal. The event may be predicting a time until depletion, an alert, turning off the device or otherwise ceasing diffusion operations, and the like. Predicting may include performing a days of supply calculation. The calculation may involve taking the measured current liquid level and dividing it by the average usage rate per day to determine a number of days of supply remaining. The calculation may involve a duration of operation or a compressed gas usage in place of the measured liquid level in order to estimate an amount of liquid remaining. The average usage rate per day may be defined for a time period. The method may include scheduling a replenishment based on the time. The estimated liquid level may be determined based on a duty cycle used by the device or on historical or modeled data regarding device operation.

In an embodiment, a method of coordinating a plan or plans for servicing atomizing diffusion devices, such as scent diffusion devices, within an environment may include disposing a plurality of scent diffusion devices within an environment, wherein each diffusion device includes a communications facility that enables transmitting signals to and receiving signals from a remote computer, disposing at least one liquid level sensor within each diffusion device, receiving at the remote computer, liquid level data from the plurality of diffusion devices; and based on the liquid level data, determining via the remote computer an efficient or optimized plan or plans for servicing the diffusion devices. The plan or plans may involve one or more of: the production of scent fragrance, the procurement of scent fragrance, the management of scent inventory, the delivery of scent inventory, and the scheduling or coordination of resources to accomplish the plan of efficient or optimized servicing of a plurality of devices within an environment. In embodiments, the plan covers servicing atomizing diffusion devices within a plurality of environments.

In an aspect, a method relating to atomizing diffusion devices within a plurality of environments may include accessing an electronic data structure characterizing physical parameters of a plurality of remote diffusion devices disposed within a plurality of environments, wherein the electronic data structure includes data specifying at least one of the production of scent fragrance, the procurement of scent fragrance, the management of scent inventory, the delivery of scent inventory, and the scheduling or coordination of resources to accomplish the transformation 1102, accessing at the remote computer, relevant logistical data 1104, and providing a service plan for the diffusion devices based on the electronic data structure and the relevant logistical data 1108. The method may further include accessing, at the remote computer, relevant logistical data at the remote computer, and based on the liquid level and logistical data, determining via the remote computer a plan or plans for servicing the diffusion devices. The logistical data may include at least one of the location of each environment or diffusion device, transportation map data, and route optimization algorithms. The liquid level is measured using an imaging sensor. The liquid level inside a package of the atomizing diffusion device may be exposed through at least one of a transparent wall and a transparent window of the package. The liquid level sensor may include a floating magnet disposed within a track inside at least one of the packages, wherein as a liquid level inside the package changes, the floating magnet moves substantially vertically along the track, and at least one of a Hall effect sensor and a Hall effect switch disposed outside the package at a position to enable sensing the position of the floating magnet in the track. Determining the plan may include performing a days of supply calculation, wherein the calculation involves taking the measured current liquid level and dividing it by the average usage rate per day to determine a number of days of supply remaining, and wherein the average usage rate per day is defined for a time period. Scheduling and coordination of resources may include the dispatch of a replenishment technician or the transmission of an alert/email to on-site personnel. The electronic data structure may be generated at a computer based on liquid level data from the plurality of remote atomizing diffusion devices. Each diffusion device may include a communications facility that enables transmitting signals to and receiving signals from a remote computer and at least one liquid level sensor. The liquid level may be measured using a liquid level sensor including a floating magnet disposed within a track inside at least one package of the atomizing diffusion device, wherein as a liquid level inside the package changes, the floating magnet moves substantially vertically along the track, and at least one of a Hall effect sensor and a Hall effect switch disposed outside the package at a position to enable sensing the position of the floating magnet in the track. The physical parameters may relate to liquid levels of the diffusion devices.

In an embodiment, an atomizing diffusion device may include at least two packages with liquid in fluid communication with a scent diffusion device, wherein the liquid level inside the package is exposed through at least one of a transparent wall and a transparent window of the package. At least one imaging sensor may be disposed outside the package in the diffusion device to image the liquid level in the package. A processor may be operatively coupled to the imaging sensor to generate a signal indicative of the liquid level and a control instruction for a switch based on the signal. The switch may be operatively coupled to the processor to receive the control instruction from the processor, wherein the control instruction causes the diffusion device to switch from utilizing one package in the diffusion device to utilizing a different package in the diffusion device. The processor may be adapted to send a signal indicating the switch to the different package in the diffusion device.

In embodiments, the liquid level sensor may be used in combination with another measure to determine if the diffusion device is performing correctly. For example, if the liquid level sensor indicates a particular level of liquid inside the package, but the pump activity and/or rate of consumption of compressed air indicates that more liquid should have been depleted, an alert or signal may be generated indicating the unexpected reading. Such an unexpected reading may be caused by a leak in the system or a clogged atomization nozzle or any of many possible malfunctions or performance issues.

In an aspect, an atomizing diffusion device may include at least two packages with liquid in fluid communication with a scent diffusion device, wherein a first package contains a neutralizer and a second package contains a scent, a communications facility that receives data from on detected malodors, and a processor, for executing a control instruction based on the data to cause the diffusion device to diffuse at least one of the neutralizer, the scent, and a mixture of the two to counteract the malodor. The data may be derived from environmental sensors. The control instruction may be changing the duty cycle of diffusion of the scent and neutralizer agents. Changing the duty cycle may involve solenoids for each package opening for a certain % of the duty cycle. The data may be derived from a wind direction sensor detecting neighborhood malodors being carried toward a scenting location or a humidity sensor.

In an embodiment, the wireless, networked diffusion devices communicate with one another via a networking protocol, wherein the communication between the devices enables generating a consistent scent profile in a wide area. Each diffusion device is capable of operating in several modes, depending on the presence of a WWAN module within the device and its start-up protocol. With a WWAN module installed, the device may auto configure itself in "gateway mode" and may be known as a scent gateway device. With no WWAN module installed, the device may be known as a scent node device. In any event, devices may further include a LAN card. Devices may communicate with one another or may be stand-alone. Alternatively, in some local networking scenarios, devices may be hard-wired to one another and/or to a central networking device. In some embodiments, the devices may transmit and receive communication through a cloud server.

In one scenario, a scent dispersion network is established, comprising one scent gateway device and one or more scent node devices, where the scent gateway device and the scent node device may be diffusion devices as described herein. In one embodiment, this may be accomplished in the following manner: 1) the scent gateway device is installed and plugged into AC or DC power; 2) a startup protocol within the scent gateway device includes a self-diagnostic, followed by activation of the WWAN module, and the establishment of communications with the NOC; 3) the scent gateway device then receives configuration settings from the NOC, and begins dispersing scent according to its downloaded programming; 4) upon establishing its own configuration, the scent gateway device searches its wireless local area network for scent node devices; 5) upon identifying scent node devices, the scent gateway device then establishes communications with each scent node device; 6) the scent gateway device gathers information from each scent node device, and then relays that information to the NOC; 7) the NOC receives the device information and communicates program settings and information to each scent node device, via the scent gateway device; 8) each scent node device, having received its configuration settings from the NOC via the scent gateway device, begins dispersing scent according to its downloaded programming. This exemplary scenario provides remote and centralized management of a scent dispersion network via a scent gateway device, which is a scent dispersion device that also acts as the network gateway. Communication between devices may occur via various networking protocols listed elsewhere herein, such as Bluetooth (full power and LE), MiWi, Zigbee, and the like. In embodiments, for a large area, multiple gateway devices may be deployed to establish one or more scent dispersion networks in a location.

Once a scent dispersion network is established, the scent gateway device may continue to communicate and store data and instructions to and from each paired or associated scent dispersion device within a venue, and then relays the data and instructions between the NOC and each scent dispersion device. In this manner, the status of the scent dispersion network and each device is regularly communicated to the NOC, and NOC administrators are able to remotely monitor scent dispersion network operations, and control the devices to take actions to ensure fragrance dispersion is conforming to commercial brand standards or other parameters. In one embodiment, the scent dispersion network includes only a scent gateway device in communication with a NOC and no associated or networked scent node devices.

Figure 2:
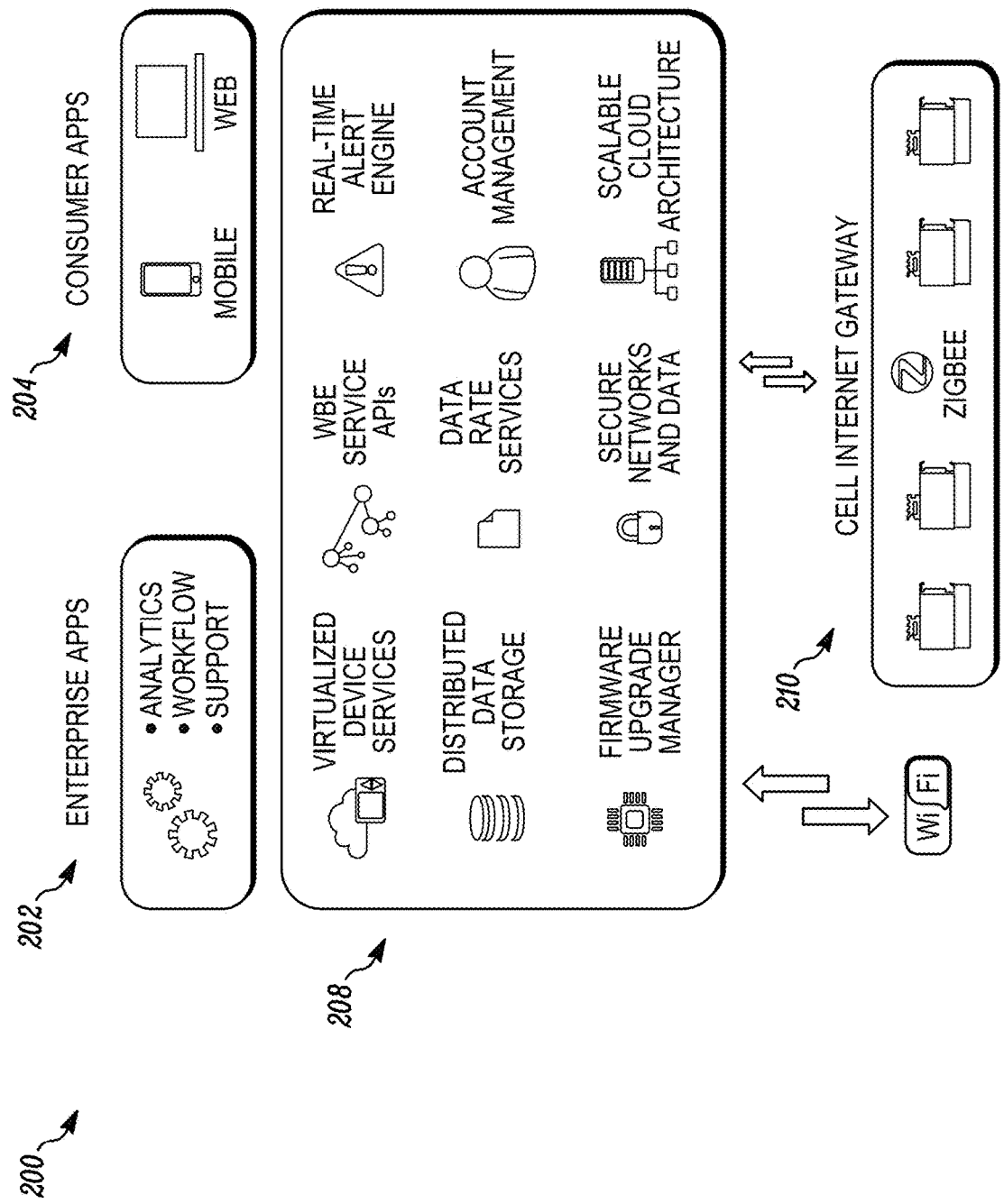
FIG. 2 depicts an embodiment of network operations software interfacing with enterprise applications and consumer applications.
Figure 3:
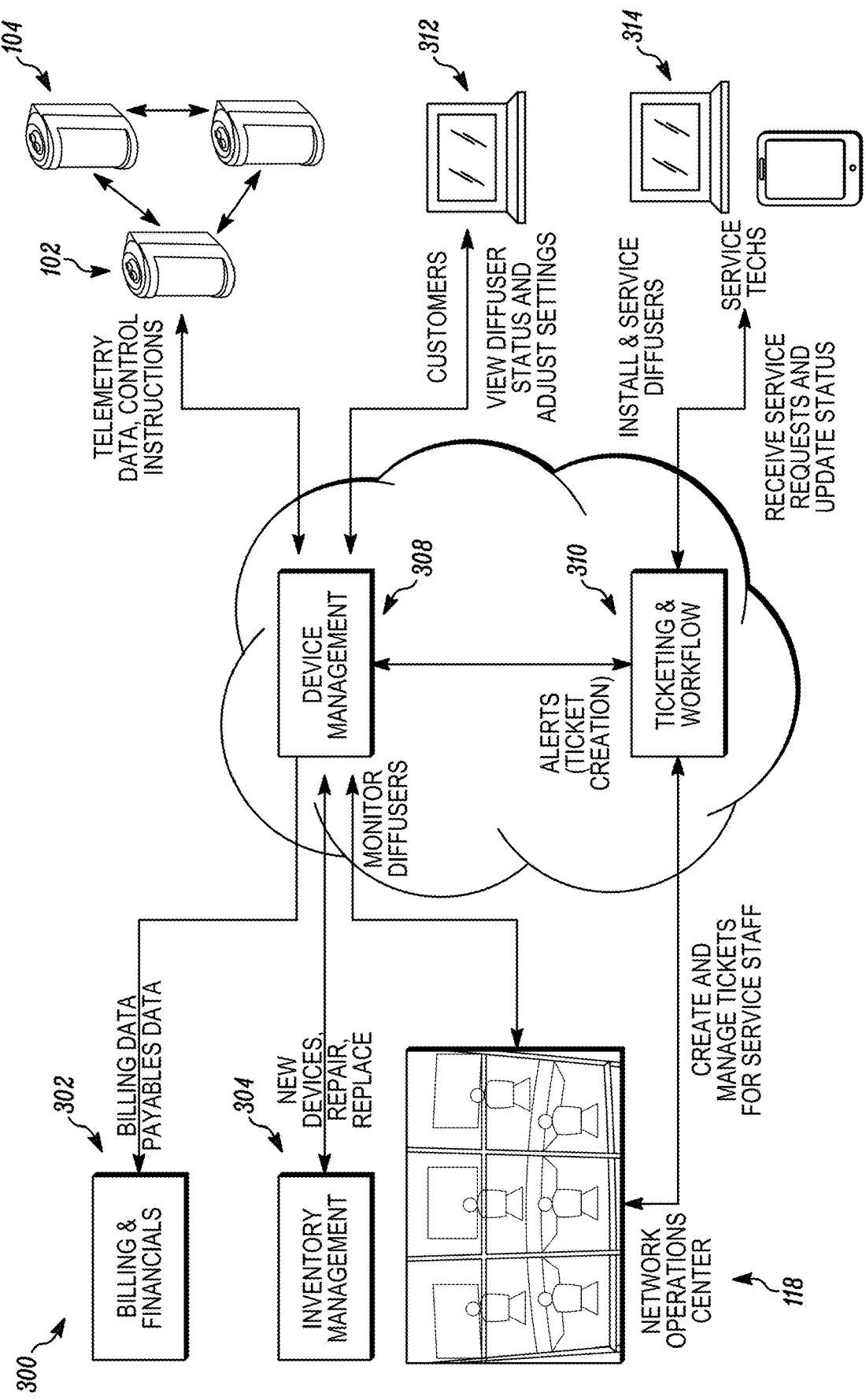
FIG. 3 depicts an embodiment of enterprise architecture.

The NOC may include a database of all diffusion devices in the field, including information such as device type, location, customer, sensor readings from the diffusion device, a scent diffusion level, fragrance oil volume, fragrance oil type, package/reservoir type, compressed air volume, number of devices in a local network, an on/off status, any alerts, current firmware, permissions and security settings, and the like. Any of the device settings or statuses may be viewed and/or or controlled remotely by a NOC user. The NOC enables running reports in order to check system health and effectiveness at customer locations and generating alerts when diffusion device issues are detected at customer sites. The NOC enables managing cellular wireless provisioning, accounts, usage; remotely managing local mesh wireless networks used to interconnect diffusion devices at a customer site; managing firmware updates in the field; utilizing centralized software applications to gather telemetry data from diffusion devices over the Internet; and the like. A ticketing and workflow facility, described elsewhere herein, for fired alerts may allow NOC users to log responses to the alerts and route tickets to people who can resolve them (e.g., service techs). FIG. 2 depicts an embodiment of a scent management system 200 that enables remote control, monitoring and management of scent devices from a central NOC. In this embodiment, enterprise applications 202 for workflow, analytics, and support as well as consumer apps 204 for mobile and web control may interface with the NOC software 208, which may run in the NOC 118. The enterprise application 202 may run on a NOC user device 114. The consumer apps, such as a customer control app, may run on a consumer control device 120. The NOC software 208 may include features such as virtualized device services, web service APIs, a real-time alert engine, distributed data storage, data rate services, account management, a firmware upgrade manager, secure networks and date, and a scalable cloud architecture. In this embodiment, the NOC 208 communicates via WiFi or a cellular internet gateway with diffusion devices 210 which themselves may be locally networked, such as Zigbee networked. FIG. 3 depicts an embodiment of enterprise architecture 300. In this embodiment, the architecture 300 includes a billing & financials facility 302 that receives billing & payables data from a device management facility 308, an inventory management facility 304 that interfaces with the device management facility 308 for the purposes of exchanging information on new devices, repairs, and replacements, a NOC 118 for monitoring diffusers 102, 104 through the device management facility 308, a ticketing & workflow facility 310 that interfaces with the NOC 118, the device management facility 308, and the service tech interface 314 for creating and managing tickets for service staff, a customer interface 312 for viewing diffuser status and adjusting settings, and a service technician interface 314 to receive service requests and update status, install and service diffusers.

Figure 6:
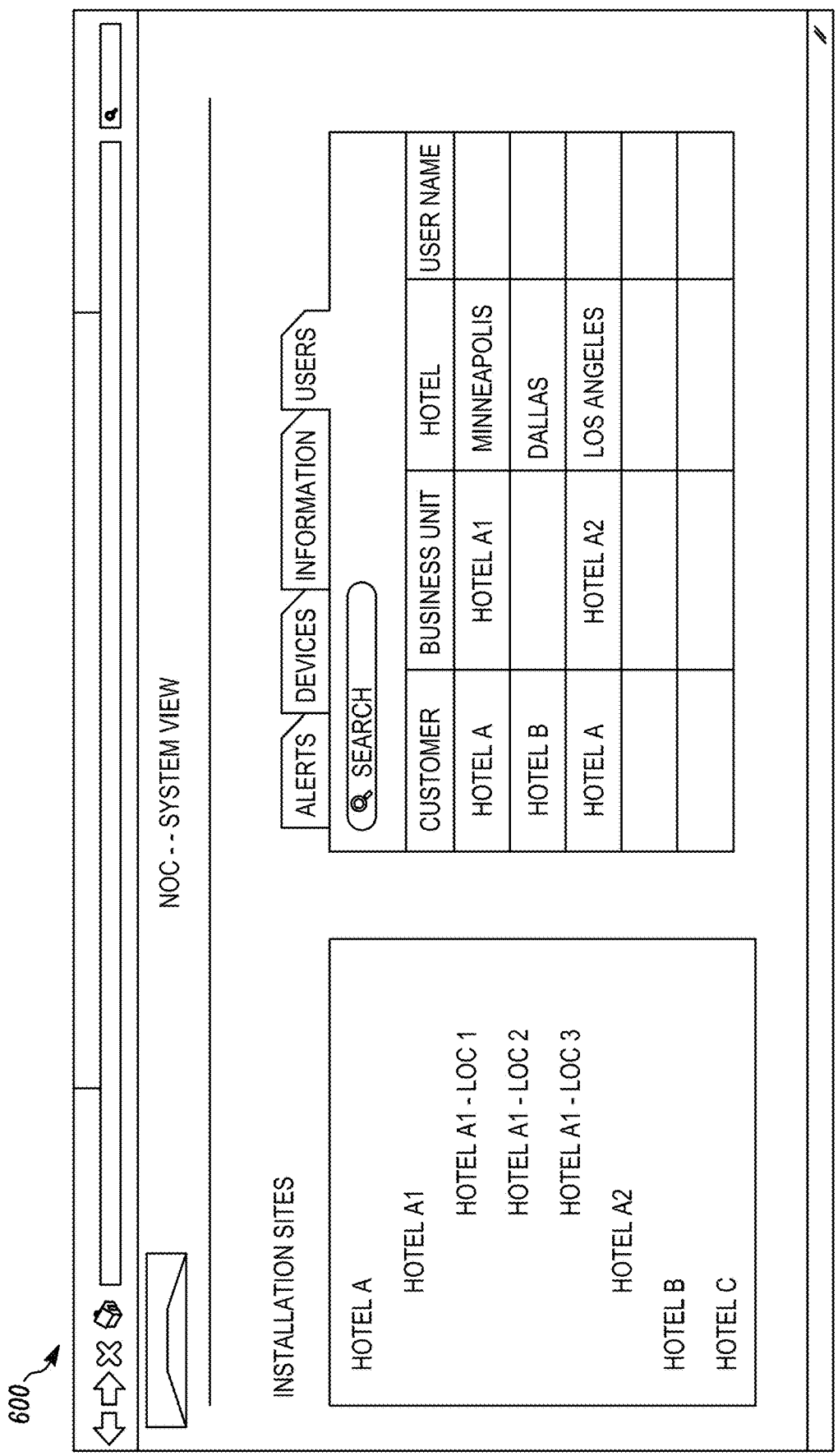
FIG. 6 depicts an exemplary embodiment of a NOC system view.
Figure 7:
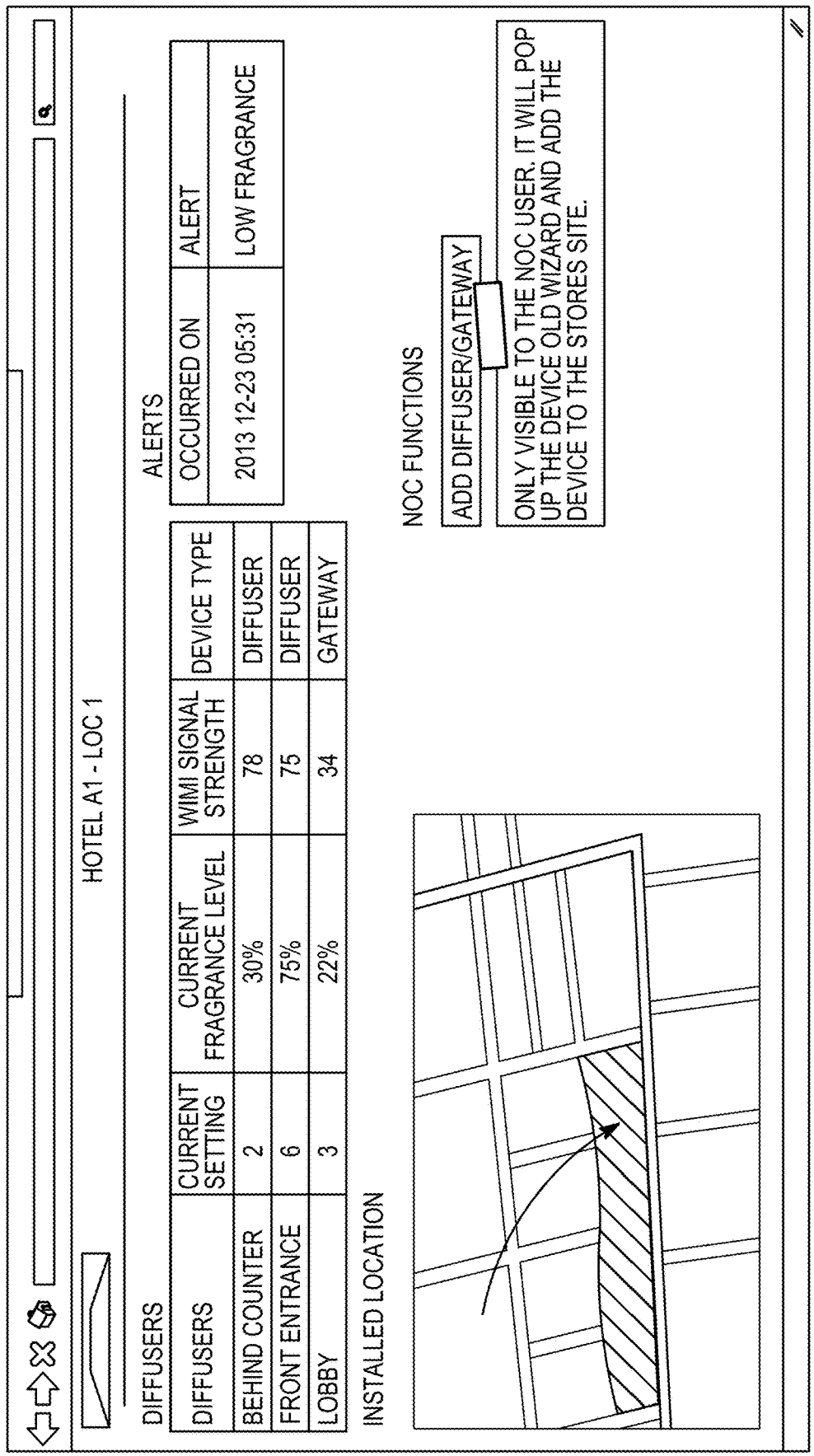
FIG. 7 depicts an exemplary embodiment of a location overview.
Figure 8:
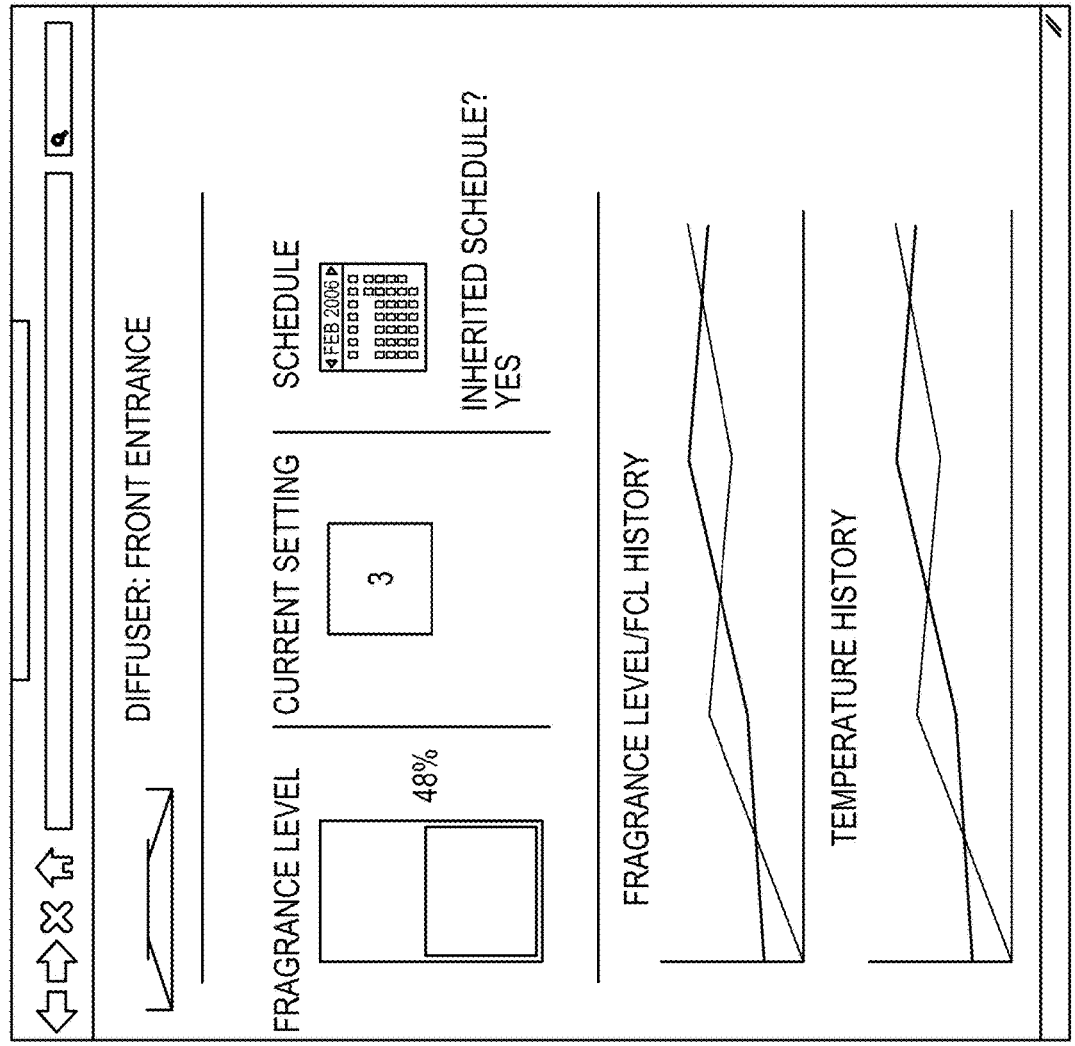
FIG. 8 depicts an exemplary embodiment of diffuser data.

For example, system administrators in the NOC are able to, among other things, review status data received from devices within the scent dispersion network, control the program settings of all networked scent devices, identify performance problems within scent dispersion networks, schedule the replenishment of fragrance cartridges, and schedule the maintenance, repair or replacement of malfunctioning networked scent devices. The NOC administrators are able to accomplish such tasks manually by reviewing status data and making changes in real time, or by allowing the NOC software to automatically take action to maintain and support scent dispersion network based on pre-established rules and heuristics. FIG. 6 depicts an exemplary embodiment of a NOC system view 600. In this view, tabs are visible for alerts, devices, information, users, and a search window. An installation sites window lists sites by parent company (e.g. Hotel A, Hotel B, Hotel C), sites that are subsidiary or otherwise associated with the parent (e.g. Hotel A1, Hotel A2), and yet further sites associated the secondary level of the company hierarchy (e.g. Hotel A1-Location 1, Hotel A1-Location 2, Hotel A1-Location 3). In this figure, the user tab is exposed indicating who is a contact point for the installation. FIG. 7 depicts an exemplary embodiment of an overview 700 of diffusion devices at a particular location. In this example, the diffusers are listed, a map with a location of the sites is shown, alerts are shown, and any NOC-specific functions, such as adding a diffuser or gateway, may be shown. For the diffuser listing, information such as a current setting, a current fragrance level, a WiMi signal strength, and a device type may be shown along with any other diffuser or sensor data. Each diffuser may be selected so that the user can drill down on specifics for that diffuser. FIG. 8 depicts an exemplary embodiment of a view of a "drill down" 800 to diffusion device data. Current fragrance level, current setting, a schedule, a fragrance level/FCL (fragrance concentration level)/SCF (scent concentration factor) history, and a temperature history may be shown as well as any other diffuser or sensor data.

In an embodiment, a user interface for a network of scent diffusion devices may include a device management & monitoring (DM&M) facility that includes configurable dashboards to enable a plurality of activities for the network of scent diffusion devices, and a security facility to set one or more permissions for the activities. The activities may be at least one of viewing diffusion device telemetry data, maps of diffusion device locations, receiving liquid level readings or other gauge/sensor readings, providing control instructions to diffusion devices, reviewing status of and managing scent operations for one or more networks of scent diffusion devices, receiving data and status information from devices, generating and viewing reports, adjusting device settings, viewing historical graphs showing the performance of the devices, receiving alerts, configuring alert triggers, viewing and editing schedules and scent profiles, viewing unitless parameters for articulating and displaying a fragrance level, reviewing alerts to replace packages, ordering and paying for new packages, renewing subscriptions for scent management services, reviewing system health (e.g. machine down alerts), changing permissions for a user, initiating a ticket/workflow, assigning a service technician, adding or removing a device from a network, and adding a customer/division/store. A mobile application may be used to access the user interface. The user interface may further include a scheduling facility to indicate when a service is scheduled to occur in an environment and allowing a user to select a scent to be diffused in the environment that complements the scheduled service. The alerts may be based on various criteria and configurable conditions (e.g., low liquid, machine down, etc.). Viewing and editing schedules and scent profiles may be done for one or more diffusion devices independently of one another. Adjusting device settings may involve the user increasing or decreasing the overall output of all diffusion devices in the location and allowing a NOC to calculate and adjust the settings for each diffusion device needed to achieve the overall location volume setting.

In an aspect, a method of managing scent in an environment may include disposing one or more scent diffusion devices within an environment, wherein the scent diffusion devices comprise a communications facility that enables transmitting signals to and receiving signals from a remote computer, receiving at least one scent parameter for scenting an environment at the remote computer, and controlling, via the remote computer, at least one of the scent diffusion devices to achieve the scent parameter. Controlling may include adjusting an operation parameter of the scent diffusion device in response to a sensed fragrance level in the environment.

Referring to FIG. 9, a method for operating atomizing diffusion devices within an environment may include receiving at a computer, liquid level data from a plurality of remote atomizing diffusion devices wherein each diffusion device comprises a communications facility that enables transmitting signals to and receiving signals from a remote computer and at least one liquid level sensor, and based on the liquid level data 902, creating, via the remote computer, an electronic data structure characterizing the transformation of the remote diffusion devices, wherein the electronic data structure includes data specifying at least one of the production of scent fragrance, the procurement of scent fragrance, the management of scent inventory, the delivery of scent inventory 904, and causing the remote atomizing diffusion devices to implement the transformation 908.

In another aspect, a method of managing scent in an environment may include disposing one or more scent diffusion devices within an environment, wherein the scent diffusion devices include a communications facility that enables transmitting signals to and receiving signals from a remote computer. The method may further include disposing at least one sensor within the environment that transmits sensor data to the remote computer and receiving at least one scent parameter for scenting the environment at the remote computer. The method further includes controlling, via the remote computer, diffusion of a liquid from a source of the liquid that is in fluid communication with at least one of the scent diffusion devices to achieve the scent parameter. In embodiments, it is not diffusion of a liquid but diffusion of a gas. Controlling may include setting or adjusting an operation parameter of the scent diffusion device in response to the sensor data. The sensor data may relate to static parameters or dynamic parameters, such as room volume, room geometry, room area, airflow, presence of odor-producing materials, presence of odor-sinking factors, lighting, air flow, altitude, traffic flow, occupancy detection (e.g. IR, camera, $CO_2$ sensor), proximity sensing, detected odor, fragrance level, scent concentration factor, temperature, humidity, time of day, season, weather event, detection of a VIP/specific individual entering the space, such as via a smartphone ping, and the like. In certain embodiments, the scent diffusion device(s) may be configured at installation to a baseline configuration, based on the static parameters of the installation site. Then, the device would intelligently adjust output of scent, based on algorithms that adjust for dynamic parameters or time-changing conditions. Certain static parameters include room volume, room geometry, room area, and altitude. With respect to room volume, volume calculations may be performed based on measurements taken of the room, for example, using a tape measure or a laser distance meter, and then adding the volume data into a data structure which characterizes the space in which the diffuser is deployed. This may be done at device installation to establish the baseline settings for the Scent Concentration Factor. With respect to room geometry, geometry may be determined by taking into account entries, exits and other areas of people movement, as well as from floor plans. Room area may be calculated based on sensor measurements of linear distance between walls. With respect to altitude, the diffusion devices may have a proximity detection capability based on cell phone technology, which allows the device to "know" where it is located, for example at a specific longitude and latitude. Given the long-lat information, the networked device can inquire from a remote database the specific altitude of the location where it is located. This altitude information is then used to adjust device performance, so for example, a lower setting of scent diffusion would be used at high elevations with "thinner" air, while a higher level of scent diffusion would be used at lower elevations with "thicker" air.

Dynamic parameters include the presence of odor-producing materials, presence of odor-sinking factors, lighting, air flow, traffic flow, occupancy detection (e.g. IR, camera, $CO_2$ sensor), proximity sensing, detected odor, fragrance level, scent concentration factor, temperature, humidity, time of day, season, weather event, detection of a VIP/specific individual entering the space, and the like.

With respect to airflow, a sensor technology may measure the mass of air flowing through a device (typically a tube) per unit time. The airflow sensor may be a flow or pressure differential sensor, or switch, or transducer. For a fixed airflow HVAC system, the air flow sensor may be in the form of a switch, which indicates whether air flow is occurring or not, above a certain threshold. That information would be used to turn "on" the scent diffuser when air is flowing, and turn "off" the scent diffuser when air is not flowing. For a variable airflow HVAC system, the airflow sensor may provide an analog voltage reading, which indicates the actual level of air flow. This analog signal may be used to automatically adjust the diffuser output, based on the level of air flow. In such a way, the device is able to increase scent diffusion when air flow is high and lower it when air flow is low (or stop when air flow is "off")

With respect to the presence of odor-producing materials, semiconductor sensors may identify air born scent particles, wherein such sensors may be "tuned" to specific scents. The receptors of these sensors may be able to identify the shape of a scent molecule, or alternatively, are "tuned" to a certain quantum effect of the scent molecules such as its level of vibration. Based on the detection of certain known malodors within an environment, the diffusion device can change its level or scent or conversely can add a secondary odor remediation or neutralization diffusion which counteracts the malodor. In the case of the two-cartridge system, one cartridge contains the desired scent fragrance, while the second cartridge contains the odor remediate/neutralizer, which would be diffused according to a pre-programmed response, once a certain malodor is detected.

With respect to the presence of odor-sinking factors, certain types of molecules will interact with or bind to scent particles, causing them to drop out of circulation. These odor-sinking factors can be identified in much the same way as previously described for malodors, allowing the diffusion device to follow a pre-programmed algorithm in response to the presence of the odor sinking factor.

With respect to lighting, photodetectors are devices that can sense the presence of photons. There are a variety of well-known and commercially available technologies which enable photo-detection, and some which also are "tuned" to detect and measure the relative amount of certain types of photons, which have characteristic wavelengths (red, blue, etc. in the visible spectrum of lights). The diffusion device has data inputs that enable it to respond to the detection or absence of light, such as, to turn off scent diffusion when no light is detected. Similarly, lighting systems in theatrical productions can be used to control the scent diffusers, so that the networked scent diffuser will follow the programmatic direction of a lighting control system.

With respect to traffic flow, people detectors are sensors that can count the number of times a person has walked past a specific point. One detector is a photoelectric sensor, which detects the number of times a beam of light, which is placed across a space, is broken or intercepted by a person walking past. Another detector is an image or video camera, which uses image processing techniques to determine the number of people in a space, as well as their individual dwell times. The diffusion device can take information from a traffic flow sensor and automatically adjust its scent diffusion, for example, by scenting an area as people are arriving, or increasing the scent level to accommodate a larger traffic throughput.

With respect to occupancy detection, these sensors can confirm the presence of one or more individuals within a space. One approach includes an image or video camera that uses image processing techniques to determine the number of people in a space, as well as their individual dwell times. The diffusion device can take information related to occupancy and automatically adjust its scent diffusion, for example, by providing more scent to an area with more as people, or stopping scent from diffusion in an unoccupied room and then beginning diffusion of fragrance upon the arrival of people.

With respect to proximity sensing, proximity sensors are triggered when a person is directly in front of a particular space, such as in front of a particular product display. By sensing the presence of a person at that space, the diffuser is able to provide a scent experience, coordinated with the presentation of the product in the display.

With respect to detection of a VIP/specific individual entering the space, cameras with facial recognition software can determine the presence and identity of an individual or individuals, whose facial profiles have been pre-loaded for comparison. In another embodiment, the VIP/specific individual may be detected via detection of their smartphone. The presence of specific people can therefore be communicated to the device from these sensors, allowing the scent diffusion device to alter its performance.

With respect to fragrance level, by "tagging" a desired scent fragrance with a molecular tag, such as a charged particle, a sensor may be able to identify and determine the concentration of the "tagged" scent particles within a space. The diffusion device can be set to deliver a certain level of scent concentration within an environment, and using odor detection of the scent particles which the diffuser is dispensing, can ensure a defined range of acceptable scent level, or "scent concentration factor" or SCF. When the sensor detects odor concentrations below the desired SCF, then the diffuser delivers additional fragrance to achieve the desired concentration. If the measured concentration is within the defined SCF, then the diffuser continues monitoring without diffusion. If the concentration is above the SCF, the diffuser can continue monitoring without diffusion, or can diffuse an odor sinking formulation which binds with airborne scent and thereby reduces the scent level to within the desired SCF range.

With respect to temperature, the scent diffuser may have multiple ways of measuring temperature. Internal temperature within the diffusion device is measured using a thermistor that is present in the electronics of the device. This thermistor allows the device to communicate the internal temperature to a remote monitoring center, which can be alerted if internal temperature exceeds a prescribed threshold such as its recommended operating range of temperature. Similarly, with remote monitoring, the device can be pre-programmed to take certain action under certain temperature condition, such as, stop dispensing fragrance oil if the temperature is above its operating threshold, or below the freezing point of the scent oil. External temperature may be measured based a thermal sensor (thermistor) mounted on the exterior of the device, allowing the diffuser to alter its performance based on changing temperatures within the environment which is being. The temperature of the exterior climate can be retrieved from a remote data structure, based on the geo-code location of the device using its network connectivity. The diffuser can react to the exterior temperature of the environment, by diffusing alternate fragrances, or by altering the scent concentration. With all three forms of temperature measurement and tracking data across diffusers using the remote monitoring capability of the devices, one can determine the statistical correlation of temperature to other performance trends, for example, oil consumption rate over time.

With respect to humidity, a humidity sensor installed within a device can detect internal device humidity, one on the exterior of the device can determine environmental humidity within the space being fragranced, and geocode and remote data lookups can be used to retrieve the humidity of the local climate. The scent device can react to changes in these humidity levels similarly as described for temperature. Similarly, over time, remote monitoring can be used to evaluate and correlate trend data, such as how humidity affects the consumption rate of scent oil within a diffuser.

With respect to time of day, the diffusers are smart, connected devices, and consequently, accurately know the time. Based on the geolocation data from the cell phone modem (or network id) of a diffuser in a the scented environment, the device can accurately set its clock to the correct local time zone, and automatically adjust for seasonal adjustments in time, with the goal of keeping the diffuser unit in time-sync with the world clock. Since the scent diffuser devices have the ability to change fragrance output or fragrance type based on scent programs or play lists, it is critical that the device has an accurate representation of its current time.

With respect to season, the diffuser has the ability to accurately tell time as well as know the current day, week and year, using the same approach as described above. Using this knowledge of time, it can be programmed for different performance on different days or in different seasons of the year.

With respect to a weather event, since the diffuser is smart and connected, local weather conditions can be downloaded to the device based on its geo-location. Based on these local weather conditions, the diffusing device can alter its performance based on a predefined set of rules.

The scent diffusion device may include at least one package containing a fragrance oil or at least two packages containing a fragrance oil. In embodiment, one of the scent diffusion devices is a master node and the other of the scent diffusion devices are slave nodes and receive control instructions from the computer through the master node. In this embodiment, each scent diffusion device can adjust its own control settings based on the activities of the other scent diffusion devices. The method may include configuring the scent diffusion devices so that a device duty cycle for one of scent diffusion devices does or does not occur simultaneously within proximity to another one of the scent diffusion devices. The scent parameter may relate to a brand management goal. The method may further include determining the total number of scent diffusion devices to dispose in the environment based on a room volume. The method may further include determining one or more locations to dispose the scent diffusion devices in the environment based on a room volume. The operation parameter may include at least one of a flow rate of the liquid, a duration of flow of the liquid, a variation in the flow rate of the liquid, an on/off status of the diffusion device, a package from which to diffuse the liquid, a switch to a different package from which to diffuse the liquid, and the like.

In another exemplary use scenario, the scent dispersion network includes one or more scent node devices and a wide-area network gateway device. In this scenario, the network gateway device performs the communication and control functions of the scent gateway device, without actually dispersing fragrance. In this scenario, system administrators in the NOC control the program settings of all networked scent devices, and ensure fragrance dispersion is conforming to commercial brand standards or other parameters. This scenario provides remote and centralized management of a scent dispersion network via a network gateway device that does not dispense fragrance.

In an aspect, a method of managing scent in an environment may include disposing one or more scent diffusion devices within an environment, wherein the diffusion devices comprise a communications facility that enables transmitting signals to and receiving signals from a non-fragrance dispensing, wide-area network gateway device. The method may further include networking the network gateway device to the scent diffusion devices, wherein the network gateway device receives communication and control functions from a remote computer for distribution to the scent diffusion devices. At least one sensor disposed within the environment may transmit sensor data to the remote computer. At least one target value of a scent parameter for an environment may be received at the remote computer. The method may further include controlling, via the remote computer, diffusion of a liquid, from a source of the liquid in fluid communication with at least one of the scent diffusion devices, to achieve the target value of the scent parameter, wherein controlling includes setting or adjusting an operation parameter of one or more of the scent diffusion devices based on the sensor data. In embodiments, it is not diffusion of a liquid but diffusion of a gas. At least one of the scent diffusion devices receives control instructions from the remote computer and relays control instructions to at least one other scent diffusion device. The scent diffusion devices may relay control instructions in series, in a ring, in a mesh, in a star networking topology, and the like.

In another exemplary use scenario, the scent dispersion network includes one or more scent node devices, a local area network control device, but without a wide-area network gateway device. Each scent node device is paired with a local area network control device, which enables a local user within a venue to program and control the scent node devices independently of a NOC (local control, versus centralized remote control). This scenario enables local management of a scent dispersion network via wireless local area network communication protocols. Examples of local area network control devices include a computer or laptop with wireless local area network communication capability; a smart phone, pad device, or tablet computer with wireless local area network communication capability; or a purpose built scent controller device with wireless local area network communication capability. In embodiments, the scent controller device may be a handheld or wall-mounted device for controlling one or more networked scent diffuser devices.

In an embodiment, a method of managing scent in an environment, may include disposing at least one scent diffusion device within an environment, wherein the at least one scent diffusion device comprises a communications facility that enables transmitting signals to and receiving signals from a standalone remote control device, receiving at least one target value of a scent parameter for the environment at the standalone remote control device, and based on the target value, controlling, via the standalone remote control device, diffusion of a liquid from a source of the liquid in fluid communication with the at least one scent diffusion device to achieve the target value of the scent parameter. In embodiments, it is not diffusion of a liquid but diffusion of a gas.

In an aspect, a method of managing scent in an environment may include disposing one or more scent diffusion devices within an environment, wherein the diffusion devices comprise a communications facility that enables transmitting signals to and receiving signals from a local area network control device and networking the local area network control device to each of the scent diffusion devices, wherein the local area network control device receives communications from and distributes control instructions to the scent diffusion devices. The method may further include disposing at least one sensor within the environment that transmits sensor data to the local area network control device, receiving at least one scent parameter for scenting an environment at the local area network control device, and controlling, via the local area network control device, the diffusion of a liquid or gas, from a source of the liquid in fluid communication with at least one of the scent diffusion devices, to achieve the scent parameter, wherein controlling includes setting or adjusting an operation parameter of one or more of the scent diffusion devices in response to the sensor data. The local area network control device may include one or more of a computer or laptop with wireless local area network communication capability, a smart phone, a pad device or tablet computer with wireless local area network communication capability, a purpose built scent controller device with wireless local area network communication capability, a handheld device, a wall-mounted device, and the like.

In yet another exemplary use scenario, the scent dispersion system includes one or more scent node devices, with no wide-area network gateway device and no local area network control device. This scenario provides for the stand-alone operation of a scent node device using manual settings, established by a local individual using the user interface found on each fragrance dispersion device.

In embodiments, multiple master devices may be deployed at a single physical location. In embodiment of multi-device installs (master-slave configuration), each device can adjust its own control settings based on the activities of the other devices. The system may be a coordinated network of devices with "local scent network" level control mechanisms versus device stand-alone control mechanisms. For example, a group of meshed dispensers could be configured so that individual device duty cycles do not occur simultaneously within proximity to one another (one device waits for the previous one to dispense, so they do not end up overloading an area with multiple scent devices "firing" at the same time). Of course, they may also be configured to fire simultaneously. In effect, coordination, sequencing, and/or synchronization of meshed scent devices is controlled dynamically.

In an embodiment, the number and location of scent diffusion devices within an enclosed space may be established based on the volume of the space but the individual control programs for those devices may be based on something other than the volume of the space, such as a sensor reading, an area, a linear distance from the device to a target, and the like. In embodiments, the initial settings for the diffusion devices may be established in one manner, such as by using room volume, but then may switch over to control via a different mechanism, such as by environmental adjustments or rate of consumption measurements, and the like.

In an embodiment, the diffusion devices may operate in a scent-casting mode, wherein the devices are programmed with a linear distance to a scent target location and the level of fragrance that should be at that target location. Further considerations may include airflow and tonnage of an HVAC system when programming a scent-casting mode. In a scent-casting mode, the goal is not to fill the space with fragrance, but rather scent a targeted area or audience with the scent brand impression.

In an aspect, a method of scent casting in an environment may include disposing a scent diffusion device within an environment, wherein the scent diffusion device comprises a communications facility that enables transmitting signals to and receiving signals from a remote computer, determining a distance from the scent diffusion device to a scent target location, receiving, at the remote computer, at least one scent parameter for the scent target location, and controlling, via the remote computer, the scent diffusion device to achieve the scent parameter, wherein controlling includes setting an operation parameter of the scent diffusion device based on the determined distance and the scent parameter. The method may further include disposing at least one sensor within the environment that transmits sensor data to the remote computer, and adjusting an operation parameter of the scent diffusion device in response to the sensor data. The sensor data may relate to at least one of room volume, room geometry, room area, airflow, presence of odor-producing materials, presence of odor-sinking factors, lighting, air flow, altitude, traffic flow, occupancy detection (IR, camera, $CO_2$ sensor), proximity sensing, detected odor, fragrance level, temperature, humidity, time of day, season, weather event, and detection of a VIP/specific individual entering the space (via smartphone ping or the like). The method may further include adjusting an operation parameter of the scent diffusion device in response to an HVAC tonnage.

Scent casting in an environment may be accomplished using a network of diffusion devices, such as scent diffusion devices. A network of diffusion devices may be disposed within an environment that each includes a communications facility enabling that transmission of signals to and the reception of signals from a remote computer. One such received signal may be a scent parameter for a scent target location. A distance from the diffusion devices to the scent target location may be determined by any means available for such determination. Via the remote computer, the network of diffusion devices may be controlled to achieve the scent parameter. Controlling may include setting an operation parameter of the diffusion devices based on the determined distance and the scent parameter.

Scent casting may also be implemented using a hotspot in an environment. Such a diffusion device may include a sensor to determine a distance from the diffusion device to a scent target location and a first communications facility 1022 that receives control signals from a network operations center, the control signals for controlling a scent diffusion from the diffusion device in accordance with a scent impression goal and the distance. The device may also include a second communications facility 1024 to communicate data with a mobile device at the scent target location for consumer engagement, such as to provide consumers with a coupon, an ad, a survey, a game, or other content.

A ticketing & workflow facility of the NOC may receive alerts from the device management and monitoring system and create tickets. Tickets may be routed, based on rules, to the correct person, or in some cases, rules might automatically trigger some action (e.g., shut down a device that is misbehaving, or reboot a device). The ticketing & workflow facility may be a configured version of a commercial service ticketing system.

Managed, networked diffusion devices, where the device is agnostic to the actual diffusion technology, may be used for generating a consistent scent profile in a wide area/ambient environment in accordance with brand standards or other parameters. In an embodiment, generating the consistent scent profile involves consistently neutralizing a malodor in an environment. Generating a consistent scent profile may include management of duty cycle, schedule, fragrance level/fragrance replenishment, room volume, room geometry, airflow, presence of odor-producing materials, presence of odor-sinking factors, lighting, temperature, humidity, altitude, traffic flow, occupancy, time of day, inventory of particular "base," "mid-" and "high" notes in a fragrance chord and other variables relating to the environment. As such, data collected by or about the device, data based on measurements by sensors on or associated with the device, and data from users may be transmitted to, generated, or used by the NOC in order to facilitate management. These data will be described herein.

Certain data types may be sent from the diffusion devices to the NOC or other user. Data regarding a work schedule, such as duty cycle, day parts, and the like, may be sent by the diffuser. Object type, such as the type of diffuser (e.g.

Master, Slave, standalone), may be transmitted by the diffuser. The diffusion device may transmit the fragrance name(s) and level(s). For example, the fragrance level may be a value from 0 to 100, with 100 being full and 0 being empty. The temperature, in Fahrenheit, Celsius or other units, as well as date and time may be transmitted. The diffusion device may send an indication of the strength of the local wireless link. An array of any error codes that are currently present on the device may be transmitted. The diffusion device may transmit the average pump pressure.

The diffusion device may report diagnostic data on a periodic basis, such as weekly/daily, or by forcing the diffusion device into a diagnostic mode, such as via a local keypad or controller, or from the NOC. Data usage may be reported by Master devices, such as cellular data usage.

In an embodiment, a device management & monitoring (DM&M) facility may be embodied in a user interface that may include configurable dashboards to enable activities, such as viewing diffusion device telemetry data, viewing maps of diffusion device locations, receiving liquid level readings or other gauge/sensor readings, providing control instructions to diffusion devices, review status of and manage scent operations for one or more networks of scent diffusion devices, receive data from devices, receive alerts, view/edit schedules and scent profiles, view unitless parameter for articulating and displaying a fragrance level, review alerts to replace packages, order new packages and pay on-line, renew subscriptions for scent management services, review system health (e.g. machine down alerts), change permissions for a user, initiate a ticket/workflow, assign a service technician, add/remove device from a network, add customer/division/store, and the like. In embodiments, a mobile application, such as a smartphone or tablet application, may allow customers to access a mobile version of the user interface.

The user interface may be used to set up and trigger alerts based on various criteria and configurable conditions (e.g., low liquid, machine down, etc.), wherein the NOC may manage the system by exception based on detected alarms. The user interface may allow customers to view the status of their diffusion devices, adjust their settings, or view historical graphs showing the performance of the devices. The user interface may take data from DM&M and present it in a way that uses the language of fragrance, rather than of devices (e.g., MAC Address, PAN number). In embodiments, the DM&M facility may be responsible for all communication with diffusion devices and may be the only module that can change diffusion device settings. In other embodiments, WiFi capabilities may be included in the master diffusion device enabling a direct connection to the device.

The user interface may be used to manage and edit the schedules for one or more diffusion devices independently of one another. That is, there is the ability for different diffusers at a single site to have different schedules.

A reports page may be used to generate and access reports. An "about page" or introductory page may tell the user about the version number of the application, as well as the version number and device types of the various devices.

The user interface may include a login screen for entering the user's User ID and password and authenticating it. The user interface may include a dashboard page that shows the status of all local diffusion devices at a summary level. A visual icon representing each diffusion device with an indicator for function or status may be included in the dashboard. The user interface may include a diffusion device page that includes a list of diffusion devices at the location, with summary status and settings (e.g., volume setting, overall diffusion device health, whether it's currently diffusing or not based on duty cycle, status of communications links, and the like). Icons for each diffusion device may be presented. A diffusion device status page may be a drill-down page that shows all device status data and settings, such as overall diffuser health (good, or error+error code and description), diffuser volume/output-level setting (according to program), diffuser volume/output-level setting (according to setting by local customer, possibly overriding the program), liquid fragrance level (based on the sensor reading), time and date according to device clock, health of communication links between various devices and the local server, which fragrance is playing/being diffused in the diffuser, date and time of last service, and the like. An edit diffusion device settings page may be a page where a user can edit a diffusion device's settings and save the new settings, including the on/off program settings, and the fragrance volume level.

A location control page may allow the user to increase or decrease the overall output of all diffusion devices in the location. For example, an algorithm, such as a location control algorithm, may execute a calculation that translates a targeted fragrance value (also known as a local output level) (e.g., between 0-100, between 0-10, etc.) in the location to actual device settings for each diffusion device. The user would adjust only the overall location volume setting, not the settings for each diffusion device. The NOC would then calculate and adjust the settings for each diffusion device needed to achieve the overall location volume setting. The local output level represents the output level aggregated across all diffusers. The user interface may present graphical arrows for moving the output level up or down. The master diffusion device may adjust its own output level and the output level of its slaves upward or downward, proportionately based on the new setting. If all diffuser settings were the same, the new settings will all be the same, but if the diffusers had different output settings, the new settings may be scaled based on each diffuser's original setting. As an example, the current output level might be 70, based on 3 diffusers whose output settings are 65, 70, and 75. If the user moves the output level to 80, the new settings may be the original settings multiplied by (80−70)/70, resulting in settings of 74.28, 80, 85.71, respectively. The above calculations may be done by customer web services or the NOC and pushed to the individual diffusers.

The location control algorithm may include feedback from one or more sensors in the environment or onboard the diffusion device in making the calculations, such as feedback from a Bluetooth/WiFi sensor (e.g. to determine an occupancy), a different occupancy sensor, an altitude sensor, an airflow sensor, a humidity sensor, a light sensor, a motion/occupancy/proximity sensor, a laser distance measure/digital laser rangefinder, a particle sensor, an olfaction sensor/VOC sensor, an imaging sensor/cameras, a scent concentration factor sensor, a clock, a timer, a calendar, a weather sensor, and the like. Modification or generation of a scent profile delivered by a network of scent diffuser devices may be based on one or more sensed parameters, wherein modifying the scent profile is done by selection of or adjustment of the diffusion settings for one or more available fragrances onboard one or more networked scent diffuser devices. The sensed parameter may be at least one of room volume, room geometry, airflow, presence of odor-producing materials, presence of odor-sinking factors, lighting, air flow, altitude, traffic flow, occupancy detection (IR, camera, CO2 sensor), proximity sensing, detected odor, fragrance level, temperature, humidity, time of day, season, weather event, detection of a VIP/specific individual entering the space (via smartphone ping or the like), and the like. In embodiments, the scent profile is a neutralization of a malodor and the fragrance includes an odor neutralizer. Modification or generation of a scent profile delivered by a network of scent diffuser devices may be based on feedback from automated air sampling, wherein modifying is by selection of or adjustment of the diffusion settings for one or more of a plurality of available scent modifiers onboard one or more networked scent diffuser devices. A user may adjust an overall level of fragrance desired in the space and the NOC or the master diffuser device may determine the adjustment required for the one or more devices, such as slave diffuser devices. A master diffuser device may adjust its own output level and the output level of its slaves upward or downward, proportionately based on the new setting. In an embodiment, the automated air sampling may be automated malodor sampling and identification, the scent profile may be a neutralization of a malodor and the scent modifier is a neutralizer or fragrance. Adjusting the settings may include selection of a best-fit neutralization/fragrance for dealing with the malodor and determination & execution of a dispersal profile for the neutralizer/fragrance that is needed to neutralize or counteract the malodor.

In an embodiment, a method may include disposing at least one sensor within the environment that transmits sensor data to a remote computer, receiving at least one target value of a scent parameter for the environment at the remote computer, and based on the sensor data, controlling, via the remote computer, diffusion of a scent from at least one scent diffusion device to achieve the target value of the scent parameter, wherein controlling includes setting or adjusting an operation parameter of the at least one scent diffusion device in response to the sensor data.

In an aspect, a method may include receiving at least one remotely sensed scent parameter for an environment at a remote computer 1402, and based on the sensed scent parameter data, controlling, via the remote computer, diffusion of a scent from at least one scent diffusion device in the environment to achieve a target value of the scent parameter, wherein controlling includes at least one of setting and adjusting an operation parameter of the at least one scent diffusion device in response to the sensed scent parameter data 1404. The sensed parameter may relate to at least one of room volume, room geometry, room area, airflow, presence of odor-producing materials, presence of odor-sinking factors, lighting, air flow, altitude, traffic flow, occupancy detection (IR, camera, CO2 sensor), proximity sensing, detected odor, fragrance level, temperature, humidity, time of day, season, weather event, and detection of a VIP/specific individual entering the space (via smartphone ping or the like). The scent diffusion device may include at least one package containing fragrance oil or at least two packages containing fragrance oil. One scent diffusion device may be a master node and the other scent diffusion devices may be slave nodes and control instructions are sent from the remote computer through the master node. At least one of the scent diffusion devices receives control instructions from the remote computer and relays control instructions to at least one other scent diffusion device. In this scenario, the scent diffusion devices may relay control instructions in series, in a ring, in a mesh, in a star networking topology, or the like. Each scent diffusion device may adjust its own control settings based on the activities of the other scent diffusion devices. The method may further include configuring the at least one scent diffusion device so that a device duty cycle does or does not occur simultaneously within proximity to another scent diffusion device. The scent parameter may relate to a brand management goal. The method may further include determining the total number of scent diffusion devices to dispose in the environment based on a room volume. The method may further include determining one or more locations to dispose the scent diffusion devices in the environment based on a room volume. The operation parameter may include at least one of a flow rate of the liquid, a duration of flow of the liquid, a variation in the flow rate of the liquid, an on/off status of the diffusion device, a package from which to diffuse the liquid, and a switch to a different package from which to diffuse the liquid.

In an embodiment, a method may include sampling the air in an environment to determine the presence of a malodor according to an automated sampling program, selecting at least one of a neutralizer and a fragrance for a network of scent diffusion devices to diffuse to counter the malodor, and adjusting an operation parameter of the network of scent diffusion devices in response to the malodor to diffuse the selected neutralizer or fragrance. Determining may involve measuring an electrostatic charge. A user may adjust an overall level of odor desired in the space and a scent diffusion device controller may determine the adjustment required for the one or more devices. Adjusting may involve a master diffusion unit of the network of scent diffusion devices adjusting its own output level and the output level of its slaves upward or downward, proportionately based on the adjusted operation parameter. The method may further include repeating the step of sampling to determine the continued presence of the malodor, and terminating the operation of the network of scent diffusion devices if the malodor is no longer present. Adjusting may involve altering a duty cycle of the scent diffusion device. The method may further include selecting both of the neutralizer and the fragrance; and selecting a mix ratio for the two.

In an aspect, a method may include sampling the air in an environment to determine the presence of a malodor according to an automated sampling program, selecting at least one of a neutralizer and a fragrance for a scent diffusion device to diffuse to counter the malodor, adjusting an operation parameter of the scent diffusion device in response to the malodor to diffuse the selected neutralizer or fragrance, and communicating the adjustment to other scent diffusion devices in a network of scent diffusion devices. Determining may include measuring an electrostatic charge. Adjusting may include a master diffusion unit of the network of scent diffusion devices adjusting its own output level and the output level of its slaves upward or downward, proportionately based on the adjusted operation parameter. The method may further include repeating the step of sampling to determine the continued presence of the malodor, and terminating the operation of the network of scent diffusion devices if the malodor is no longer present. Adjusting may include altering a duty cycle of the scent diffusion device. The method may further include selecting both of the neutralizer and the fragrance; and selecting a mix ratio for the two.

In an embodiment, a sensor may be used to meter the environment for fragrance levels to provide feedback to a network of scent diffusion devices in order to continue generating a consistent scent profile in a wide area. In embodiments, this feedback enables the scent management system to operate in a closed loop. The sensor may be one or more of a particle sensor, olfaction sensor/VOC sensor, a scent concentration factor (SCF) sensor, a sensor that measures a proxy/tag dispersed with the fragrance, a sensor that measures an electrostatic charge, and the like. For example, a scent may be mixed with a tracer for diffusion into a space via one or more networked scent diffuser devices, wherein the tracer can be tracked throughout a wide area. Tracking may be used to confirm a fragrance in use, confirm that a fragrance is reaching its intended target, to determine the path of an individual who was initially in the space by detecting the tracer outside of the fragranced area, and the like. Various taggants may be used, such as odorless taggants. One taggant may be a perfluorocarbon tracer, such as taggants described in U.S. Pat. No. 5,409,839.

In an aspect, a method may include sampling the air in an environment to determine a fragrance level according to an automated sampling program, providing the fragrance level as feedback to a network of scent diffusion devices, and adjusting an operation parameter of the scent diffusion devices in response to the feedback, wherein adjusting enables the continued generation of a consistent scent profile in the environment. Determining may involve measuring a proxy/tag dispersed with the fragrance or an electrostatic charge. Adjusting may be by selection/adjustment of one or more of a plurality of available scent modifiers onboard one or more networked scent diffusion devices. A user may adjust an overall level of fragrance desired in the space and a scent diffusion device controller may determine the adjustment required for the one or more devices. Adjusting may involve a master diffusion unit of the network of scent diffusion devices adjusting its own output level and the output level of its slaves upward or downward, proportionately based on the adjusted operation parameter. The sampling may indicate the presence of a malodor and the operation parameter may be adjusted to provide a scent neutralization. Sampling may indicate the presence of a malodor and the operation parameter is adjusted to terminate diffusion of the scent.

In an embodiment, a method may include disposing an air sampling apparatus in an environment, drawing air to be sampled into the air sampling apparatus, and determining a level of a scent in the air using a sensor of the air sampling apparatus. The method may further include providing the sensor data as feedback to a network of scent diffuser devices in order to continue generating a consistent scent profile in a wide area.

In an aspect, a method may include sampling the air in an environment to determine a fragrance level according to an automated sampling program, providing the fragrance level as feedback to a scent diffusion device, adjusting an operation parameter of the scent diffusion device in response to the feedback, wherein adjusting enables the continued generation of a consistent scent profile in the environment, and communicating the adjustment to other scent diffusion devices in a network of scent diffusion devices. Determining may include measuring a proxy/tag dispersed with the fragrance. Determining may include measuring an electrostatic charge. Adjusting may be by selection/adjustment of one or more of a plurality of available scent modifiers onboard the device. A user may adjust an overall level of fragrance desired in the space and a scent diffusion device controller may determine the adjustment required for the one or more devices. Adjusting may include a master diffusion unit of the network of scent diffusion devices adjusting its own output level and the output level of its slaves upward or downward, proportionately based on the adjusted operation parameter. The sampling may indicate the presence of a malodor and the operation parameter may be adjusted to provide a scent neutralization. The sampling may indicate the presence of a malodor and the operation parameter may be adjusted to terminate diffusion of the scent.

In an aspect, a method may include sampling the air in an environment to determine a level of an airborne substance according to an automated sampling program, providing the level as feedback to a scent diffusion device, adjusting an operation parameter of the scent diffusion device in response to the feedback, wherein adjusting enables the continued generation of a consistent scent profile in the environment, and communicating the adjustment to other scent diffusion devices in a network of scent diffusion devices.

In an aspect, a method includes providing a sensed level of an airborne substance as feedback to a scent diffusion device 1502, adjusting an operation parameter of the scent diffusion device in response to the feedback 1504, wherein adjusting enables the maintenance of a scent profile in the environment, and communicating the adjustment to other scent diffusion devices in a network of scent diffusion devices 1508. When the substance is a fragrance, determining involves measuring a proxy/tag dispersed with the fragrance. Determining may involve measuring an electrostatic charge. Adjusting may be by selection/adjustment of one or more of a plurality of available scent modifiers onboard the scent diffusion devices. A user may adjust an overall level of fragrance desired in the space and a scent diffusion device controller may determine the adjustment required for the one or more devices. Adjusting may involve a master diffusion unit of the network of scent diffusion devices adjusting its own output level and the output level of its slaves upward or downward, proportionately based on the adjusted operation parameter. The sensed level may indicate the presence of a malodor and the operation parameter may be adjusted to provide a scent neutralization. The sensed level may indicate the presence of a malodor and the operation parameter is adjusted to terminate diffusion of the scent. The sensed level may indicate the presence of at least one of an allergen, a bacteria, a virus, a chemical and an airborne pathogen, and the operation parameter may be adjusted to counteract the presence.

In an aspect, a method may include disposing at least one sensor within an environment that transmits sensor data to a remote computer 1604, receiving at least one target value of a scent parameter for the environment at the remote computer 1602, based on the sensor data, controlling, via the remote computer, diffusion of a scent from at least one scent diffusion device to achieve the target value of the scent parameter 1608, wherein controlling includes setting or adjusting an operation parameter of the at least one scent diffusion device in response to the sensor data, and relaying the adjustment from the scent diffusion device to one or more other scent diffusion devices in a network. The sensor data may relate to at least one of room volume, room geometry, room area, airflow, presence of odor-producing materials, presence of odor-sinking factors, lighting, air flow, altitude, traffic flow, occupancy detection (IR, camera, CO2 sensor), proximity sensing, detected odor, fragrance level, temperature, humidity, time of day, season, weather event, and detection of a VIP/specific individual entering the space (via smartphone ping or the like). The scent diffusion device may include at least one package containing fragrance oil. The scent diffusion device may include at least two packages containing fragrance oil. One scent diffusion device may be a master node and the other scent diffusion devices are slave nodes and receive control instructions from the remote computer through the master node. The scent diffusion devices may relay control instructions in series, in a ring, in a mesh, or in a star networking topology. Each scent diffusion device can adjust its own control settings based on the activities of the other scent diffusion devices. The method may further include configuring the at least one scent diffusion device so that a device duty cycle does or does not occur simultaneously within proximity to another scent diffusion device. The scent parameter may relate to a brand management goal. The method may further include determining the total number of scent diffusion devices to dispose in the environment based on a room volume. The method may further include determining one or more locations to dispose the scent diffusion devices in the environment based on a room volume. The operation parameter may include at least one of a flow rate of the liquid, a duration of flow of the liquid, a variation in the flow rate of the liquid, an on/off status of the diffusion device, a package from which to diffuse the liquid, and a switch to a different package from which to diffuse the liquid.

In an aspect, a method may include disposing at least one sensor within an environment to determine a level of an airborne substance according to an automated sampling program, providing the level as feedback to a scent diffusion device 1502, adjusting an operation parameter of the scent diffusion device in response to the feedback, wherein adjusting enables the maintenance of a scent profile in the environment 1504, and communicating the adjustment to other scent diffusion devices in a network of scent diffusion devices 1508. Adjusting may be by selection/adjustment of one or more of a plurality of available scent modifiers onboard the scent diffusion devices. A user may adjust an overall level of a fragrance desired in the space and a scent diffusion device controller may determine the adjustment required for the one or more devices. Adjusting may involve a master diffusion unit of the network of scent diffusion devices adjusting its own output level and the output level of its slaves upward or downward, proportionately based on the adjusted operation parameter. The sensor may indicate the presence of a malodor and the operation parameter may be adjusted to provide scent neutralization. The sensor may indicate the presence of a malodor and the operation parameter is adjusted to terminate diffusion of the scent. The sensor may indicate the presence of at least one of an allergen, a bacteria, a virus, a chemical and an airborne pathogen, and the operation parameter is adjusted to counteract the presence.

In an aspect, a user interface for a scent design and modeling system produced by computing equipment executing program code stored in a non-transitory storage medium may include a drag-and-drop interface to place objects that represent a component of an environment being modeled in a relationship to one another to form an environment model, wherein at least one object is a source of a malodor, and a processor that models the scent-impacting parameters of the objects in the environment model and determines at least one of a placement in the environment for and a scent-diffusing parameter of one or more scent diffusion devices.

In an embodiment, a method for confirming a scent diffusion may include mixing a known amount of a tag with a known amount of scent for diffusion, diffusing the scent and tag mixture with one or more networked scent diffuser devices in to an environment, sampling the air in the environment and measuring the amount of the tag in the sample, and calculating the amount of scent in the sample based on the measured amount of tag. The tag may be odorless, a perfluorocarbon, or some other tag.

In an embodiment, the diffusion devices and the control settings may be configured based on an HVAC system tonnage, such as by using industry HVAC guidelines from ASHRAE. In an embodiment, the diffusion devices and the control settings may be configured based on an area of a space or a linear distance between a source of the scent and a targeted area or audience.

In an aspect, a method of managing scent in an environment may include disposing one or more scent diffusion devices within an environment, wherein the diffusion devices include a communications facility that enables transmitting signals to and receiving signals from a remote computer, taking information about an HVAC system in the environment to the remote computer, taking at least one scent parameter for scenting an environment at the remote computer, and controlling, via the remote computer, at least one of the scent diffusion devices to achieve the scent parameter, wherein controlling includes setting or adjusting an operation parameter of the scent diffusion device based on the information about the HVAC system. The information may be a tonnage of the HVAC system. The information may include at least one of indoor temperature, outside air temperature, thermostat schedule, energy consumption, historical operation parameters, vacant room detection capability, occupied room detection capability, vent placement, duct size, fan speed, and maintenance status.

In an aspect, a method of managing scent in an environment may include disposing a plurality of diffusion devices within an environment, wherein the diffusion devices comprise a communications facility that enables transmitting signals to and receiving signals from a local area network control device. The local area network control device is networked to each of the plurality of scent diffusion devices. The local area network control device receives communications from and distributes control instructions to the plurality of scent diffusion devices. An HVAC system controller may be networked to the local area network control device, wherein the HVAC system transmits data to the local area network control device regarding at least one parameter of the HVAC system. The local area network control device receives at least one scent parameter for scenting an environment and controls the diffusion of a scent from at least one of the plurality of scent diffusion devices to achieve the scent parameter. Controlling includes setting or adjusting an operation parameter of one or more of the scent diffusion devices in response to the data from the HVAC system.

Alternatively, a building system controller may be networked to the local area network control device, wherein the building system controller transmits data to the local area network control device regarding at least one parameter of the building system. Controlling the plurality of scent diffusion devices by the local area network control device to achieve the scent parameter includes setting or adjusting an operation parameter of one or more of the scent diffusion devices in response to the data from the building system. Data from the building system may include at least one of a number of people entering and exiting the building, planned use of a space, planned occupancy of a space, elevator use, escalator use, power use, lighting use, and plumbing use.

In an embodiment, the diffusion devices and the control settings may be configured based on a brand management goal as represented by a targeted scent concentration goal, (e.g. subtle scent, average scent, dense scent), an SCF, an index of consumer behavior, a CPM, a sales lift, or the like following protocols that leverage microcontroller devices and remote management via a NOC. To determine if the space complies with the brand management goal, a scent concentration factor may be measured or obtained such as by an electronic nose or a human nose.

In an embodiment, the initial settings for a diffusion device, adjusting the control settings throughout operation of the diffusion device, and location of the diffusion devices within the space are all distinct aspects of scent network configuration and control.

In embodiments, the SCF is a normalized index of scent. In other embodiments, the SCF may have units of scent concentration, such as ppm. The SCF, optionally along with other factors, such as one or more of room volume, room geometry, if the space is shared, airflow, presence of odor-producing materials, presence of odor-sinking factors, lighting, temperature, humidity, air flow, altitude, traffic flow, sounds, time of day, season, weather event, occupancy (e.g. by IR, camera), detection of a VIP/specific individual (e.g. Bluetooth/WiFi), proximity of objects to the diffusion devices, service cycle, position in a service cycle, and inventory of particular "base," "mid-" and "high" notes in a chord may be used in producing a consistent, precise fragrance profile or scent brand impression over time in an environment. The fragrance profile may be a fragrance chord that includes one or more of a base note, mid note, and high note. Producing the consistent fragrance profile may include adjusting a setting of the fragrance diffusion at one or more diffusion devices in an environment. The SCF may be measured periodically over time to ensure that it is within the parameters of a brand impression. Diffusion devices in the environment may be programmed to diffuse scents at different rates in order to provide the desired SCF in the environment.

In an embodiment, an SCF sensor may be used to monitor an SCF in an environment. The sensor may be standalone, such as in a wall-mounted device that also displays the setting, or integrated with a diffusion device. In embodiments, the wall-mounted device may also be a controller for the diffusion devices. The SCF sensor may sense an odorless marker diffused with the fragrance. The SCF sensor may be a particle sensor. The SCF sensor may be a machine olfaction sensor or a VOC (volatile organic compounds) sensor. The sensor may be an attachment to a tablet/smartphone. The SCF sensor may monitor particles by an electrostatic mechanism. The SCF sensor may operate by a radioactive mechanism to evaluate the presence of a solid object in the air.

In an embodiment, a method of calculating a scent concentration factor may include diffusing a scent into an environment at a known concentration, determining a measurable impact of the scent at the known concentration, repeating the steps of diffusing and determining for a plurality of scent concentrations in the environment, and correlating the known concentrations of scent with the measured impact of the scent at each concentration to determine a normalized index of scent. Determining may involve measuring a component of the scent, an odorless marker diffused with the scent, particles, a concentration of volatile organic compounds, and the like.

In an embodiment, an application controlling the device may be placed into a survey mode. For example, an individual or customer site may be defined as a local node in the survey. The survey may take users of the application through a process to calibrate the scent level, such as by following a programmed logic, a set of rules, a decision tree, or the like.

The scent management system for a remote-controlled, network of wide area scent diffusion devices may be directed to achieving a functional benefit. The functional benefit may be one or more of generating a memorable brand impression, stress reduction, appetite inducement, excitation, attraction inducing, calming, metabolism or insulin impacting, pharmacological, therapeutic, aromacological, psychological, increasing dwell time of a user in a space, and the like. The functional benefit may be provided by the managed diffusion of one or more of a stress-reducing fragrance, appetite inducing fragrance, exciting fragrance, attraction-inducing fragrances, a therapeutic fragrance, a metabolic-impacting scent, and an aromatherapy fragrance or blend of fragrances.

In an embodiment, a method of managing scent in an environment may include disposing at least one scent diffusion device within an environment, wherein the at least one scent diffusion device comprises a communications facility that enables transmitting signals to and receiving signals from a remote computer, disposing at least one sensor within the environment that transmits sensor data to the remote computer, processing the sensor data to determine a condition of one or more people in the environment, and based on the sensor data, controlling, via the remote computer, diffusion of a scent from a source of the scent in fluid communication with the at least one scent diffusion device to achieve a functional benefit with respect to the condition. Controlling may include setting or adjusting an operation parameter of the at least one scent diffusion device in response to the sensor data. The sensor may include at least one of a microphone, an imaging sensor, a biometric sensor, a hormone sensor, and an olfactory sensor. In an example, the sensor may be an imaging sensor, the sensor data relates to a facial recognition, the condition is a negative condition, and the scent is selected to achieve the functional benefit of reducing the negative condition. In an example, the sensor may be a microphone, the sensor data relates to a volume of a crowd, the condition is an unexcited tone, and the scent is selected to achieve the functional benefit of exciting the crowd. In one example, the condition may be a negative condition, such as aggression, anger, agitation, hysteria, antagonistic, belligerent, bullying, chaos, conflict, fright, rage, misery, and tantrum. The functional benefit may be at least one of reinforcing the negative condition and modifying the negative condition. Modifying may be at least one of reducing the negative condition and augmenting the negative condition. In another example, the condition may be at least one of a neutral condition and a positive condition. The functional benefit may be at least one of reinforcing the condition and modifying the condition. Modifying may be at least one of reducing the condition and augmenting the condition.

In an embodiment, a method of managing scent in an environment may include disposing at least one scent diffusion device within an environment, wherein the at least one scent diffusion device comprises a communications facility that enables transmitting signals to and receiving signals from a remote computer, disposing at least one sensor within the environment that transmits sensor data to the remote computer, processing the sensor data, and based on the sensor data, controlling, via the remote computer, diffusion of a scent from a source of the scent in fluid communication with the at least one scent diffusion device to achieve a functional benefit. In one example, the sensor is a clock, and the functional benefit is to simultaneously bring a group of people to at least one of high alert, calm, and sleep. In one example, the sensor determines an occupancy, and the functional benefit is the dispersion of people occupying a space.

In an embodiment, a method of managing scent in an environment may include disposing at least one scent diffusion device within an environment, wherein the at least one scent diffusion device comprises a communications facility that enables transmitting signals to and receiving signals from a remote computer, receiving data regarding the environment or an adjacent environment at the remote computer, based on the data, controlling, via the remote computer, diffusion of a scent from a source of the scent in fluid communication with the at least one scent diffusion device to achieve a functional benefit. In an example, the data relates to an allergen map of the environment, and the functional benefit is to counteract the effects of the allergens. The scent may include charged particles.

In an aspect, a method of managing scent in an environment may include disposing at least one scent diffusion device within an environment, wherein the at least one scent diffusion device comprises a communications facility that enables transmitting signals to and receiving signals from a remote computer, disposing at least one sensor within the environment that transmits sensor data to the remote computer, processing the sensor data to determine a condition of one or more people in the environment, triggering an alert based on the condition and transmitting the alert to a user, and enabling the user to control, via the remote computer, diffusion of a scent from a source of the scent in fluid communication with the at least one scent diffusion device to achieve a functional benefit with respect to the condition. Controlling includes setting or adjusting an operation parameter of the at least one scent diffusion device in response to the sensor data. The sensor may include at least one of a microphone, an imaging sensor, a biometric sensor, a hormone sensor, and an olfactory sensor. In some embodiments, the condition is a negative condition, such as aggression, anger, agitation, hysteria, antagonistic, belligerent, bullying, chaos, conflict, fright, rage, misery, and tantrum. The functional benefit may be at least one of reinforcing the negative condition and modifying the negative condition. Modifying may be at least one of reducing the negative condition and augmenting the negative condition. In some embodiments, the condition may be at least one of a neutral condition and a positive condition. The functional benefit may be at least one of reinforcing the condition and modifying the condition, wherein modifying may be at least one of reducing the condition and augmenting the condition. In an example, the sensor may be an imaging sensor, the sensor data relates to facial recognition, the condition is a negative condition, and the scent may be selected to achieve the functional benefit of reducing the negative condition. In another example, the sensor is a microphone, the sensor data relates to a volume of a crowd, the condition is an unexcited tone, and the scent is selected to achieve the functional benefit of exciting the crowd.

In an aspect, a method of managing scent in an environment may include disposing at least one scent diffusion device within an environment, wherein the at least one scent diffusion device comprises a communications facility that enables transmitting signals to and receiving signals from a remote computer, disposing at least one sensor within the environment that transmits sensor data to the remote computer, processing the sensor data, triggering an alert based on the sensor data and transmitting the alert to a user, and enabling the user to control, via the remote computer, diffusion of a scent from a source of the scent in fluid communication with the at least one scent diffusion device to achieve a functional benefit with respect to the condition. The sensor may be a clock, and the functional benefit is to simultaneously bring a group of people to at least one of high alert, calm, and sleep. The sensor may determine occupancy, and the functional benefit is the dispersion of people occupying a space.

In an aspect, a method of managing scent in an environment may include disposing at least one scent diffusion device within an environment, wherein the at least one scent diffusion device comprises a communications facility that enables transmitting signals to and receiving signals from a remote computer, receiving data regarding the environment or an adjacent environment at the remote computer, triggering an alert based on the data and transmitting the alert to a user, and enabling the user to control, via the remote computer, diffusion of a scent from a source of the scent in fluid communication with the at least one scent diffusion device to achieve a functional benefit with respect to the condition. The data relates to an allergen map of the environment, and the functional benefit is to counteract the effects of the allergens. The scent may include charged particles.

In an aspect, a method of scent casting in an environment, may include disposing a scent diffusion device within an environment, wherein the scent diffusion device comprises a communications facility that enables transmitting signals to and receiving signals from a remote computer, determining a distance from the scent diffusion device to a scent target location, gathering data related to the environment or people in the environment and transmitting the data to the remote computer, receiving, at the remote computer, at least one functional benefit desired for the scent target location and the data, and controlling, via the remote computer, the scent diffusion device to achieve the functional benefit, wherein controlling includes setting an operation parameter of the scent diffusion device based on the determined distance, the data, and the functional benefit. The data may relate to at least one of sound, an image, a biometric feature, a hormone, an aroma, room volume, room geometry, room area, airflow, presence of odor-producing materials, presence of odor-sinking factors, lighting, air flow, altitude, traffic flow, occupancy detection (IR, camera, $CO_2$ sensor), proximity sensing, detected odor, fragrance level, temperature, humidity, time of day, season, weather event, and detection of a VIP/specific individual entering the space (via smartphone ping or the like). The data may be processed to reveal the mood of a group of people. The mood may be at least one of aggression, anger, agitation, hysteria, antagonistic, belligerent, bullying, chaos, conflict, fright, rage, misery, and tantrum. The functional benefit may be at least one of reinforcing the mood and modifying the mood. Modifying may be at least one of reducing the mood and augmenting the mood.

In an example, the data may be a facial recognition, the mood is a negative mood, and the scent may be selected to achieve the functional benefit of reducing the negative mood. The data may relate to a volume of a crowd, the mood is unexcited, and the scent is selected to achieve the functional benefit of exciting the crowd. The scent target location may be a person. The functional benefit may be to attract people or disperse people. The method may further include emitting at least one of a light and a sound towards the scent target location or dispersing an active agent, wherein the agent is active by at least one of contact, taste, and inhalation.

The scent management system may monitor an environment for an indicator that a service is being delivered, and when an indicator is received, the system may cause a change at one or more scent diffusion devices, such as a scent to be diffused or a scent diffusion to be terminated, wherein the change is intended to be a companion or complement to the service. The service may include at least one of lighting, music being played, a fountain, a displayed item, the arrival of one or more people, a food service or any other service being deployed in the environment. The indicator may be through a manual input or a detection by an environmental sensor. For example, if food is being served in a small area, a complementary service may be to deliver a scent in a broader area.

In an aspect, a method for managing scent in an environment may include disposing a plurality of scent diffusion devices within the environment, wherein the scent diffusion devices comprise a communications facility that enables transmitting signals to and receiving signals from a remote computer, monitoring the environment for an indicator that a service is being delivered, and when the indicator is received, controlling, via the remote computer, at least one of the plurality of scent diffusion devices to emit a scent that is intended to be a companion to the service.

In an aspect, a method of managing scent in an environment may include disposing at least one scent diffusion device within an environment, wherein the at least one scent diffusion device comprises a communications facility that enables transmitting signals to and receiving signals from a remote computer, disposing at least one sensor within the environment that transmits sensor data to the remote computer, monitoring an environment via the at least one sensor for an indicator that a service is being delivered, and when the indicator is received, as determined by the sensor data, controlling, via the remote computer, diffusion of a liquid from a source of the liquid in fluid communication with the at least one scent diffusion device to emit a scent that is intended to be a companion to the service, wherein controlling includes setting or adjusting an operation parameter of the at least one scent diffusion device. A method of managing a scent to complement a service may include providing a scheduling facility to indicate when a service is scheduled to occur in an environment, selecting a scent to be diffused in the environment that complements the scheduled service, and triggering a diffusion of the scent in accordance with the scheduled service. In certain embodiments, the complement to the scheduled service is to have an unscented environment. In these embodiments, diffusion would be triggered to cease, or in other embodiments, diffusion of a scent would cease followed by diffusion of an odor neutralizing agent. In embodiments, it is not diffusion of a liquid but diffusion of a gas.

A scent to complement a service may be scheduled. A method of managing a scent to complement a service, may include providing a scheduling facility to indicate when a service is scheduled to occur in an environment and allowing a user to select a scent to be diffused in the environment that complements the scheduled service, and when the event occurs, launching a survey to be given to participants of the scheduled service, wherein the survey is used to calculate a metric for a brand impression.

Individual diffuser devices may communicate with one another in order to deliver a service-complementing scent. A method may include monitoring an environment for an indicator that a service is being delivered, when the indicator is received, and using device-to-device communication protocols, causing a network of scent diffusion devices to coordinate delivery of a scent to the environment that is intended to be a companion to the service, monitoring a traffic sensor in the environment to determine a number of scent impressions delivered by the network of scent diffusion devices, and transmitting the number to a computer.

In an aspect, a method may include monitoring an environment for an indicator that a service is being delivered, when the indicator is received, causing a network of scent diffusion devices to coordinate delivery of a scent to the environment that is intended to be a companion to the service, monitoring a traffic sensor in the environment to determine a number of scent impressions delivered by the network of scent diffusion devices, and transmitting the number to a computer, wherein the number enables a third party to perform a brand management task.

In an embodiment, a networked scent diffusion device may be integrated with an object to provide a brand impression and/or coordinate with a function of the object. For example, the object may be a digital painting that rotates between various scenes, such as lilacs, then a tropical waterfall, then gardenias, and so on. An associated or integrated diffusion device may diffuse the scent of lilacs to coordinate with the digital painting when lilacs are being displayed then switch to a tropical aroma when the waterfall is shown, and so on. In embodiments, the object may be lighting, a light wall, a waterfall wall, a fountain, a speaker, a display screen, an object delivering visual effects, an indoor garden, and the like.

In an embodiment, a method of a multi-sensory experience may include disposing an object with an integrated networked scent diffusion device in an environment, monitoring a function of the object, and diffusing scent from the device in coordination with the function of the object. The object may be at least one of a digital painting, lighting, a light wall, a waterfall wall, a fountain, a speaker, a display screen, an object delivering visual effects, and an indoor garden. Alternatively, the method may include disposing an object with an integrated networked scent diffusion device in an environment, wherein scent diffusion from the device is coordinated with a function of the object, and communicating with a mobile device in the environment to engage the mobile device user with respect to one or more of the object and the scent diffusion.

In an embodiment, one or more networked scent diffuser devices may be controlled via a combination of different web applications (e.g., Facebook, Evernote, Weather, iOS Location, Dropbox, Foursquare, etc.) through a conditional command to perform a scent function upon reaching a condition or trigger indicated by the conditional command. For example, the conditional statement may be that if an iOS Location indicates that a particular user is within a predetermined distance from the network of diffusion devices, the devices should be triggered to turn on. In another example, if a Weather application indicates it will be snowing in the afternoon, a wintertime fragrance may be diffused. In an embodiment, a method of conditionally commanding a networked scent diffuser may include setting a condition for the diffuser using a remote computer, determining when the condition has been met, and controlling the diffuser to perform an operation when the condition has been met. In an embodiment, a method of conditionally commanding a networked scent diffuser with at least two packages may include setting a condition for the diffuser using a remote computer, determining when the condition has been met, and controlling the diffuser to switch between the at least two packages when the condition has been met.

In an embodiment, a networked scent diffuser device may be controlled by an application to emit a scent in coordination with an electronic story. The application controlling the electronic story may also control the diffusion device. For example, the electronic story may be about a baker making different pies and when a scene for baking a blueberry pie is displayed by the application, the application may control the diffusion device to diffuse a blueberry scent. In an embodiment, the scent diffuser device may be integrated with a networked LED light. Continuing with the example, when a scene for baking a blueberry pie is displayed by the application, the application may control the diffusion device to diffuse a blueberry scent and may cause blue light to be emitted by the LED light. In an embodiment, a method of coordinating scent with an electronic story may include disposing an object with an integrated networked scent diffusion device in an environment and connecting it to a network, connecting a device that hosts an electronic story to the network, and programming the scent diffusion device to diffuse a scent in coordination with the electronic story.

In an embodiment, a chair with an integrated scent diffusion device may provide coordinated playlists of one or more of scent, music, and lighting. The chair may be a desk chair, seating in an automobile, airline seating, restaurant seating, lobby seating, public benches, and the like. In an embodiment, the chair may include a seat, an integrated scent diffusion device, and a processor to control the device to provide a scent diffusion. The chair may further include at least one of a speaker and lighting, and wherein the processor controls the device and the at least one speaker or lighting in a coordinated playlist of at least one of scent, music, and lighting. The seat may be at least one of a desk chair, seating in an automobile, airline seating, restaurant seating, lobby seating, and a public bench.

In an embodiment a candle and a scent diffusion device may be managed as part of the same scent management system, wherein the candle may be extinguished and ignited in response to network signals and/or a measured SCF. A method of managing scent in an environment may include disposing at least one candle within an environment, receiving at least one target value of a scent parameter for the environment at a remote computer, and based on the target value, controlling, via the remote computer, a device to either extinguish or ignite the candle to achieve the target value of the scent parameter. Controlling may involve receiving data from a sensor disposed in the environment to determine a level of the scent in the environment.

In embodiments, the diffusion device may be a consumer level scent diffuser and may not be networked to other scent diffusion devices or may be networked on a home-level local network.

In an embodiment, an evaluation kit may be used to determine what type of fragrance is to be used in the diffusion devices.

In an embodiment, a DMX protocol board may be useful for controlling one or more of a light, audio and scent diffusion.

In an embodiment, a scent environment computer-based design environment may operate on a data structure that describes an environment to be fragranced, wherein the data structure is used to calculate scent volume levels generated by one or more diffusers in an environment and optimize the installation of one or more diffusion devices, such as based on various environmental factors, such as the size of the environment, the shape of the environment, objects and materials in the environment, air flow within the environment, equipment in the environment (including fans, hoods, vents, ducts, conduits, HVAC elements, and the like). The design environment and environment data structure may be used to determine one or more of installation of new devices and re-programming of device operation when the aggregate scent volume desired is changed. The data structure may be used with an extrapolation algorithm to establish and manage an aggregate scent level. The design environment may indicate fragrance zones and fragrance-free zones. The data structure may include sensed environmental parameters.

Figure 5:
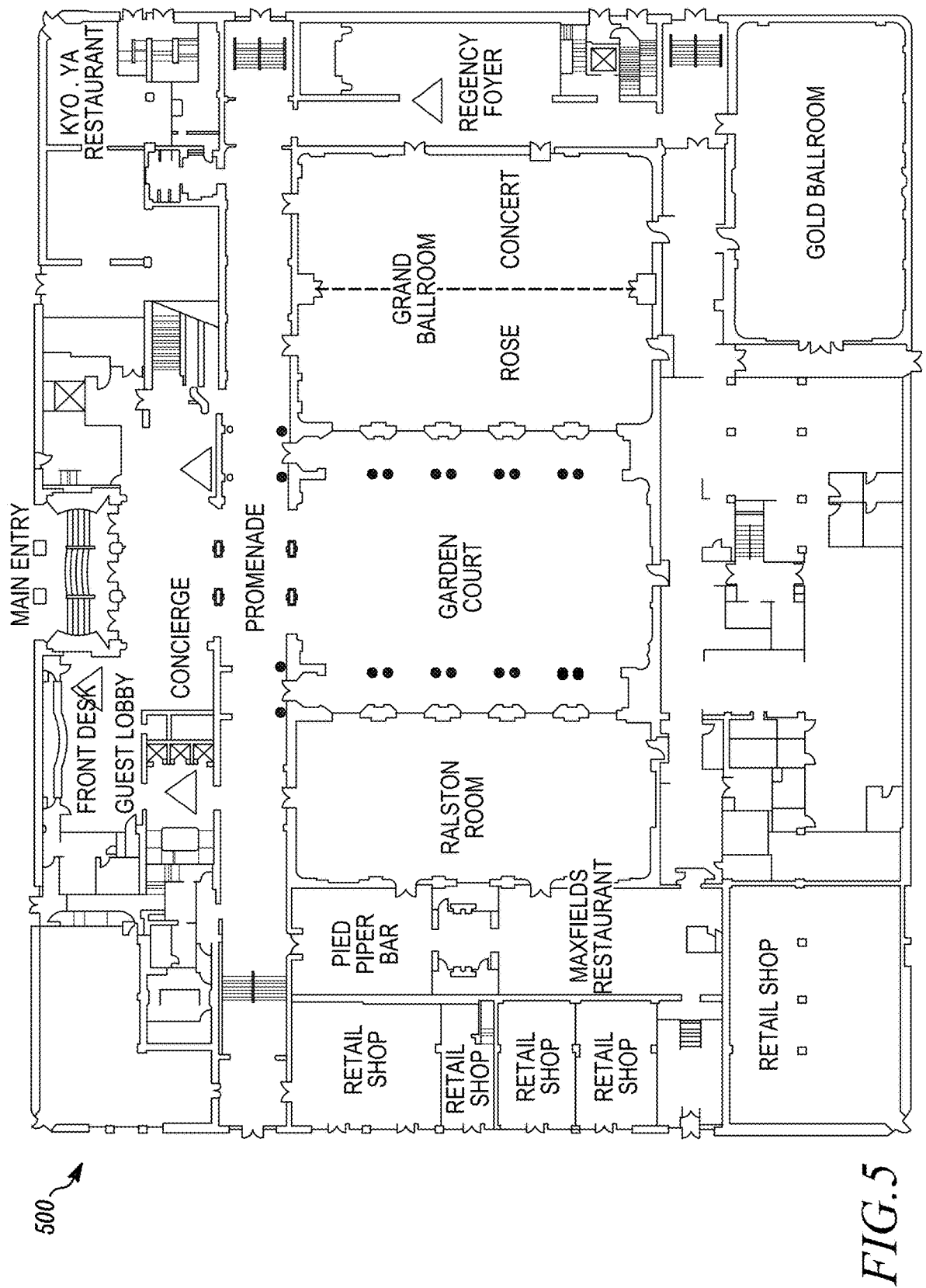
FIG. 5 depicts a representative installation of diffusion devices.

In an embodiment, a scent environment design interface may be a user interface depicting the data structure for describing an environment, wherein the user interface is useful for designing a deployment and programming of one or more networked scent diffuser devices. The user interface may colorimetrically depict scent plumes/zones and airflow/diffusion areas. The user interface may show consumer pathways (optionally with timing) to ensure multiple exposures with a fragrance-free zone in between each exposure. The user interface may allow designers to drag and drop scent zones based on an HVAC/building blueprint to optimize scent vectors/scent device settings. The data structure may include information about an environment, including a scent neutralizing profile of the environment, and the user interface may allow users to access a profile of fragrances that would nevertheless be effective in fragrancing the environment (e.g. based on particle size, concentration of certain fragrance notes, etc.) given the scent neutralizing profile. FIG. 5 depicts an exemplary output 500 from the design interface showing the installation of diffusion devices shown as triangles.

In an aspect, a method of implementing a computer-implemented automated scent environment design and modeling system may include defining objects that represent a component of an environment being modeled, wherein at least one parameter of at least one of the objects impacts the diffusion of scent within the environment, assembling an environment model utilizing the objects, inputting data to the environment model related to one or more sensors in the environment, using at least one data structure representing at least one parameter of a scent diffusion device, and displaying information about diffusion of scent in the environment based on the environment model, the defined objects, and at least one parameter of the at least one scent diffusion device. Determining a placement of one or more scent diffusion devices in the environment may be based on the one or more scent impression goals, the environment model and the data. The objects may be represented in a three-dimensional relationship. The method may further include allowing a user to define one or more scent impression goals for the environment. The method may further include recommending a placement of one or more scent diffusion devices in the environment based on the one or more scent impression goals and the environment model. The method may further include inputting data to the environment model related to one or more sensors in the environment. The information may be displayed in a graphical user interface that shows the physical dimensions of the environment and the objects in the environment. The display may be a 3D display. The display may be a 3D overhead view of the environment. The object may be at least one of a window, a skylight, a wall, a floor, a door, a ceiling, a fireplace, furniture, plants, an HVAC system and its elements, fans, hoods, vents, ducts, conduits, a fragrance-free zone, a fragrance zone, a consumer pathway, and the like. The data may relate to at least one of room volume, room geometry, airflow, HVAC systems, presence of odor-producing materials, presence of odor-sinking factors, lighting, temperature, humidity, altitude, traffic flow, occupancy, time of day, and the like. The objects may be customized based upon the inputted scent impression goal. For example, furniture or plants may be removed if they are found to interfere with a scent plume. Assembling the environment model may include using a drag-and-drop interface to place the objects in the three-dimensional relationship. The scent impression goal may include planning for fragrance zones and fragrance-free zones. The environment model may colorimetrically depict scent plumes/zones and airflow/diffusion areas. The environment model may depict consumer pathways (optionally with timing) to ensure multiple exposures with a fragrance-free zone in between. The method may further include suggesting a profile of fragrances that would be effective in the environment given data relating to a scent neutralizing profile of the environment. An effective fragrance may be identified based on one or more of a particle size and a scent concentration factor. The environment model may be used to calculate scent volume levels generated by one or more diffusers in the environment. The environment model may be used in re-programming device operation when the aggregate scent volume desired is changed.

In an aspect, a method of implementing a computer-implemented automated scent environment design and modeling system may include defining objects that represent a component of an environment being modeled, wherein at least one parameter of at least one of the objects impacts the diffusion of scent within the environment, assembling an environment model utilizing the objects, inputting data to the environment model related to one or more sensors in the environment, using at least one data structure representing at least one parameter of a network of scent diffusion devices, and displaying information about diffusion of scent in the environment based on the environment model, the defined objects, and at least one parameter of the network of scent diffusion devices.

In an aspect, a user interface produced by computing equipment executing program code stored in a non-transitory storage medium may be an interface for a scent design and modeling system. The user interface may include a drag-and-drop interface to place objects that represent a component of an environment being modeled in a relationship to one another to form an environment model, wherein at least one parameter of at least one of the objects impacts the diffusion of scent within the environment, and a processor that models the scent-impacting parameters of the objects in the environment model and determines at least one of a placement in the environment for and a scent-diffusing parameter of one or more scent diffusion devices. The environment model further includes one or more scent impression goals. The processor further models the scent impression goals for the environment model to determine at least one of a placement in the environment for and a scent-diffusing parameter of one or more scent diffusion devices. The environment model further includes data related to one or more sensors in the environment. The environment model may be displayed in a graphical user interface that shows the physical dimensions of the environment and the objects in the environment. The display may be a 3D display. The display may be a 3D overhead view of the environment. The drag and drop interface enables dragging and dropping scent zones based on an HVAC/building blueprint to optimize scent vectors/scent device settings. The object may be at least one of a window, a skylight, a wall, a floor, a door, a ceiling, a fireplace, furniture, plants, an HVAC system and its elements, fans, hoods, vents, ducts, conduits, a fragrance-free zone, a fragrance zone, a consumer pathway, and the like. The data may relate to at least one of room volume, room geometry, airflow, HVAC systems, presence of odor-producing materials, presence of odor-sinking factors, lighting, temperature, humidity, altitude, traffic flow, occupancy, time of day, and the like. The objects can be customized based upon the inputted scent impression goal. The relationship may be a three-dimensional relationship. The object may be a source of a malodor For example, in order to achieve a particular fragrance level in a space, it may be determined that a particular number of devices must be used and they should be positioned at particular points in the room such that when they are diffusing, there aggregate diffusion achieves the fragrance level. In embodiments, the settings for each of the devices may need to be set differently in order to achieve the fragrance level. For example, if a fragrance level of 7 is desired at a particular scent target location in the room, the two closest scent devices to the target may be set to 7 but the device further away may be set to 10.

A user interface for a scent design and modeling system produced by computing equipment executing program code stored in a non-transitory storage medium may include a drag-and-drop interface to place objects that represent a component of an environment being modeled in a relationship to one another to form an environment model, wherein at least one parameter of at least one of the objects impacts the diffusion of scent within the environment, and a processor that models the scent-impacting parameters of the objects in the environment model and determines at least one of a placement in the environment for and a scent-diffusing parameter of a network of scent diffusion devices.

In an embodiment, a method of implementing an automated scent environment design and modeling system may include accessing an environment model for an environment to be scented, wherein the model includes one or more networked scent diffusion devices, indicating a service presented in the environment, and programming a scent diffusion profile for the one or more networked scent diffusion devices to complement the service.

In an embodiment, a method for operating networked scent diffusion devices in an environment to achieve a functional benefit may include accessing an environment model for the environment, wherein the model includes one or more networked scent diffusion devices and programming a scent diffusion profile for the environment to be executed by one or more of the networked scent diffusion devices to achieve the functional benefit.

In an embodiment, a scent media-based advertising platform may be used by advertisers to bid upon scent space. The scent space may be one or more of an elevator, an atrium, a food court, a walkway, a display area, a kiosk, an information kiosk, a planter, a restroom, and the like. The advertising platform may further be a mixed-media advertising platform, enabling advertisers to purchase scent space as well as print/image space, manage an ad campaign including blocking other scent-based advertisers, and the like. The scent-based advertising space may include one or more networked scent diffuser devices.

In an embodiment, a method of operating a scent media-based advertising platform may include disposing at least one scent diffusion device in a scent-based advertising space, wherein the at least one scent diffusion device comprises a communications facility that enables transmitting signals to and receiving signals from a remote computer, providing an scent-media based advertising instruction to the remote computer, and controlling, via the remote computer, diffusion of a scent from a source of the scent in fluid communication with the at least one scent diffusion device in accordance with the advertising instruction. Scent-based advertising space may be bid upon by one or more advertisers. The scent space may be at least one of an elevator, an atrium, a food court, a walkway, a display area, a kiosk, an information kiosk, a planter, and a restroom. The method may further include enabling advertisers to purchase scent space as well as print/image space. The method may further include enabling advertisers to manage a scent media-based ad campaign including blocking other scent-based advertisers.

In an embodiment, a method of scent casting in an environment may include disposing a scent diffusion device within an environment at a first location, wherein the scent diffusion device comprises a communications facility that enables transmitting signals to and receiving signals from a remote computer, defining a plurality of scent target locations between the first location and a second location, disposing additional scent diffusion devices within the environment to provide scent at the scent target locations, receiving, at the remote computer, at least one scent parameter for at least one of the first location and the scent target locations, and controlling, via the remote computer, the scent diffusion device to achieve the scent parameter at at least one of the first location and the scent target locations, wherein controlling includes setting an operation parameter of the scent diffusion device based on at least the scent parameter. The method may further include determining a distance from the scent diffusion devices to the scent target locations, wherein controlling further includes setting an operation parameter of the scent diffusion devices based on the determined distance. The method may further include determining sales lift by comparing the purchase behavior of a group of participants exposed to the scent in the environment with a group of participants in a comparable environment who were not exposed to the scent. The first location may be a display at an entrance to the environment, the second location may be a retail location, and the scent target locations may be points along a path from the environment entrance to the retail location.

In an embodiment, a cost per thousand impressions (CPM) application may be used to determine CPM for a brand impression, wherein the brand impression is exposure to a scent delivered by one or more managed, networked scent diffuser devices. The CPM application may receive sensor information about the actual delivery of the scent in the space. The CPM application may measure how many people were exposed to the scent, such as by an occupancy sensor, a carbon dioxide sensor, and the like. The CPM application may determine, such as through a matched panel, a controlled experiment, or A/B testing, what people did when they were exposed to the scent. The CPM application may enable measuring direct feedback from users, such as through a survey delivered from a networked scent diffuser. The CPM application may determine sales lift by comparing the purchase behavior, including transactions, dwell time, and the like, of a group of participants exposed to a scent in a retail environment with a group of participants in a comparable retail environment who were not exposed to the scent. The scent exposure may be from one or more networked scent diffuser devices. Purchase behavior may be obtained by directly integrating the scent management system with a point-of-sale or other in-store equipment. Purchase behavior information may be used to manage the SCF level used by a brand. For example, a brand may use one SCF in one location and another SCF in another location or at a different time at the same location. Purchase behavior at the different SCF's can be compared to determine which SCF most effectively meets purchase behavior brand management goals.

In an embodiment, a method may include controlling a network of scent diffusers to deliver a scent to at least one target location, disposing a sensor at the at least one target location to capture consumer traffic and movement data, calculating a metric for a brand impression based on correlating the data from the at least one target locations to the scent delivery to determine an exposure to the scent, and aggregating the calculated metrics for the target locations to demonstrate a behavioral impact of the scent. The behavioral impact may be a consumer movement to a location due to the scent or a dwell time in a location.

In an embodiment, a point-of-sale device may include a motion sensor that detects a presence in an environment and generates a signal, a communications facility that enables transmitting the signal to and receiving instructions from a remote computer, and a scent diffusion device that receives instructions from the remote computer to diffuse a scent when the signal is received. The device may include an environmental sensor that detects an environmental condition and generates an environmental signal to transmit to the remote computer. The remote computer may use the signal and the environmental signal to generate the instructions. In an embodiment, a method of managing scent in an environment may include disposing at least one scent diffusion device within an environment, wherein the at least one scent diffusion device comprises a communications facility that enables transmitting signals to and receiving signals from a remote computer, disposing at least one sensor within the environment that transmits sensor data to the remote computer, monitoring an environment via the at least one sensor for an indicator, and when the indicator is received, as determined by the sensor data, controlling, via the remote computer, diffusion of a liquid from a source of the liquid in fluid communication with the at least one scent diffusion device to emit a scent. In embodiments, it is not diffusion of a liquid but diffusion of a gas. Controlling may include setting or adjusting an operation parameter of the at least one scent diffusion device. The sensor may be a motion sensor and the indicator is a motion. The sensors may be a motion sensor and an environmental sensor that detects an environmental condition, and the indicators are a motion and an environmental signal.

In an aspect, a method may include calculating a metric for a brand impression, wherein the brand impression metric is based on exposure to a scent delivered by one or more managed, networked scent diffusion devices. The metric may be based on at least one of number of exposures, duration of exposures, and location of exposures. Determining may include performing matched panel testing, A/B testing, or controlled testing of a population exposed to the scent. Determining may include obtaining feedback from a population exposed to the scent. The feedback may be through a survey delivered from the networked scent diffusion device.

In an aspect, a method may include determining sales lift by comparing the purchase behavior of a group of participants exposed to a scent in a retail environment with a group of participants in a comparable retail environment who were not exposed to the scent, wherein the scent exposure is due to one or more networked scent diffuser devices in the retail environment under the control of a remote computer.

In an embodiment, a method may include controlling a network of scent diffusers, using a remote computer, to deliver a scent to at least one target location, gathering sales data from at least one point-of-sale at the at least one target location and transmitting the sales data to the remote computer, and calculating a sales lift based on correlating the sales data from the at least one target locations to the scent delivery as compared to sales data from locations with no scent delivery.

In an embodiment, a networked scent diffuser device may serve as a commercial gateway for a consumer environment utilizing one or more integrated sensors to gather information from the consumer environment. The networked scent diffusion device may include a communications facility that receives control signals from a network operations center, the control signals for controlling a scent diffusion from the scent diffusion device in accordance with a scent impression goal and one or more integrated sensors to gather information from a consumer environment in which the scent diffusion device is deployed. The sensor may be a traffic/occupancy sensor.

In an embodiment, a networked scent diffuser device may serve as a commercial gateway for a consumer environment utilizing a network to communicate data to a mobile device in the consumer environment for consumer engagement. The networked scent diffusion device may include a first communications facility that receives control signals from a network operations center, the control signals for controlling a scent diffusion from the scent diffusion device in accordance with a scent impression goal, and a second communications facility to communicate data with a mobile device in the consumer environment. The communication may relate to a scent being diffused by the device. The commercial gateway allows a consumer in the consumer environment to control the scent diffuser device (e.g. via an app). The device may be controlled by a user in the consumer environment through one of the first or second communications facility. The communication may be an offer.

In embodiments, the scent management system may be usefully deployed in hotels/hospitality (e.g. lobby, rooms, hallway, elevator/elevator shaft, spa), casinos/gaming (e.g. gaming floor, restaurants, OTB area, shopping area, restrooms, arcade), night club/bar, cruise lines, spa/fitness (e.g. sauna, swimming pool/associated areas), building/corporate centers/commercial real estate, theaters/cinema, amusement, convention/expo, mall/retail (e.g. POS, walkways, restrooms, billboard/ad kiosk), warehouse stores, car showrooms/other showrooms, health care/senior living/dental (waiting room, testing facilities (stress reduction)), airport/transit (e.g. aircraft, restrooms, ad kiosk), stadium/sports venues, schools, waste management facilities/trash collection areas, funereal, pet care/veterinary (e.g. pet store, animal shelters, livestock/slaughterhouse/husbandry), race track, factory, military, grocery, bank, online social gaming, and the like.

The scent management system, including the diffusion devices, may be integrated with other environment sensing/changing network appliances; a kiosk, planter, or other fixed object in environment, a sound system, lighting, an HVAC system, a monitor (carbon monoxide, fire, etc.), and the like.

In embodiments, methods and systems disclosed herein include a networked liquid level monitor adapted to work with multiple liquid-containing cartridges. For example, one networked liquid level monitor may be used for a plurality of replaceable liquid cartridges. In embodiments, cartridges containing the same type of liquid may be switchable among each other. In embodiments, cartridges may be associated with heterogeneous liquid handling devices.

In embodiments, methods and systems disclosed herein may include a multiple (e.g., dual) kan-ban system with local automated switching (referred to in some cases herein as an auto-switching kan-ban). Such embodiments may include local processing with auto-switching in a dual kan-ban liquid dispensing system.

In embodiments, methods and systems disclosed herein include use of a signal from a multiple kan-ban, such as a switchover signal, as a signal (such as delivered over a network), to replace at least one container of the kan-ban.

Such embodiments may be used for replacement/refill management for liquid dispensing cartridges or other containers based on processing switchover data signals in dual cartridge liquid dispensing network.

In embodiments, methods and systems disclosed herein include the capability to replace a container in a dual or multiple container liquid dispensing system. Such embodiments may include a replaceable container for liquid dispensing in a multiple bin (e.g., two-bin) kan-ban system.

In embodiments, methods and systems disclosed herein include a smart filter. Such methods and systems may include determining the status of a filter of a liquid handling device and reporting on the status of the filter to maintenance or other management facility that handles filter replacement, which may be located at a remote location that communicates with the smart filter via networked communications. In embodiments, such methods and systems may include measuring the pressure differential on a filter to determine if it is a clogged filter.

In embodiments, methods and systems disclosed herein include a hybrid chamber for different types of cartridges. For example, a dual chamber for cartridges may include capacity for high turn cartridges that normally need frequent replacement and for low turn cartridges that don't' require frequent replacement.

In embodiments, methods and systems disclosed herein include a network of liquid dispensers. Such embodiments may include managed, networked liquid dispenser devices (adapted for various types of dispensing technology, including liquid dispensers, such as for beverages) for managing liquid supply, availability, delivery and the like. In embodiments, one such liquid dispenser device may be a master node, and other devices may be slave nodes, which may communicate to master node via a networking protocol, such as MiWi, Bluetooth Low Energy, or the like. Such a device may include a LAN card and/or a WAN card for operating in a master/slave mode and communicating locally and over longer distances. For example, a device may be a Zigbee-type device, and in embodiments it may be a slave to a gateway or may be a gateway itself. Embodiments may include wired or wireless devices, ones that can communicate with one another, and the like. Management of the devices may be remote or local. Communication may occur via a cloud platform. Devices may be standalone or integrated with or into another system. Devices may include a tampering proof enclosure, which may respond to a physical key and/or a software-based key.

In embodiments, methods and systems disclosed herein include a wireless, networked liquid dispenser device, wherein the device communicates with one or more other such devices via a networking protocol for generating a consistent liquid profile over a wide area, such as by ensuring consistency of ingredients, temperature, pressure, or the like in the area. In embodiments a networking protocol may be Zigbee, MiFi, DMX, ANT, or the like.

In embodiments, methods and systems disclosed herein include a networked liquid dispenser device with a signal that alerts a user of a device state. In embodiments the state relates to a sensed liquid level.

In embodiments, methods and systems disclosed herein include optimizing the installation of a plurality of liquid dispenser devices by creating a data structure describing an environment, wherein the data structure is used to calculate liquid volume requirements of one or more dispensers in an environment. In embodiments the data structure is used to determine one or more of installation of new devices and re-programming of device operation when the aggregate liquid volume desired is changed.

In embodiments, methods and systems disclosed herein include a user interface depicting a data structure for describing an environment useful for designing a deployment and programming of one or more networked liquid dispenser devices, wherein the data structure includes planning for zones in which liquid dispensers are located. In embodiments the user interface colorimetrically depicts liquid levels. In embodiments the interface may include drag and drop liquid zones based on building blueprint to optimize device locations and settings.

In embodiments, methods and systems disclosed herein include a liquid level sensor for a networked liquid dispenser device that provides real-time liquid levels and alerts for replacement, including in cases of unexpected readings. In embodiments a liquid level sensor comprises a floating magnet disposed within a track inside the liquid container, wherein as the liquid level changes, the floating magnet moves inside the track; and at least one Hall effect sensor disposed outside the fragrance container, wherein when the Hall effect sensor sense the magnet, a switch is caused to move from a first state to a second state (e.g. a solenoid switch between liquid containers). In embodiments, a sensor senses the presence of a vacuum or a threshold pressure/partial pressure. In embodiments, a camera is used to image a liquid level. In embodiments, a system may trigger an alert based on the fact that the device is not outputting what it should (e.g., a liquid level, but also optionally performance of a pump, valve, hose, filter, dispenser, or other liquid-handling element).

In embodiments, methods and systems disclosed herein include an automated switching system for a networked liquid dispenser device housing a plurality of liquid reservoirs to switch between reservoirs upon meeting a condition (e.g. a low level of liquid, a programmed switchover, and/or an indicator from a FIFO process for utilizing the packages in a replenishment process). In embodiments the switch is a valve. In embodiments the reservoirs hold different liquids that are used for blending.

In embodiments, methods and systems disclosed herein include a networked liquid dispenser device with multiple liquid reservoirs for operation in multiple configurations. In embodiments, two reservoirs house one liquid and two reservoirs house a second liquid so that each liquid can automatically switch to a new reservoir when one becomes empty. In a reservoir accepts a single use canister selected and installed by the user (e.g. a cup or similar container holding a flavor or other ingredient). In embodiments the reservoir is a cartridge. In embodiments the reservoir is a bag, balloon, or membrane-based container.

In embodiments, methods and systems disclosed herein include ones in which the liquid comes from a crystal or other non-liquid element.

In embodiments, methods and systems disclosed herein include a liquid cartridge for a networked liquid dispensing device with physical features for anti-tampering that prevent the cartridge from operating properly in a device not configured to accept the cartridge. In embodiments the cartridge includes an RFID for identification. In embodiments the RFID tag must be read correctly or the dispenser won't dispense. In embodiments the anti-tampering features further enable an alert to be sent over a network if the cartridge is removed (e.g. removed early, or removed in conflict with general instructions).

In embodiments, methods and systems disclosed herein include a networked liquid dispenser device, wherein the liquid device serves as a commercial gateway for a consumer environment utilizing one or more integrated sensors to gather information from the consumer environment.

In embodiments, methods and systems disclosed herein include a networked liquid dispenser device, wherein the liquid device serves as a commercial gateway for a consumer environment utilizing a network to communicate data to a cellphone in the consumer environment for consumer engagement. In embodiments the communication relates to a liquid being dispensed by the device. In embodiments, the commercial gateway allows a consumer in the consumer environment to control the liquid dispenser device (e.g. via an app). In embodiments, the communication is an offer.

In embodiments, methods and systems disclosed herein include monitoring an environment for an indicator that a service is being delivered, wherein when an indication is received, delivering a liquid that is intended to be a companion to the service. In embodiments the service is at least one of a lighting, music, fountain, displayed item, arrival of one or more people. In embodiments a fountain pours soda and/or beverage that is a "signature" of the service.

In embodiments, methods and systems disclosed herein include automated sampling of environmental data to provide feedback to a network of liquid dispenser devices in order to manage the liquids. In embodiments, running out of liquid results in slowing down delivery (e.g., smaller squirts of hand soap).

In embodiments, methods and systems disclosed herein include modification of a liquid delivered by a network of liquid dispenser devices based on feedback from automated sampling, wherein modifying is by selection/adjustment of one or more of a plurality of available liquid modifiers onboard one or more networked liquid dispenser devices. In embodiments, a master dispenser unit adjusts its own output level and the output level of its slaves upward or downward, proportionately based on the new setting.

In embodiments, methods and systems disclosed herein include modification of a liquid profile delivered by a network of liquid dispenser devices based on one or more sensed parameters, wherein modifying is by selection/adjustment of one or more of a plurality of available liquids onboard one or more networked liquid dispenser devices.

In embodiments, methods and systems disclosed herein include a user interface to review status of and manage liquid operations for one or more networks of liquid dispenser devices, including receive data from devices, receive alerts, view/edit schedules and liquid profiles, view one or more maps of liquid dispenser devices, provide alerts to replace cartridges, enable ordering of new cartridges, accept payments for cartridges, renew subscriptions to various services, sense system health (e.g. machine down alerts), change permissions for a user, initiate a ticket and/or workflow, assign a service technician, add or remove a device, and/or add or remove a customer, division, store or the like. The user interface can be for a smartphone/tablet app. The user interface can be a configurable dashboard.

In embodiments, methods and systems disclosed herein include a liquid media-based advertising platform, wherein liquid dispensing space is bid upon by one or more advertisers. In embodiments the platform is further a mixed-media advertising platform, enabling advertisers to purchase liquid space as well as print/image space, manage an ad campaign including blocking other liquid-based advertisers, and the like. In embodiments, the liquid-based advertising space comprises one or more networked liquid dispenser devices.

In embodiments, methods and systems disclosed herein include determining CPM for a brand impression, wherein the brand impression is exposure to a liquid delivered by one or more managed, networked liquid dispenser devices. In embodiments the methods and systems measure and record what was delivered, how many people received it, what people did when they received it (e.g., with A/B testing of liquid variants), and/or take feedback from users, such as through a survey delivered from a networked liquid dispenser.

In embodiments, methods and systems disclosed herein include determining sales lift by comparing the purchase behavior of a group of participants exposed to a liquid in a retail environment with a group of participants in a comparable retail environment who were not exposed to the liquid. In embodiments the liquid exposure is from one or more networked liquid dispenser devices.

In embodiments, methods and systems disclosed herein include a networked liquid dispenser device integrated with an object to provide a brand impression and/or coordinate with a function of the object. In embodiments, signage changes as available liquids change.

In embodiments, methods and systems disclosed herein include a handheld device for controlling one or more networked liquid dispenser devices, such as a smart phone or tablet.

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platform. A processor may be any kind of computational or processing device capable of executing program instructions, codes, binary instructions and the like. The processor may be or may include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server, cloud server, and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server. The methods and systems may employ a machine-to-machine network.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network having multiple cells. The cellular network may either be frequency division multiple access (FDMA) networks or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, methods described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

All documents referenced herein are hereby incorporated by reference.

What is claimed is:

1. A method, comprising:
receiving, via the internet, at a computer remote from an environment, at least one sensed scent parameter for the environment from a scent sensor in the environment;
determining, at the computer remote from the environment, an operational parameter of at least one scent diffusion device within the environment for achieving a target value of the scent parameter based on the sensed scent parameter data; and
transmitting from the computer to the at least one scent diffusion device in the environment, an instruction via the internet to initiate diffusion of a scent therefrom to achieve the target value of the scent parameter, wherein the instruction includes at least one of setting and adjusting the determined operation parameter of the at least one scent diffusion device.

2. The method of claim 1, wherein the sensed scent parameter data further relates to at least one of room volume, room geometry, room area, airflow, presence of odor-producing materials, presence of odor-sinking factors, lighting, altitude, traffic flow, occupancy detection, proximity sensing, detected odor, fragrance level, temperature, humidity, time of day, season, weather event, detection of a VIP/specific individual entering the space, information about an HVAC system, and information about a building.

3. The method of claim 1, wherein the scent diffusion device includes at least one package containing fragrance oil.

4. The method of claim 1, wherein the scent diffusion device includes at least two packages containing fragrance oil.

5. The method of claim 1, wherein at least one scent diffusion device is a master node and at least one other scent diffusion device is a slave node, wherein the control instructions are sent from the remote computer through the master node.

6. The method of claim 1, wherein the scent diffusion devices relay control instructions from the remote computer in at least one of a series, a ring, a mesh, and a star networking topology.

7. The method of claim 5, wherein each scent diffusion device can adjust its own control settings based on the activities of the other scent diffusion devices.

8. The method of claim 5, further comprising, configuring the at least one scent diffusion device so that a device duty cycle does or does not occur simultaneously within proximity to another scent diffusion device.

9. The method of claim 1, wherein the scent parameter relates to a brand management goal.

10. The method of claim 1, further comprising determining the total number of scent diffusion devices to dispose in the environment based on a room volume.

11. The method of claim 1, further comprising determining one or more locations to dispose the scent diffusion devices in the environment based on a room volume.

12. The method of claim 1, wherein the operation parameter comprises at least one of a flow rate of the liquid, a duration of flow of the liquid, a variation in the flow rate of the liquid, an on/off status of the diffusion device, a package from which to diffuse the liquid, and a switch to a different package from which to diffuse the liquid.

13. A method, comprising:
providing a sensed level of an airborne substance as feedback from a scent sensor in an environment to a scent diffusion device;
adjusting an operation parameter of the scent diffusion device in response to the feedback, wherein adjusting enables the maintenance of a scent profile in the environment; and
communicating the adjustment to other scent diffusion devices in a network of scent diffusion devices,
wherein the scent sensor is located in the environment and is separated and at a distance from the scent diffusion device.

14. The method of claim 13, wherein adjusting is by selection/adjustment of one or more of a plurality of available scent modifiers onboard the scent diffusion devices.

15. The method of claim 13, wherein a user adjusts an overall level of a fragrance desired in the space and a scent diffusion device controller determines the adjustment required for the one or more devices.

16. The method of claim 13, wherein adjusting involves a master diffusion unit of the network of scent diffusion devices adjusting its own output level and the output level of its slaves upward or downward, proportionately based on the adjusted operation parameter.

17. The method of claim 13, wherein the sensed level indicates the presence of a malodor and the operation parameter is adjusted to provide a scent neutralization.

18. The method of claim 13, wherein the sensed level indicates the presence of a malodor and the operation parameter is adjusted to terminate diffusion of the scent.

19. The method of claim 16, wherein the sensed level indicates the presence of at least one of an allergen, a bacteria, a virus, a chemical and an airborne pathogen, and the operation parameter is adjusted to counteract the presence.

20. A method, comprising:
receiving at a computer at least one target value of a scent parameter from a scent sensor for an environment that is remote from the computer;
receiving at the computer a sensed parameter of the environment; and
controlling, via the computer, diffusion of a liquid from a source of the liquid in fluid communication with at least one scent diffusion device to achieve the target value of the scent parameter,
wherein controlling includes setting or adjusting an operation parameter of the at least one scent diffusion device in response to the sensed parameter, and
wherein the scent sensor is located in the environment and is separated and at a distance from the at least one scent diffusion device.

21. The method of claim 20, wherein one of the at least one scent diffusion devices is a master node and the other scent diffusion devices are slave nodes and receive control instructions from the remote computer through the master node.

22. The method of claim 20, wherein at least one of the scent diffusion devices receives control instructions from the remote computer and relays control instructions to at least one other scent diffusion device.

23. The method of claim 20, wherein the scent parameter relates to a brand management goal.

24. The method of claim 20, wherein the operation parameter comprises at least one of a flow rate of the liquid, a duration of flow of the liquid, a variation in the flow rate of the liquid, an on/off status of the diffusion device, a package from which to diffuse the liquid, and a switch to a different package from which to diffuse the liquid.

25. A method of managing scent in an environment, comprising:
   taking an electronic data structure characterizing the transformation of at least one diffusion device disposed within an environment, wherein the electronic data structure includes data regarding a sensed parameter from a scent sensor of the environment;
   accessing at the remote computer, a target value of a scent parameter; and
   providing a service plan for the at least one diffusion device based on the electronic data structure and the target value of the scent parameter,
   wherein the scent sensor is located in the environment and is separated and at a distance from the at least one diffusion device.

26. The method of claim 25, wherein the sensed scent parameter data further relates to at least one of room volume, room geometry, room area, airflow, presence of odor-producing materials, presence of odor-sinking factors, lighting, altitude, traffic flow, occupancy detection, proximity sensing, detected odor, fragrance level, temperature, humidity, time of day, season, weather event, detection of a VIP/specific individual entering the space, information about an HVAC system, and information about a building.

27. The method of claim 25, wherein servicing includes configuring the at least one scent diffusion device so that a device duty cycle does or does not occur simultaneously within proximity to another scent diffusion device.

28. The method of claim 25, wherein the scent parameter relates to a brand management goal.

29. The method of claim 25, wherein the operation parameter comprises at least one of a flow rate of the liquid, a duration of flow of the liquid, a variation in the flow rate of the liquid, an on/off status of the diffusion device, a package from which to diffuse the liquid, and a switch to a different package from which to diffuse the liquid.

30. A method of managing scent in an environment, comprising:
   disposing at least one sensor within the environment that transmits sensor data to a remote computer; and
   disposing at least one scent diffusion device within an environment, wherein the at least one scent diffusion device comprises a communications facility that enables receiving a signal from the remote computer, wherein the signal is a setting or an adjusting of an operation parameter of the at least one scent diffusion device in response to the sensor data to achieve a target value of a scent parameter,
   wherein the scent sensor is located in the environment and is separated and at a distance from the at least one scent diffusion device.

31. The method of claim 30, further comprising determining the total number of scent diffusion devices to dispose in the environment based on a room volume.

32. The method of claim 30, further comprising determining one or more locations to dispose the scent diffusion devices in the environment based on a room volume.

33. The method of claim 30, further comprising, configuring the at least one scent diffusion device so that a device duty cycle does or does not occur simultaneously within proximity to another scent diffusion device.

34. The method of claim 30, wherein the sensed parameter relates to a distance from the scent diffusion device to a scent target location.

35. A method of managing scent in an environment, comprising:
   creating, via a remote computer, an electronic data structure characterizing the transformation of at least one remote scent diffusion device, wherein the electronic data structure includes data regarding a sensed parameter of an environment and at least one target value of a scent parameter for the environment; and
   initiating control, via the remote computer, of diffusion of a liquid from a source of the liquid in fluid communication with the at least one remote scent diffusion device in accordance with the electronic data structure to achieve the target value of the scent parameter in response to the sensed parameter,
   wherein the scent sensor is located in the environment and is separated and at a distance from the at least one remote scent diffusion device.

36. The method of claim 35, wherein the sensed parameter data further relates to at least one of room volume, room geometry, room area, airflow, presence of odor-producing materials, presence of odor-sinking factors, lighting, air flow, altitude, traffic flow, occupancy detection, proximity sensing, detected odor, fragrance level, temperature, humidity, time of day, season, weather event, information about an HVAC system, information about a building, and detection of a VIP/specific individual entering the space.

37. The method of claim 35, wherein the scent diffusion device includes at least two packages containing fragrance oil.

38. The method of claim 35, wherein the scent parameter further relates to a brand management goal.

39. The method of claim 35, wherein the sensed parameter that relates to fragrance level is determined by at least one of measuring a proxy/tag dispersed with the fragrance, measuring an electrostatic charge, measuring a component of the fragrance, measuring an odorless marker diffused with the fragrance, measuring particles, and measuring a concentration of volatile organic compounds.

40. A method, comprising:
   providing a first sensed level of a first airborne substance in a first environment to a central server positioned remotely from the first environment;
   providing a second sensed level of a second airborne substance in a second environment to the central server positioned remotely from the second environment, wherein the second environment is remote from the first environment;
   adjusting via the central server, a first operation parameter of a first scent diffusion device in the first environment in response to the first sensed level of the first airborne substance in the first environment, wherein adjusting enables the maintenance of a first scent profile in the first environment; and
   adjusting via the central server, a second operational parameter of a second scent diffusion device in the second environment in response to the second sensed level of the second airborne substance in the second environment, wherein adjusting enables the maintenance of a second scent profile in the second environment,
   wherein the first scent sensor is located in the environment and is separated and at a distance from the first scent diffusion device, and wherein the second scent senor is located in the environment and is separated and at a distance from the second scent diffusion device.

41. The method of claim 40 wherein the first and second airborne substances are the same, and wherein the first and second scent profiles are the same.

42. The method of claim 40 wherein:
the first sensed level of the first airborne substance includes a first plurality of sensed levels of a plurality of first airborne substances in the first environment;
the second sensed level of the second airborne substance includes a second plurality of sensed levels of a plurality of second airborne substances in the second environment; and
additional sensed levels of additional airborne substances in additional environments are provided to the central server positioned remotely from said environments, wherein the additional environments are remote from the first and second environments.

* * * * *